United States Patent
Pulé et al.

(10) Patent No.: US 11,885,807 B2
(45) Date of Patent: *Jan. 30, 2024

(54) METHOD FOR DEPLETING MALIGNANT T-CELLS

(71) Applicant: AUTOLUS LIMITED, London (GB)

(72) Inventors: Martin Pulé, London (GB); Paul Maciocia, London (GB)

(73) Assignee: AUTOLUS LIMITED, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/832,371

(22) Filed: Jun. 3, 2022

(65) Prior Publication Data

US 2023/0018688 A1 Jan. 19, 2023

Related U.S. Application Data

(63) Continuation of application No. 16/229,684, filed on Dec. 21, 2018, now Pat. No. 11,385,233, which is a continuation of application No. 15/606,480, filed on May 26, 2017, now abandoned, which is a continuation of application No. 15/123,287, filed as application No. PCT/GB2015/050643 on Mar. 5, 2015, now abandoned.

(30) Foreign Application Priority Data

Mar. 5, 2014 (GB) ..................................... 1403905
Sep. 25, 2014 (GB) ..................................... 1416908

(51) Int. Cl.
| | | |
|---|---|---|
| *G01N 33/574* | (2006.01) | |
| *G16H 50/30* | (2018.01) | |
| *C12Q 1/6886* | (2018.01) | |
| *C12Q 1/686* | (2018.01) | |
| *A61K 39/00* | (2006.01) | |

(52) U.S. Cl.
CPC ..... *G01N 33/57492* (2013.01); *C12Q 1/6886* (2013.01); *G16H 50/30* (2018.01); *A61K 2039/515* (2013.01); *C12Q 1/686* (2013.01)

(58) Field of Classification Search
CPC .................................................. G01N 33/57492
See application file for complete search history.

(56) References Cited

U.S. PATENT DOCUMENTS

| | | | |
|---|---|---|---|
| 6,790,604 | B1 | 9/2004 | Cohen et al. |
| 7,709,189 | B1 | 5/2010 | Cohen |
| 11,434,293 | B2 | 9/2022 | Cordoba et al. |
| 11,440,961 | B2 | 9/2022 | Cordoba et al. |
| 2014/0349402 | A1 | 11/2014 | Cooper et al. |
| 2016/0081314 | A1 | 3/2016 | Thurston et al. |
| 2016/0348073 | A1 | 12/2016 | Meissner et al. |
| 2017/0137885 | A1 | 5/2017 | Salomon et al. |
| 2017/0334998 | A1 | 11/2017 | Pule et al. |
| 2019/0209612 | A1 | 7/2019 | Pule et al. |
| 2020/0140549 | A1 | 5/2020 | Cordoba et al. |
| 2021/0355217 | A1 | 11/2021 | Pule et al. |
| 2022/0010377 | A1 | 1/2022 | Onuoha et al. |
| 2022/0041718 | A1 | 2/2022 | Bulek et al. |
| 2022/0098300 | A1 | 3/2022 | Cordoba et al. |
| 2023/0053849 | A1 | 2/2023 | Cordoba et al. |
| 2023/0109275 | A1 | 4/2023 | Onuoha et al. |

FOREIGN PATENT DOCUMENTS

| | | |
|---|---|---|
| CL | 201301645 | 6/2013 |
| CL | 201600734 | 3/2016 |
| CL | 201601134 | 5/2016 |
| CL | 201601135 | 5/2016 |
| CL | 201700438 | 2/2017 |
| CL | 201702150 | 8/2017 |
| CL | 201702413 | 9/2017 |
| CL | 201602196 | 2/2018 |
| JP | H06502529 A | 3/1994 |
| JP | 2007-527191 A | 9/2007 |
| JP | 2010510493 A | 4/2010 |
| JP | 2013-515509 A | 5/2013 |
| RU | 2355703 C2 | 5/2009 |
| WO | WO-03/093318 A1 | 11/2003 |
| WO | WO-2004/074322 A1 | 9/2004 |
| WO | WO-2009/151628 A2 | 12/2009 |
| WO | WO-2011/090754 A1 | 7/2011 |
| WO | WO-2011/090762 A1 | 7/2011 |
| WO | WO-2012/079000 A1 | 6/2012 |
| WO | WO-2013/074916 A1 | 5/2013 |
| WO | WO-2013/176915 A1 | 11/2013 |
| WO | WO-2015/052538 A1 | 4/2015 |
| WO | WO-2015/075469 A1 | 5/2015 |

(Continued)

OTHER PUBLICATIONS

Riha et al. (2010, Self/Nonself, vol. 1:3, pp. 231-240) (Year: 2010).*
ABCAM product datasheet, ab5465, pp. 1-2, Jun. 16, 2017.
Arber, Journal of Molecular Diagnostics, 2001; vol. 3, No. 4: p. 133-149 (2001).
Ataca et al., Chimeric Antigen Receptor T Cell Therapy in Hematology, *Turk. J. Haematol.* 32:285-94 (2015).
Beckman et al., Antibody constructs in cancer therapy. *Cancer*, 109: 170-9 (2007).
Berger et al., "The growth of cutaneous T-cell lymphoma is stimulated by immature dendritic cells," Blood 99:2829-2939 (2002).
Cespdes et al., Mouse models in oncogenesis and cancer therapy. *Clin. Transl. Oncol.* 8(5): 318-29 (2006).

(Continued)

*Primary Examiner* — Anoop K Singh
*Assistant Examiner* — David A Montanari
(74) *Attorney, Agent, or Firm* — MARSHALL, GERSTEIN & BORUN LLP

(57) ABSTRACT

The present invention relates to a chimeric antigen receptor (CAR) which comprises an antigen-binding domain which selectively binds TOR beta constant region 1 (TRBC1) or TRBC2; cells; such a T cells comprising such a CAR; and the use of such cells for the treatment of a T-cell lymphoma or leukaemia in a subject.

8 Claims, 27 Drawing Sheets
Specification includes a Sequence Listing.

(56) References Cited

FOREIGN PATENT DOCUMENTS

| WO | WO-2015/075470 A1 | 5/2015 |
|---|---|---|
| WO | WO-2015/132604 A1 | 9/2015 |
| WO | WO-2016/030691 A1 | 3/2016 |
| WO | WO-2016/138038 A1 | 9/2016 |
| WO | WO-2016/151315 A1 | 9/2016 |
| WO | WO-2018/224844 A1 | 12/2018 |
| WO | WO-2020/025928 A1 | 2/2020 |
| WO | WO-2020/084290 A1 | 4/2020 |
| WO | WO-2020/089644 A1 | 5/2020 |
| WO | WO-2021/191607 A1 | 9/2021 |

OTHER PUBLICATIONS

Clinical immunology and allergology under the editorship of L. Yeager, 2nd ed., transl. from German, M.: Medicine, 3 volumes, v. 1, p. 219-222 (1990).
Dennis, off by a whisker. *Nature*, 442: 739-41 (2006).
Diamond et al., "Somatic mutation of the T15 heavy chain gives rise to an antibody with autoantibody specificity," Proc. Natl. Acad. Sci. 81:5841-5844 (1984).
Fujimori et al., A modeling analysis of monoclonal antibody percolation through tumors: A binding-site barrier. *J. Nucl. Med.* 31: 1191-8 (1990).
Genovese et al., Molecular Therapy 2011 vol. 19, Supplement 1: Cancer-Immunotherapy II, 498: p. S193.
Huang et al., Recombinant immunotherapeutics: Current state and perspectives regarding the feasibility and market. *Appl. Microbiol. Biotechnol.* 87: 401-10 (2010).
International Search Report and Written Opinion from International Application No. PCT/GB2015/050643 dated Jul. 9, 2015.
Kaiko et al., "Immunology" translated from English, edited by N.B. Serebryanoy, Moscow: Academy, p. 37 (2008).
Koiko et al., "Immunology", trans. from English under the editorship of N.B. Serebryanoy, Moscow: Academy, p. 156, 160 (2008).
Lefranc et al., "The T Cell Receptor FactsBook", Elsevier, Academic Press, pp. 1-397 (2001).
Maciocia et al., Targeting T-cell receptor beta-constant domain for immunotherapy of T-cell malignancies. *Blood*, 128(22): 811 (2016); Abstract only—58th Annual Meeting and Exposition of the American Society of Hematology, San Diego, CA, Dec. 3-6, 2016.
Maciocia et al., Targeting the T cell receptor ß-chain constant region for immunotherapy of T cell malignancies, *Nat. Med.* 23:1416-1423 (2017).
Ohno et al., "Antigen-binding specificities of antibodies are primarily determined by seven residues of $V_H$," Proc. Natl. Acad. Sci. 82:2945-2949 (1985).
Osman et al., Physical association of CD5 and the T cell receptor/CD3 antigen complex on the surface of human T lymphocytes, Eur. J. Immunol. 23:1173-1176 (1993).
Ouchi, "Current Status and Prospects for Antibody Drugs: Trastuzumab," Folia Pharmacologic Japonica (Folia Pharmacol. Jpn.) 136:210-214 (2010).
Rudikoff et al., "Single amino acid substitution altering antigen-binding specificity," Proc. Natl. Acad. Sci. 79:1979-1983 (1982).
Rudnick et al., Affinity and avidity in antibody-based tumor targeting. *Can. Biotherp. Radiopharm.* 34(2): 155-62 (2009).
Savoldo et al., Epstein Barr virus-specific cytotoxic T lymphocytes expressing the anti-CD30 artificial chimeric T-cell receptor for immunotherapy of Hodgkin disease. *Blood* 110(7): 2620-2630 (2007).
Schofield et al., Application of phage display to high throughput antibody generation and characterization. *Genome Biol.* 8: R254 (2007).
Talmadge et al., Murine models to evaluate novel and conventional therapeutic strategies for cancer. *Am. J. Pathol.* 170(3): 793-804 (2007).
Tang et al., "The Foxp3+ regulatory T cell: a jack of all trades, master of regulation," Nat Immunol. 93(3):239-244 (2008).
Thurber et al., Antibody tumor penetration: Transport opposed by systemic and antigen-mediated clearance, *Adv. Drug Deliv. Rev.* 60: 1421-34 (2008).
Torikai et al. BLOOD; 2012; 119:5697-5705.
Viney et al., Generation of monoclonal antibodies against a human T cell receptor beta chain expressed in transgenic mice. *Hybridoma*, 11(6): 701-13 (1992).
Voskoglou-Nomikos et al., Clinical predictive value of the in vitro cell line, human xenograft, and mouse allograft preclinical cancer models. *Clin. Cancer Res.* 9: 4227-39 (2003).
Yarilin, "Fundamentals of Immunology", Moscow: Medicine, pp. 172-174 (1999).
Zhang et al., "Pre-depletion of TRBC1+ T cells promotes the therapeutic efficacy of anti-TRBC1 CART for T-cell malignancies," Molecular Cancer 19:162:2-5 (2020).
Zhong et al., "Chimeric Antigen Receptors Combining 4-1BB and CD28 Signaling Domains Augment $PI_3$ kinase/AKT/Bcl-$X_L$ Activation and CD8+ T Cell-mediated Tumor Eradication," Molecular Therapy 18(2):413-420 (2010).
ABCAM product datasheet, ab18862, "Anti-T-cell receptor beta-1 chain C region antibody" pp. 1-2 (2012).
Baeuerle et al., "Bispecific T-Cell Engaging Antibodies for Cancer Therapy," Cancer Res 69(12):4941-4944 (2009).
Lee et al., "Widespread expressions of immunoglobulin superfamily proteins in cancer cells," Cancer Immunol Immunother 61:89-99 (2012).
Mathas et al., "Gene deregulation and spatial genome reorganization near breakpoints prior to formation of translocations in anaplastic large cell lymphoma," PNAS 106(14):5831-5836 (2009).
Fleischer B., et al., "Reactivity of Mouse T-Cell Hybridomas Expressing Human Vß Gene Segments with Staphylococcal and Streptococcal Superantigens", Infection and Immunity, Mar. 1996, vol. 64 (3), pp. 987-994.
Ochsenreither S., et al., "Relative quantification of TCR Vbeta-chain Families by Real Time PCR for Identification of Clonal T-cell Populations", Journal of Translational Medicine, Biomed Central, vol. 6, No. 1, Jul. 1, 2008 (Jul. 1, 2008 ), p. 34, pp. 1-8, XP021037681, ISSN: 1479- 5876.
Sadelain M., et al., "The Basic Principles of Chimeric Antigen Receptor (CAR) Design," Cancer Discovery, vol. 3 (4), Apr. 2013, pp. 388-398, XP055287277, doi:10.1158/2159-8290.CD-12-0548, ISSN 2159-8274.
Turtle C.J., et al., "Engineered T Cells For Anti-Cancer Therapy," Current Opinion In Immunology, GB, doi:10.1016/j.coi.2012.06. 004, ISSN 0952-7915, XP055272888, Jul. 18, 2012, vol. 24 (5), pp. 633-639.
Swamy et al., "A native antibody-based mobility-shift technique (NAMOS-assay) to determine the stoichiometry of multiprotein complexes," Journal of Immunological Methods 324:78-83 (2007).
Swerdlow et al., "The 2016 revision of the World Health Organization classification of lymphoid neoplasms," Blood 127(20):2375-2390 (2016).
U.S. Appl. No. 17/817,271, filed Aug. 3, 2022.
U.S. Appl. No. 17/832,162, filed Jun. 3, 2022.
U.S. Appl. No. 17/832,225, filed Jun. 3, 2022.
U.S. Appl. No. 17/832,307, filed Jun. 3, 2022.
U.S. Appl. No. 17/832,341, filed Jun. 3, 2022.
U.S. Appl. No. 17/811,828, filed Jul. 11, 2022.

* cited by examiner

TRBC1   1   DIKNVEPPEVAVFEPSEAETSHTQKATLVCLATGFFPDHVELSWWVNGKEVHSGVSTDPQ
TRBC2   1   DIKNVEPPEVAVFEPSEAETSHTQKATLVCLATGFYPDHVELSWWVNGKEVHSGVSTDPQ

TRBC1  61   PLKEQPALNDSRYCLSSRLRVSATFWQNPRNHFRCQVQFYGLSENDEWTQDRAKPVTQIV
TRBC2  61   PLKEQPALNDSRYCLSSRLRVSATFWQNPRNHFRCQVQFYGLSENDEWTQDRAKPVTQIV

TRBC1 121   SAEAWGRADCGFTSVSYQQGVLSATILYEILLGKATLYAVLVSALVLMAMVKRKD
TRBC2 121   SAEAWGRADCGFTSESYQQGVLSATILYEILLGKATLYAVLVSALVLMAMVKRKD

Figure 3

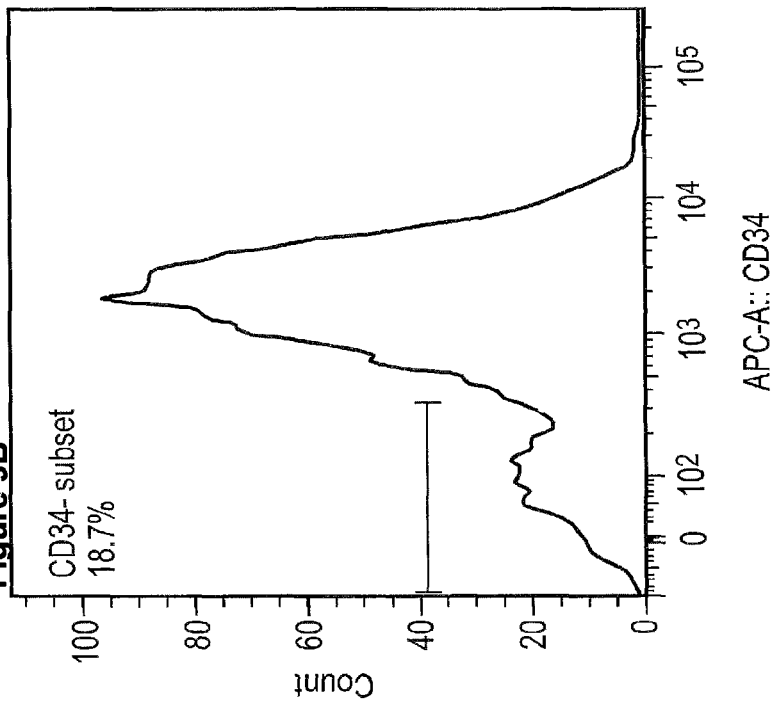
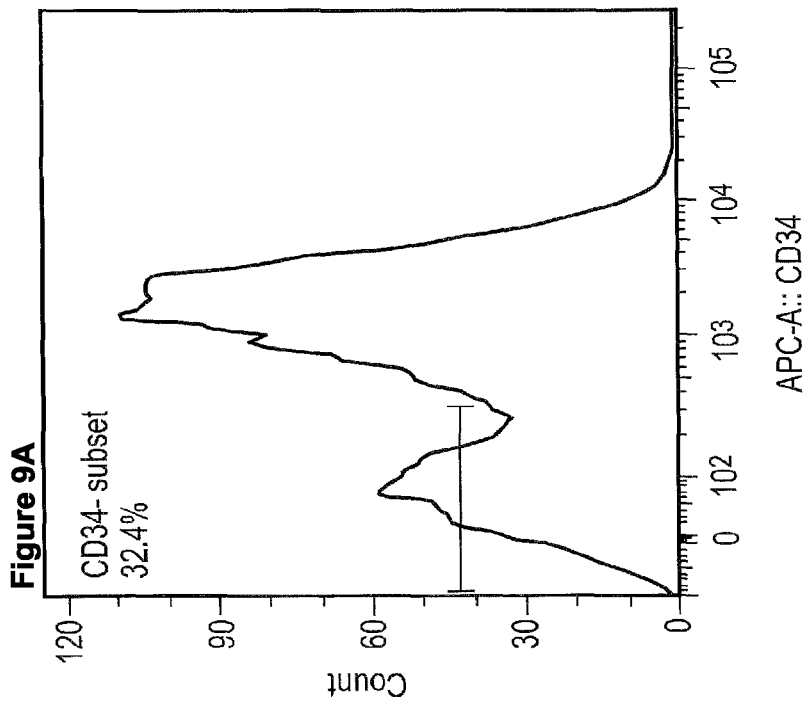

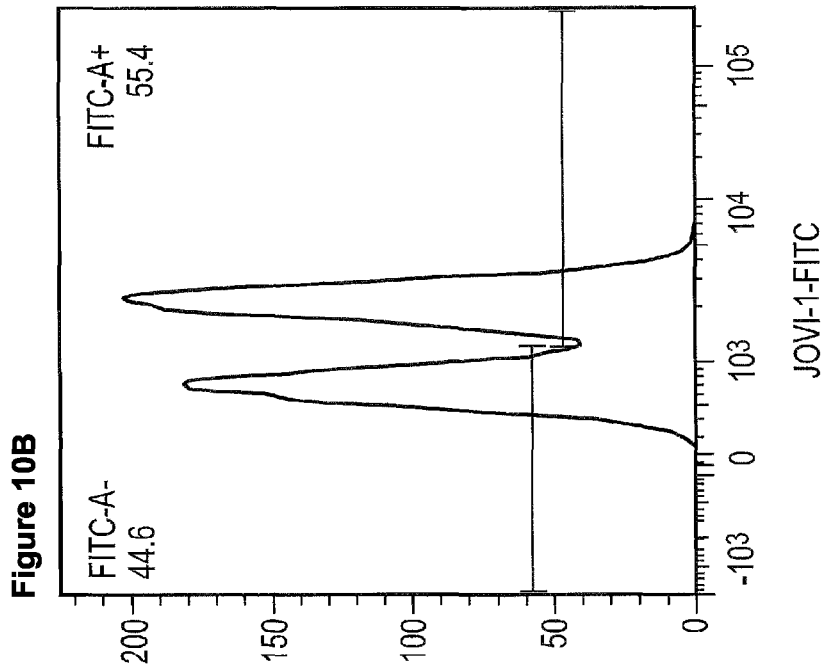
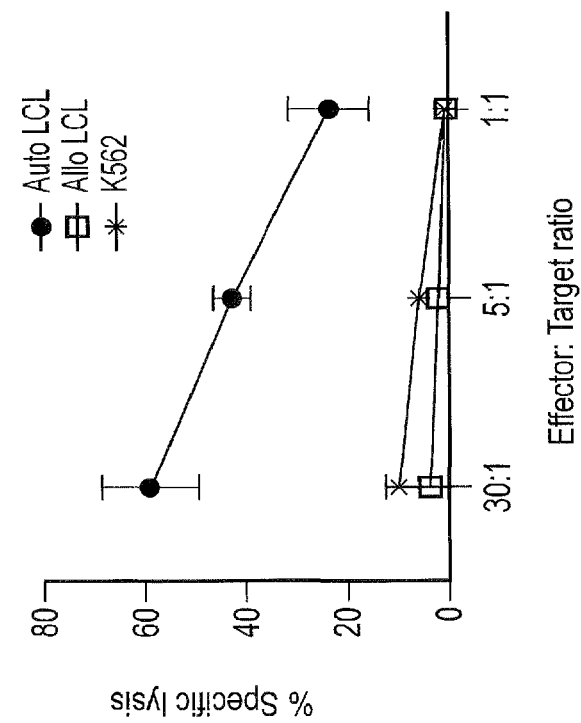

\>VH
EVRLQQSGPDLIKPGASVKMSCKASGYTFTGYVMHWVKQRP
GQGLEWIGFINPYNDDIQSNERFRGKATLTSDKSSTTAYMELSS
LTSEDSAVYYCARGAGYNFDGAYRFFDFWGQGTTLTVSS

\>VL
DVVMTQSPLSLPVSLGDQASISCRSSQRLVHSNGNTYLHWYL
QKPGQSPKLLIYRVSNRFPGVPDRFSGSGSGTDFTLKISRVEAE
DLGIYFCSQSTHVPYTFGGGTKLEIKR

Figure 11

METHOD FOR DEPLETING MALIGNANT T-CELLS

CROSS-REFERENCE TO RELATED APPLICATIONS

This application is a Continuation of U.S. application Ser. No. 16/229,684, filed Dec. 21, 2018, which is a Continuation of U.S. application Ser. No. 15/606,480, filed May 26, 2017, now abandoned, which is a Continuation of U.S. application Ser. No. 15/123,287, filed Sep. 2, 2016, now abandoned, which is a U.S. National Phase of International Application No. PCT/GB2015/050643, filed Mar. 5, 2015, which claims priority to Great Britain Application No. 1416908.0, filed Sep. 25, 2014 and Great Britain Application No. 1403905.1, filed Mar. 5, 2014.

FIELD OF THE INVENTION

The present invention relates to cells and agents useful in the treatment of T-cell lymphoma or leukaemia.

BACKGROUND TO THE INVENTION

Lymphoid malignancies can largely be divided into those which are derived from either T-cells or B-cells. T-cell malignancies are a clinically and biologically heterogeneous group of disorders, together comprising 10-20% of non-Hodgkin's lymphomas and 20% of acute leukaemias. The most commonly identified histological subtypes are peripheral T-cell lymphoma, not otherwise specified (PTCL-NOS); angio-immunoblastic T-cell lymphoma (AITL) and anaplastic large cell lymphoma (ALCL). Of all acute Lymphoblastic Leukaemias (ALL), some 20% are of a T-cell phenotype.

These conditions typically behave aggressively, compared for instance with B-cell malignancies, with estimated 5-year survival of only 30%. In the case of T-cell lymphoma, they are associated with a high proportion of patients presenting with disseminated disease, unfavourable International Prognostic Indicator (IPI) score and prevalence of extra-nodal disease. Chemotherapy alone is not usually effective and less than 30% of patients are cured with current treatments.

Further, unlike in B-cell malignancies, where immunotherapies such as the anti-CD20 monoclonal antibody rituximab have dramatically improved outcomes, there is currently no equivalently effective, minimally toxic immunotherapeutic available for the treatment of T-cell malignancies. An important difficulty in the development of immunotherapy for T-cell disorders is the considerable overlap in marker expression of clonal and normal T-cells, with no single antigen clearly able to identify clonal (malignant) cells.

The same problem exists when targeting a pan-B-cell antigen to treat a B-cell malignancy. However, in this case, the concomitant depletion of the B-cell compartment results in relatively minor immunosuppression which is readily tolerated by most patients. Further, in therapies which result in particularly long-term depletion of the normal B-compartment, its loss can be largely abrogated by administration of pooled immunoglobulin. The situation is completely different when targeting T-cell malignancies. Here, concomitant depletion of the T-cell compartment leads to severe immunosuppression and severe toxicity. Further, there is no satisfactory way to mitigate loss of the T-cell compartment.

The toxicity is in part illustrated by the clinical effects of the therapeutic monoclonal antibody Alemtuzumab. This agent lyses cells which express CD52 and has some efficacy in T-cell malignancies. The utility of this agent is greatly limited by a profound cellular immunodeficiency, largely due to T-cell depletion, with markedly elevated risk of infection.

There is thus a need for a new method for targeted treatment of T-cell malignancies which is not associated with the above disadvantages.

DESCRIPTION OF THE FIGURES

FIG. 3: Alignment of human TRBC1 and TRBC2 at the amino acid level. The TCRβ constant chain coded for by TRBC1 and TRBC2 differ by only 4 amino acid differences: K N at position 3 of the TRBC; N/K at position 4 of the TRBC; F/Y at position 36 of the TRBC; V/E at position 135 of the TRBC;

FIGS. 9A-9B: Selective Killing of TRBC1 T-cells with JOVI-1 mAb. Wild-type Jurkat T-cells (CD34−, TRBC1+) were mixed with TCRαβ knock-out Jurkat T-cells transduced with TRBC2 co-expressed with the CD34 marker gene (CD34+TRBC2+). These cells were incubated with JOVI-1 alone or incubated with JOVI-1 and complement for 1 hour. Cells were washed and stained for CD34, Annexin V and 7-AAD. Cells were analysed by flow-cytometry. Shown below is CD34 expression in the live population as defined by Annexin-V negative and 71AAD dim population. FIG. 9A JOVI-1 alone; FIG. 9B-JOVI-1 with complement. Selective killing of TRBC1 T-cells (CD34-) is observed.

FIGS. 10A-10B: Polyclonal Epstein Barr Virus (EBV) specific T-cells can be split into two approximately equal TRBC1/2 populations. Using well established methods, the inventors selectively expanded EBV specific T-cells from the peripheral blood of a normal donor. The subsequent line had a high degree of selectively against autologous EBV infected B-cells (auto LCLs), and no activity against allogeneic EBV infected T-cells (allo LCLs), and no non-specific NK activity (as measured by testing against K562 cells). Such a line is representative of the donor's EBV immunity. FIG. 10B) When stained with JOVI-1, these T-cells typed approximately equally for TRBC1 and TRBC2.

FIG. 11: Annotated sequence of JOVI-1 VH and VL. The hypervariable regions are underlined and in bold.

FIG. 21A) Two rounds of solid-phase phage display selections on TRBC peptides directly or indirectly immobilised on a surface. FIG. 21B) Three rounds of solution-phase phage display selections on biotinylated TRBC peptides.

(FIG. 25A) After 3rd immunization (FIG. 25B) After 3rd immunization and purification of TRBC1 specific antibodies.

(FIG. 26A) After 3rd immunization (FIG. 26B) After 3rd immunization and purification of TRBC2 specific antibodies.

(FIG. 27A) After 3rd immunization (FIG. 27B) After 3rd immunization and purification of TRBC2 specific antibodies.

SUMMARY OF ASPECTS OF THE INVENTION

Figure 1:
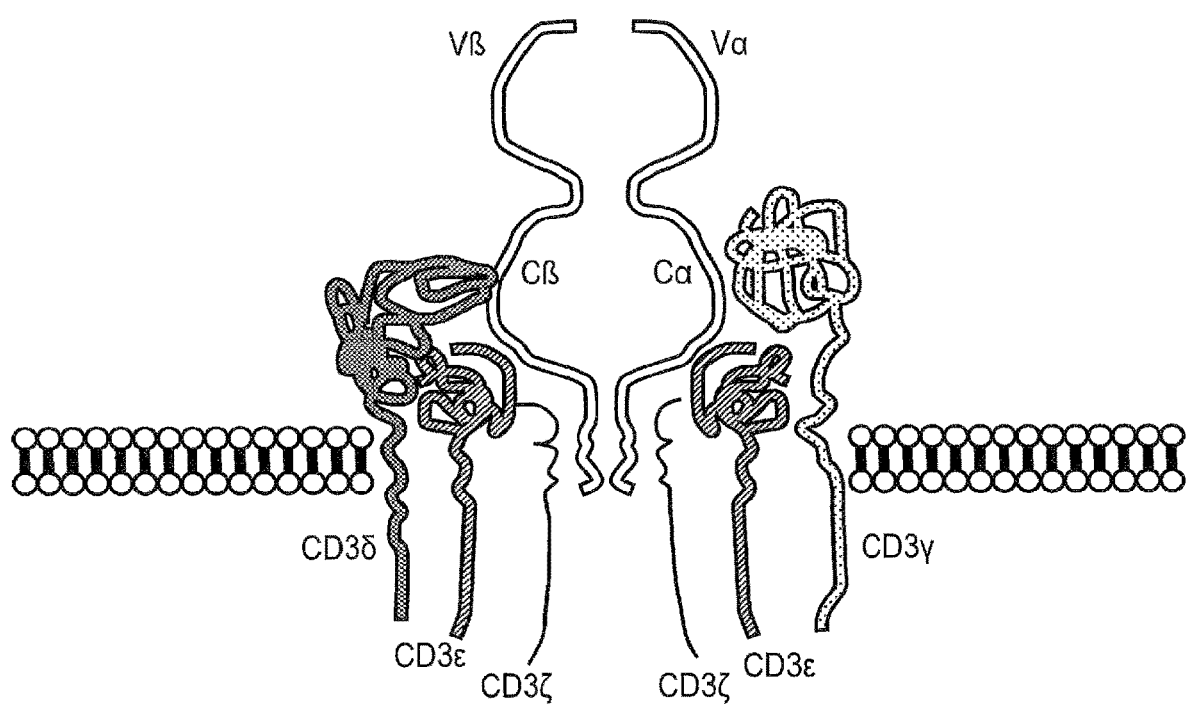
FIG. 1: A diagram of the αβ T-cell Receptor/CD3 Complex. The T-cell receptor is formed from 6 different protein chains which must assemble in the endoplasmic reticulum to be expressed on the cell surface. The four proteins of the CD3 complex (CD3ζ, CD3γ, CD3ε and CD3δ) sheath the T-cell Receptor (TCR). This TCR imbues the complex with specificity of a particular antigen and is composed of two chains: TCRα and TCRβ. Each TCR chain has a variable component distal to the membrane and a constant component proximal to the membrane. Nearly all T-cell lymphomas and many T-cell leukaemias express the TCR/CD3 complex.

The present inventors have devised a method whereby it is possible to deplete malignant T-cells in a subject, without affecting a significant proportion of healthy T cells. In particular, they have developed TRBC1 and TRBC2-specific chimeric antigen receptors (CARs) for use in the treatment of T-cell malignancies.

Thus in a first aspect the present invention provides a chimeric antigen receptor (CAR) which comprises an antigen-binding domain which selectively binds TCR beta constant region 1 (TRBC1) or TRBC2.

In a first embodiment of the first aspect of the invention there is provided a CAR which selectively binds TRBC1. In this embodiment, the CAR may comprise an antigen-binding domain which has a variable heavy chain (VH) and a variable light chain (VL) which comprise the following complementarity determining regions (CDRs):

VH CDR1:;
SEQ ID No. 7

VH CDR2:;
SEQ ID No. 8

VH CDR3:;
SEQ ID No. 9

VL CDR1:;
SEQ ID No. 10

VL CDR2:;
SEQ ID No. 11
and

VL CDR3:.
SEQ ID No. 12

The CAR may comprise an antigen-binding domain which comprises a variable heavy chain (VH) having the sequence shown as SEQ ID No. 1 and a variable light chain (VL) having the sequence shown as SEQ ID No. 2.

The CAR may comprise an antigen-binding domain which comprises an scFv having the amino acid sequence shown as SEQ ID No, 3.

The CAR may comprise an amino acid sequence selected from SEQ ID No. 33, 34 and 35.

The CAR may comprise a VH CDR3 and/or a VL CDR3 from those listed in Table 1.

The CAR may comprise an antibody or functional fragment thereof which comprises:
(i) the heavy chain CDR3 and/or the light chain CDR3;
(ii) heavy chain CDR1, CDR2 and CDR3 and/or light chain CDR1, CDR2 and CDR3; or
(iii) the variable heavy chain (VH) and/or the variable light chain (VL); from one of the scFvs shown as SEQ ID No. 13 to 22.

In a second embodiment of the first aspect of the invention there is provided a CAR which selectively binds TRBC2.

In connection with this embodiment, the CAR may comprise a VH CDR3 and/or a VL CDR3 from those listed in Table 2.

The CAR may comprise an antibody or functional fragment thereof which comprises:
(i) the heavy chain CDR3 and/or the light chain CDR3;
(ii) heavy chain CDR1, CDR2 and CDR3 and/or light chain CDR1, CDR2 and CDR3; or
(iii) the variable heavy chain (VH) and/or the variable light chain (VL); from one of the scFvs shown as SEQ ID No. 23 to 32.

In a second aspect, the present invention provides a nucleic add sequence encoding a CAR according to the first aspect of the invention.

In a third aspect, there is provided a vector which comprises a nucleic acid sequence according to the second aspect of the invention.

In a fourth aspect, there is provided a cell which comprises a CAR according to the first aspect of the invention. The cell may be a cytolytic immune cell, such as a T-cell or natural killer (NK) cell.

In a fifth aspect there is provided a method for making a cell according to the fourth aspect of the invention which comprises the step of transducing or transfecting a cell with a nucleic acid sequence according to the second aspect of the invention or a vector according to the third aspect of the invention.

In a sixth aspect there is provided a cell according to the fourth aspect of the invention for use in a method for treating a T-cell lymphoma or leukaemia in a subject which comprises the step of administrating the cell comprising the TCRB1 or TCRB2 selective CAR to the subject, to cause selective depletion of the malignant T-cells, together with normal T-cells expressing the same TRBC as the malignant T-cells, but not to cause depletion of normal T-cells expressing the TRBC not expressed by the malignant T-cells.

The method may also comprise the step of investigating the TCR beta constant region (TCRB) of a malignant T cell from the subject to determine whether it expresses TRBC1 or TRBC2.

There is also provided a method for treating a T-cell lymphoma or leukaemia in a subject which comprises the step of administering a TCRB1 or TCRB2 selective agent to the subject, wherein the agent causes selective depletion of the malignant T-cells, together with normal T-cells expressing the same TRBC as the malignant T-cells, but does not cause depletion of normal T-cells expressing the TRBC not expressed by the malignant T-cells.

In a first embodiment of this aspect of the invention, the agent is a TCRB1 selective agent. In a second embodiment of this aspect of the invention, the agent is a TRBC2 selective agent.

The method may also comprise the step of investigating the TOR beta constant region (TRBC) of a malignant T-cell to determine whether it expresses TRBC1 or TRBC2, prior to the administration step.

The agent may be a depleting monoclonal antibody or a fragment thereof. The agent may be a conjugated antibody, which may comprise a chemotherapeutic entity.

The agent may be a bispecific T-cell engager. The agent may be a chimeric antigen receptor (CAR) expressing T-cell. The CAR may comprise an amino acid sequence selected from the group consisting of SEQ ID No. 33, 34 and 35.

The agent may comprise the JOVI-1 antibody or a functional fragment thereof.

The agent may comprise an antibody or a functional fragment thereof having a variable heavy chain (VH) and a variable light chain (VL) which comprise the following complementarity determining regions (CDRs):

```
VH CDR1:;
SEQ ID No. 7

VH CDR2:;
SEQ ID No. 8

VH CDR3:;
SEQ ID No. 9

VL CDR1:;
SEQ ID No. 10

VL CDR2:;
SEQ ID No. 11
and

VL CDR3:.
SEQ ID No. 12
```

The agent may comprise an antibody of functional fragment thereof which comprises a variable heavy chain (VH) having the amino add sequence shown as SEQ ID No. 1 and a variable light chain (VL) having the amino acid sequence shown as SEQ ID No. 2.

The agent may comprise an ScFv having the amino acid sequence shown as SEQ ID No. 3. The agent may be provided as a pharmaceutical composition.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

The present invention also provides an agent for use in treating a T-cell lymphoma or leukaemia according to such a method.

The present invention also provides a kit comprising an agent for use as defined above.

The present invention also provides the use of an agent in the manufacture of a medicament for treatment of a T-cell lymphoma or leukaemia according to the above method.

The present invention also provides a method for diagnosing a T-cell lymphoma or leukaemia in a subject which comprises the step of determining the percentage of total T-cells in a sample which are TRBC1 or TRBC2 positive.

A percentage of TRBC1 or TRBC2 positive T-cells which is greater than about 80% may indicate the presence of a T-cell lymphoma or leukaemia.

The sample may be a peripheral blood sample or a biopsy.
The agent which binds total T-cells may bind CD3.

DETAILED DESCRIPTION

The present invention provides agents, such as chimeric antigen receptors (CARs) which selectively bind TRBC1 or TRBC2. Such agents are useful in methods for treating a T-cell lymphoma or leukaemia in a subject. T cell malignancies are clonal, so they either express TRBC1 or TRBC2. By administering a TCRB1 or TCRB2 selective agent to the subject, the agent causes selective depletion of the malignant T-cells, together with normal T-cells expressing the same TRBC as the malignant T-cells, but does not cause depletion of normal T-cells expressing the TRBC not expressed by the malignant T-cells.

TCR β Constant Region (TRBC)

The T-cell receptor (TCR) is expressed on the surface of T lymphocytes and is responsible for recognizing antigens bound to major histocompatibility complex (MHC) molecules. When the TCR engages with antigenic peptide and MHC (peptide/MHC), the T lymphocyte is activated through a series of biochemical events mediated by associated enzymes, co-receptors, specialized adaptor molecules, and activated or released transcription factors.

The TCR is a disulfide-linked membrane-anchored heterodimer normally consisting of the highly variable alpha (α) and beta (β) chains expressed as part of a complex with the invariant CD3 chain molecules. T-cells expressing this receptor are referred to as α:β (or αβ) T-cells (~95% total T-cells). A minority of T-cells express an alternate receptor, formed by variable gamma (γ) and delta (δ) chains, and are referred to as γδ T-cells (~5% total T cells).

Each α and β chain is composed of two extracellular domains: Variable (V) region and a Constant (C) region, both of Immunoglobulin superfamily (IgSF) domain forming antiparallel β-sheets. The constant region is proximal to the cell membrane, followed by a transmembrane region and a short cytoplasmic tail, while the variable region binds to the peptide/MHC complex (see FIG. 1). The constant region of the TCR consists of short connecting sequences in which a cysteine residue forms disulfide bonds, which forms a link between the two chains.

The variable domains of both the TCR α-chain and β-chain have three hypervariable or complementarity determining regions (CDRs). The variable region of the β-chain also has an additional area of hypervariability (HV4), however, this does not normally contact antigen and is therefore not considered a CDR.

The TCR also comprises up to five invariant chains γ, δ, ε (collectively termed CD3) and ζ. The CD3 and t subunits mediate TCR signalling through specific cytoplasmic domains which interact with second-messenger and adapter molecules following the recognition of the antigen by αβ or γδ. Cell-surface expression of the TCR complex is preceded by the pair-wise assembly of subunits in which both the transmembrane and extracellular domains of TCR α and β and CD3 γ and δ play a role TCRs are therefore commonly composed of the CD3 complex and the TCR α and β chains, which are in turn composed of variable and constant regions (FIG. 1).

Figure 2:
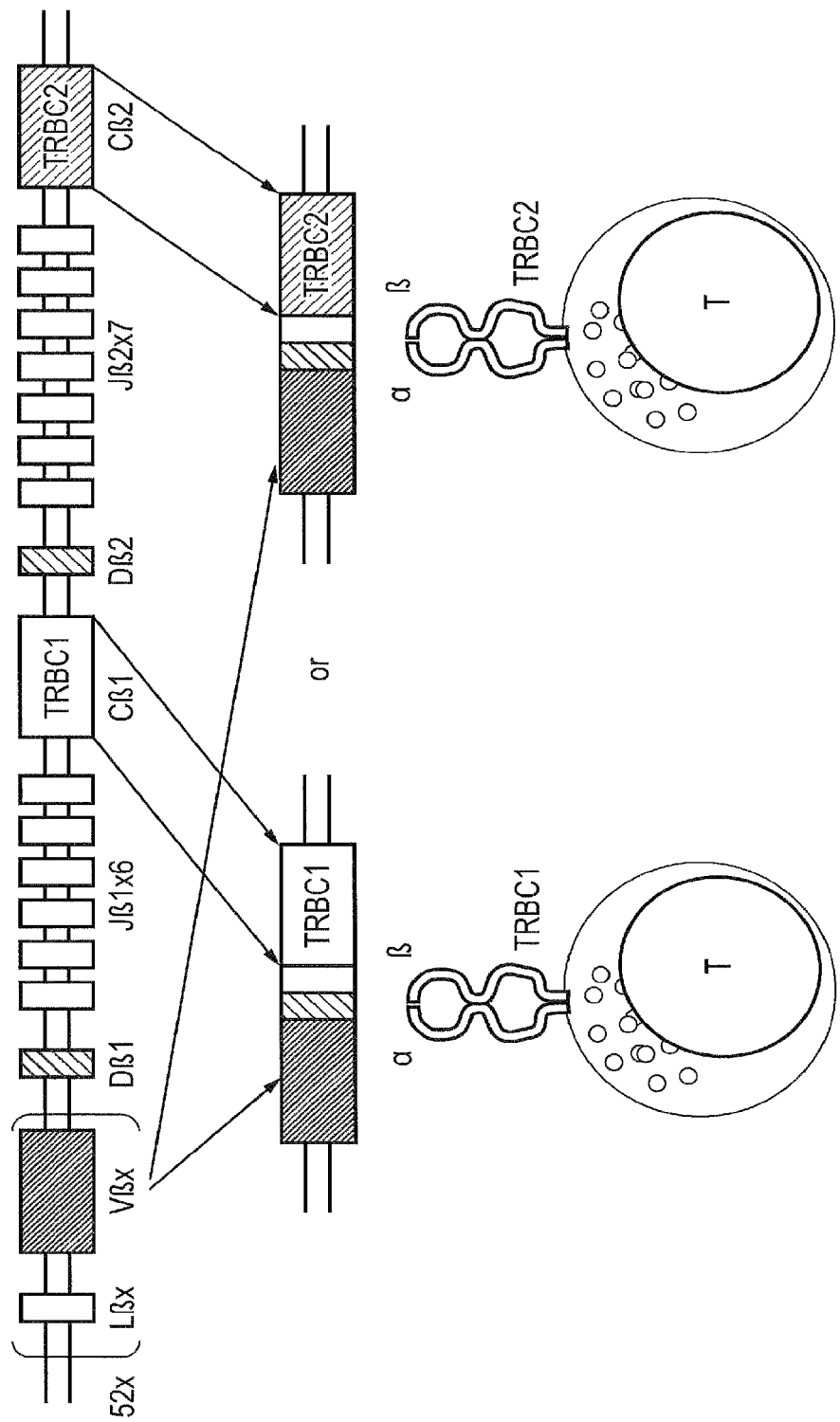
FIG. 2: The segregation of T-cell Receptor β-constant region (TRBC)-1 and TRBC2 during T-cell receptor rearrangement. Each TCR beta chain is formed from genomic recombination of a particular beta variable (V), diversity (D), joining (J) and constant (TRBC) regions. The human genome contains two very similar and functionally equivalent TRBC loci known as TRBC1 and TRBC2. During TCR gene re-arrangement, a J-region recombines with either TRBC1 or TRBC2. This rearrangement is permanent. T-cells express many copies of a single TCR on their surface, hence each T-cell will express a TCR whose β-chain constant region is coded for by either TRBC1 or TRBC2.

The locus (Chr7:q34) which supplies the TCR β-constant region (TRBC) has duplicated in evolutionary history to produce two almost identical and functionally equivalent genes: TRBC1 and TRBC2 (FIG. 2), which differ by only 4 amino acid in the mature protein produced by each (FIG. 3). Each TCR will comprise, in a mutually exclusive fashion, either TRBC1 or TRBC2 and as such, each αβ T-cell will express either TRBC1 or TRBC2, in a mutually exclusive manner.

The present inventors have determined that, despite the similarity between the sequence of the TRBC1 and TRBC2, it is possible to discriminate between them. The inventors have also determined that amino acid sequences of TRBC1 and TRBC2 can be discriminated whilst in situ on the surface of a cell, for example a T-cell.

Malignant Cells

The term 'malignant' is used herein according to its standard meaning to refer to a cell which is not self-limited in its growth, may be capable of invading into adjacent tissues and may be capable of spreading to distant tissue. As such the term 'malignant T cell' is used herein to refer to a clonally expanded T cell in the context of a lymphoma or leukaemia.

The method of the present invention involves determining the TRBC of a malignant T-cell. This may be performed using methods known in the art. For example it may be determined by PCR, western blot, flow cytometry or fluorescent microscopy methods.

Once the TRBC expressed by a malignant T-cell has been determined, the appropriate TRBC1 or TRBC2 selective agent is administered to the subject. The 'appropriate TRBC selective agent' means that where the malignant T-cell is determined to express TRBC1, a TRBC1 selective agent is administered, whereas where the malignant T-cell is determined to express TRBC2, a TRBC2 selective agent is administered.

Selective Agent

The selective agent binds to either TRBC1 or TRBC2 in a mutually exclusive manner.

As stated above, each αβ T-cell expresses a TCR which comprises either TRBC1 or TRBC2. In a clonal T-cell disorder, such as a T-cell lymphoma or leukaemia, malignant T-cells derived from the same clone will all express either TRBC1 or TRBC2.

Thus the present method comprises the step of administering a TRBC1 or TRBC2 selective agent to the subject, wherein the agent causes selective depletion of the malignant T-cells, together with normal T-cells which express the same TRBC as the malignant T-cells, but does not cause significant depletion of normal T-cells expressing the other TRBC from the malignant T-cells.

Because the TRBC selective agent does not cause significant depletion of normal T-cells expressing the other TRBC from the malignant T-cells it does not cause depletion of the entire T-cell compartment. Retention of a proportion of the subject's T-cell compartment (i.e. T-cells which do not express the same TRBC as the malignant T-cell) results in reduced toxicity and reduced cellular and humoral immunodeficiency, thereby reducing the risk of infection.

Administration of a TRBC1 selective agent according to the method of the present invention may result in a 5, 10, 20, 50, 75, 90, 95 or 99% depletion, i.e. reduction in the number of T-cells expressing TRBC1.

Administration of a TRBC2 selective agent according to the method of the present invention may result in a 5, 10, 20, 50, 75, 90, 95 or 99% depletion, i.e. reduction in the number of T-cells expressing TRBC2.

A TRBC1 selective agent may bind TRBC1 with an at least 2-fold, 4-fold, 5-fold, 7-fold or 10-fold greater affinity that TRBC2. Likewise, a TRBC2 selective agent may bind TRBC2 with an at least 2-fold, 4-fold, 5-fold, 7-fold or 10-fold greater affinity that TRBC1.

A TRBC1 selective agent causes depletion of a greater proportion of TRBC1-expressing T-cells in cell population than TRBC2-expressing cell. For example, the ratio of depletion of TRBC1-expressing T-cells to TRBC2-expressing cells may be at least 60%:40%, 70%:30%, 80%:20%, 90%:10% or 95%:5%. Likewise, a TRBC2 selective agent causes depletion of a greater proportion of TRBC1-expressing T-cells in cell population than TRBC2-expressing cell. For example, the ratio of depletion of TRBC2-expressing T-cells to TRBC1-expressing cells may be at least 60%: 40%, 70%:30%, 80%:20%, 90%:10% or 95%:5%.

Using the method of the invention, malignant T-cells are deleted in a subject, without affecting a significant proportion of healthy T cells. By "a significant proportion" it is meant that a sufficient proportion of T cells expressing the TRBC different from the malignant T cells survive in order to maintain T-cell function in the subject. The agent may cause depletion of less than 20%, 15%, 10% or 5% of the T-cell population expressing the other TCRB.

The selective agent may be selective for either TRBC1 or TRBC2 because it discriminates residues as listed below:
(i) N from K at position 3 of the TRBC;
(ii) K from N at position 3 of the TRBC;
(iii) K from N at position 4 of the TRBC;
(iv) N from K at position 4 of the TRBC;
(v) F from Y at position 36 of the TRBC;
(vi) Y from F at position 36 of the TRBC;
(vii) V from E at position 135 of the TRBC; and/or
(viii) E from V at position 135 of the TRBC.

The selective agent may discriminate any combination of the differences above differences.

Antibody

The agent used in the method of the present invention may be a depleting monoclonal antibody (mAb) or a functional fragment thereof, or an antibody mimetic.

The term 'depleting antibody' is used in the conventional sense to relate to an antibody which binds to an antigen present on a target T-cell and mediates death of the target T-cell. The administration of a depleting antibody to a subject therefore results in a reduction/decrease in the number of cells within the subject which express the target antigen.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'2, Fv, single chain Fv (ScFv) fragment or Nanobody. The antibody may be a bifunctional antibody. The antibody may be non-human, chimeric, humanised or fully human.

The antibody may therefore be any functional fragment which retains the antigen specificity of the full antibody.

TRBC1-Selective Antibodies

The agent for use in the method of the present invention may comprise an antibody or a functional fragment thereof having a variable heavy chain (VH) and a variable light chain (VL) which comprises one or more of the following complementarity determining regions (CDRs):

```
VH CDR1:
                                    (SEQ ID No. 7)
GYTFTGY;

VH CDR2:
                                    (SEQ ID No. 8)
NPYNDD;

VH CDR3:
                                    (SEQ ID No. 9)
GAGYNFDGAYRFFDF;

VL CDR1:
                                    (SEQ ID No. 10)
RSSQRLVHSNGNTYLH;

VL CDR2:
                                    (SEQ ID No. 11)
RVSNRFP;
and

VL CDR3:
                                    (SEQ ID No. 12)
SQSTHVPYT.
```

The one or more CDRs each independently may or may not comprise one or more amino acid mutations (eg substitutions) compared to the sequences given as SEQ ID No. 7 to 12, provided that the resultant antibody retains the ability to selectively bind to TRBC1.

Studies have shown that CDRs L3 and H3 are prevalently responsible for high energy interactions with the antigen, so the antibody or functional fragment thereof, may comprise VH CDR3 and/or VL CDR3 as outlined above.

Using phage display, several additional antibody binding domains have been identified which are highly selective for binding TRBC1 over TRBC2, as described in Example 12.

The agent may comprise an antibody or a functional fragment thereof having a variable heavy chain (VH) and/or a variable light chain (VL) which comprises one or more of the complementarity determining regions (CDR3s) shown in the Table 1.

TABLE 1

| Clone ID | VH germline ID | VL germline ID | Heavy CDR3 | Light CDR3 | TRBC1 binding | TRBC2 Binding |
|---|---|---|---|---|---|---|
| CP_01_E09 | Vh3_DP-46_(3-30.3) | Vk1_DPK1_(O18, O8) | AHNSSSWSF......DY | QQYDNLP......LT | 403248 | 318 |
| CP_01_D12 | Vh3_DP-46_(3-30.3) | Vk1_L12 | GGDTYGFL......DN | QQFNAYP......LT | 392753 | 298 |
| CP_01_D10 | Vh3_DP-49_(3-30.5) | Vk1_DPK9_(O12, O2) | GGGSFGAF......DI | QQYNSYP......LT | 370612 | 306 |
| CP_01_C08 | Vh3_DP-46_(3-30.3) | Vk1_DPK1_(O18, O8) | GYSSSWYL......DY | QQYDNLP......LT | 352814 | 426 |
| CP_01_C11 | Vh1_DP-8, 75_(1-02) | Vlambda6_6a | GGAG......WN | QSHDSSN......VV | 349231 | 622 |
| CP_01_F03 | Vh3_DP-46_(3-30.3) | Vk1_DPK1_(O18, O8) | GYXASSWSQ......GL | QQYDNLP......PT | 335088 | 306 |
| CP_01_E07 | Vh3_DP-49_(3-30.5) | Vk2_DPK12_(A2) | DLGGSGGAF......DI | MQSIQL......YT | 332307 | 394 |
| CP_01_D03 | Vh3_DP-49_(3-30.5) | Vk3_DPK21_(L2) | NKQYGM......DV | QQYHRWP......LT | 327666 | 452 |
| CP_01_F06 | Vh3_DP-49_(3-30.5) | Vk4_DPK24_(B3) | DDGAM......RY | QQYYDSP......YT | 325058 | 286 |
| CP_01_F02 | Vh3_DP-49_(3-30.5) | Vk1_A30 | AGYSYA......DY | LQHNSYP......LT | 301955 | 508 |
| CP_02_C03 | Vh3_DP-46_(3-30.3) | Vk4_DPK24_(B3) | GGRYSSNYF......DY | QQYFGT......PT | 274905 | 374 |
| CP_02_D10 | Vh3_DP-50_(3-33) | Vk3_L16 | VGEGSAM......DV | QQYNDWP......LT | 259096 | 517 |
| CP_02_B01 | Vh3_DP-46_(3-30.3) | Vlambda6_6a | VSSHYDSSGYYAGGF......DY | QSFDTNSL......WV | 258840 | 341 |
| CP_02_D02 | Vh3_DP-49_(3-30.5) | Vk1_DPK1_(O18, O8) | GRDSSSWSP......AY | QQYDNLP......LT | 256223 | 393 |
| CP_02_A02 | Vh3_DP-49_(3-30.5) | Vlambda2_DPL11_(2a2) | VTTYSGLDF......DY | SSYTSSST......VV | 252590 | 385 |
| CP_02_D04 | Vh3_DP-46_(3-30.3) | Vk1_DPK9_(O12, O2) | KGAVWVPGAL......DY | QQYNSYP......LT | 252076 | 493 |
| CP_01_E10 | Vh3_DP-49_(3-30.5) | Vk1_DPK9_(O12, O2) | NSLYGGNSA......DL | QQTFTTP......IT | 238172 | 679 |
| CP_01_H08 | Vh3_DP-49_(3-30.5) | Vk1_DPK1_(O18, O8) | DGGGGRF......DV | QQYDNLP......LT | 223591 | 381 |
| CP_01_F11 | Vh3_DP-46_(3-30.3) | Vlambda6_6a | GGGALGRGM......DV | QSYDTNN......VV | 222976 | 481 |
| CP_01_F09 | Vh5_DP-73_(5-51) | Vk1_DPK1_(O18, O8) | LLRSGGQSYAF......DI | QQSYSTP......LT | 217934 | 308 |
| CP_02_D05 | Vh3_DP-46_(3-30.3) | Vk1_DPK1_(O18, O8) | GYSSSWSF......DY | QQYDNLP......IT | 212579 | 440 |
| CP_02_A09 | Vh3_DP-46_(3-30.3) | Vk1_DPK1_(O18, O8) | AGSSGWTL......DY | QQYDNLP......LT | 202054 | 336 |
| CP_02_D03 | Vh3_DP-46_(3-30.3) | Vk1_DPK1_(O18, O8) | DKGWGF......DY | QQYDNLP......LT | 199403 | 543 |
| CP_02_C11 | Vh5_DP-73_(5-51) | Vlambda6_6a | LGVVRGVMKGF......DY | QSYDSSN......VV | 189481 | 392 |

TABLE 1-continued

| Clone ID | VH germline ID | VL germline ID | Heavy CDR3 | Light CDR3 | TRBC1 binding | TRBC2 Binding |
|---|---|---|---|---|---|---|
| CP_01_H10 | Vh3_DP-49_(3-30.5) | Vk1_DPK1_(O18, O8) | SSYSSSWGM......DV | QQYDNLP......LT | 179830 | 424 |
| CP_02_C04 | Vh3_DP-49_(3-30.5) | Vk1_DPK9_(O12, O2) | ANSWSAGGM......DV | QQYDDLP......LT | 172937 | 722 |
| CP_01_G03 | Vh3_DP-49_(3-30.5) | Vk2_DPK13_(O11, O1) | ERGRGYSYM......DV | MQRIEFP......LT | 168169 | 360 |
| CP_01_G06 | Vh3_DP-46_(3-30.3) | Vlambda6_6a | VARGIHDAF......DI | QSYDNTRH......WV | 166703 | 307 |
| CP_01_D06 | Vh3_DP-46_(3-30.3) | Vlambda6_6a | RHGM......DV | QSYDSSN......VV | 162783 | 287 |
| CP_02_B03 | Vh1_DP-8, 75_(1-02) | Vlambda6_6a | FDSSGYYY......DY | QSYDSSN......VV | 158809 | 312 |
| CP_02_A12 | Vh5_DP-73_(5-51) | Vk3_DPK21_(L2) | DLVTTGAF......DT | QQHNDWP......LT | 152968 | 280 |
| CP_01_H03 | Vh3_DP-46_(3-30.3) | Vlambda6_6a | AIRVSGTPENGF......DV | QSYHSSNL......WV | 151902 | 590 |
| CP_01_G08 | Vh6_DP-74_(6-1) | Vk2_DPK16_(A23) | VRITHGM......DV | MQATHFP......QT | 137502 | 736 |
| CP_01_A06 | Vh3_DP-49_(3-30.5) | Vk4_DPK24_(B3) | GKLAF......DI | QQYYSTP......YT | 136525 | 354 |
| CP_02_A04 | Vh3_DP-49_(3-30.5) | Vlambda6_6a | NGDSGYHTSPNWYF......XL | QSYDDSNY......WV | 130318 | 385 |
| CP_02_E08 | Vh3_DP-49_(3-30.5) | Vlambda2_2c | VSTDSSSM......DV | SSYAGSNTL......FV | 126690 | 545 |
| CP_01_G07 | Vh3_DP-49_(3-30.5) | Vk1_DPK6_(L19) | TSQDPGAF......DI | QQANSFP......LT | 117913 | 270 |
| CP_01_D01 | Vh3_DP-49_(3-30.5) | Vlambda6_6a | AESGVYSSNGM......DV | QSYDSSI......WV | 116603 | 204 |
| CP_02_A07 | Vh3_DP-50_(3-33) | Vlambda6_6a | VDRVRSGM......DV | QSYDSIH......WV | 105730 | 496 |
| CP_02_B08 | Vh3_DP-49_(3-30.5) | Vlambda6_6a | IGQYCSSTSCYM......DV | QSYDSSTH......WV | 96003 | 795 |
| CP_02_D09 | Vh3_DP-49_(3-30.5) | Vk1_DPK1_(O18, O8) | DLGGSGGAF......DI | QQYDNLP......LT | 92079 | 282 |
| CP_01_G07 | Vh3_DP-49_(3-30.5) | Vlambda6_6a | DSDAGYF......DL | QSFTSSTL......YV | 77222 | 313 |
| CP_01_A05 | Vh3_DP-49_(3-30.5) | Vk3_DPK21_(L2) | ASIVASGAF......DI | QQYNKWP......LT | 75698 | 705 |
| CP_02_A08 | Vh3_DP-49_(3-30.5) | Vlambda6_6a | AGGSNAF......DI | QSYDDSNY......WV | 73410 | 295 |
| CP_02_D07 | Vh3_DP-49_(3-30.5) | Vlambda6_6a | VSTDSYGRQNWF......DP | QSYDSSNH......WV | 72274 | 367 |
| CP_01_C04 | Vh3_DP-49_(3-30.5) | Vk1_DPK9_(O12, O2) | QYTSGRLAYYYHYM......DV | QSYSTP......RT | 65702 | 286 |
| CP_01_A07 | Vh1_DP-8, 75_(1-02) | Vlambda3_DPL16_(31) | GIRGAF......DI | NSRDSSGNPN......WV | 63917 | 238 |
| CP_01_H02 | Vh3_DP-49_(3-30.5) | Vlambda6_6a | VGYSTTQL......DY | QSYDSSNL......WV | 63410 | 266 |
| CP_01_F10 | Vh3_DP-49_(3-30.5) | Vlambda6_6a | MAGSYAF......DI | QSYDSSNH......WV | 58027 | 372 |

TABLE 1-continued

| Clone ID | VH germline ID | VL germline ID | Heavy CDR3 | Light CDR3 | TRBC1 binding | TRBC2 Binding |
|---|---|---|---|---|---|---|
| CP_02_C10 | Vh3_DP-49_(3-30.5) | Vlambda1_DPL2_(1c) | VGDYYDSSGYLDWYF........DL | AVWDDRLNG........WV | 53460 | 488 |
| CP_02_B05 | Vh3_DP-49_(3-30.5) | Vk1_L12 | GSDTTSFVS........DY | QQYDSYS........LT | 51480 | 315 |
| CP_01_G04 | Vh3_DP-49_(3-30.5) | Vlambda3_3p | AGHYYYYM........DV | QSADSSGTN........MV | 50811 | 354 |
| CP_01_F08 | Vh3_DP-49_(3-30.5) | Vlambda6_6a | VTGYPDYDSSGF........DY | QSYDSSNH........WV | 43115 | 562 |
| CP_01_G05 | Vh3_DP-49_(3-30.5) | Vlambda6_6a | VEGGPPYYF........DY | QSYDTRNQ........WV | 42289 | 409 |
| CP_02_A03 | Vh3_DP-49_(3-30.5) | Vk4_DPK24_(B3) | NGLDNYGM........DH | QQYYSTP........YT | 39382 | 322 |
| CP_01_B09 | Vh5_DP-73_(5-51) | Vk1_DPK9_(O12, O2) | LGTTKRAF........DI | QQSYST........RT | 38766 | 803 |
| CP_01_A10 | Vh3_DP-49_(3-30.5) | Vlambda1_DPL3_(1g) | VYYDHEGM........DV | AAWDDSLF........WL | 38613 | 298 |
| CP_01_H04 | Vh3_DP-49_(3-30.5) | Vk2_DPK13_(O11, O1) | WSGSGF........DY | MQRIEFP........LT | 34030 | 305 |
| CP_01_B04 | Vh3_DP-49_(3-30.5) | Vk4_DPK24_(B3) | DFGWGGAF........DI | QQYYNTP........LI | 30975 | 348 |
| CP_02_A05 | Vh5_DP-73_(5-51) | Vlambda6_6a | WGGTQH........DY | QSYDSSI........VV | 30140 | 309 |
| CP_01_F07 | Vh3_DP-49_(3-30.5) | Vlambda6_6a | NWLLYYGDPQQNAF........DV | QSYDSTNL........WV | 29443 | 331 |
| CP_01_H01 | Vh5_DP-73_(5-51) | Vk1_DPK9_(O12, O2) | LYFDWFADSQNAF........DI | QQSYSTP........LT | 26847 | 349 |
| CP_02_B07 | Vh3_DP-49_(3-30.5) | Vlambda3_DPL16_(31) | VGYQPLLYADYYF........DY | NSRDSSGNH........LV | 26520 | 360 |
| CP_01_G10 | Vh3_DP-49_(3-30.5) | Vk1_DPK9_(O12, O2) | GAMGL........DY | QQSYSTP........FT | 26087 | 292 |
| CP_01_G11 | Vh3_DP-49_(3-30.5) | Vlambda3_DPL16_(31) | VYYLsGVHAF........DV | DSRDTRVNX........WI | 25464 | 423 |
| CP_01_G01 | Vh3_DP-49_(3-30.5) | Vk1_DPK1_(O18, O8) | TERWLQF........DY | QQYDNL........PS | 23458 | 331 |
| CP_02_A12 | Vh3_DP-49_(3-30.5) | Vk2_DPK15_(A19, A3) | NGDYAF........DY | MQALQTP........YT | 20298 | 322 |
| CP_01_H05 | Vh3_DP-49_(3-30.5) | Vlambda6_6a | ASRYSGSYHF........DY | QSYDSSN........VV | 19598 | 217 |
| CP_01_G09 | Vh3_DP-46_(3-30.3) | Vlambda2_DPL11_(2a2) | HGSQGGF........DI | SSYTSSST........LV | 18725 | 449 |
| CP_02_C02 | Vh3_DP-49_(3-30.5) | Vk2_DPK15_(A19, A3) | VGYMGGM........DV | MQALQTPP........YT | 18320 | 468 |
| CP_01_D05 | Vh3_DP-46_(3-30.3) | Vlambda6_6a | NTPGIAAAGP........DS | QSYDSTNH........WV | 17240 | 299 |
| CP_01_D08 | Vh3_DP-49_(3-30.5) | Vlambda6_6a | VGTTTVTSF........DY | QSYDSANL........WV | 16499 | 291 |
| CP_01_A11 | Vh3_DP-46_(3-30.3) | Vlambda6_6a | VGGPLNDAF........DI | QSFDENIS........WV | 13370 | 329 |
| CP_02_D08 | Vh3_DP-49_(3-30.5) | Vk3_DPK22_(A27) | HSSGGAF........DI | HQSATSP........LT | 12277 | 560 |

Where the agent is a domain antibody it may comprise 3 CDRs, i.e. either VH CDR1-CDR3 or VL CDR1-CDR3.

The agent may comprise an antibody of functional fragment thereof which comprises a variable heavy chain (VH) having the amino acid sequence shown as SEQ ID No. 1 and a variable light chain (VL) having the amino acid sequence shown as SEQ ID No. 2.

```
SEQ_ID_1 Jovi-1 VH
EVRLQQSGPDLIKPGASVKMSCKASGYTFTGYVMHWWKQRPGQGLEWIG
FINPYNDDIQSNERFRGKATLTSDKSSTTAYMELSSLTSEDSAVYYCAR
GAGYNFDGAYRFFDFWGQGTTLTVSS SEQ_ID_2 Jovi-1 VL
DVVMTQSPLSLPVSLGDQASISCRSSQRLVHSNGNTYLHWYLQKPGQSP
KLLIYRVSNRFPGVPDRFSGSGSGTDFTLKISRVEAEDLGIYFCSQSTH
VPYTFGGGTKLEIKR
```

The agent may comprise an ScFv having the amino acid sequence shown as SEQ ID No. 3.

```
SEQ_ID_3 Jovi-1 scFv
EVRLQQSGPDLIKPGASVKMSCKASGYTFTGYVMHWVKQRPGQGLEWIG
FINPYNDDIQSNERFRGKATLTSDKSSTTAYMELSSLTSEDSAVYYCAR
GAGYNFDGAYRFFDFWGQGTTLTVSSGGGGSGGGGSGGGGSDVVMTQSP
LSLPVSLGDQASISCRSSQRLVHSNGNTYLHWYLQKPGQSPKLLIYRVS
NRFPGVPDRFSGSGSGTDFTLKISRVEAEDLGIYFCSQSTHVPYTFGGG
TKLEIKR
```

Alternatively, the agent may comprise an antibody or functional fragment thereof which comprises:
(i) the heavy chain CDR3 and/or the light chain CDR3;
(ii) heavy chain CDR1, CDR2 and CDR3 and/or light chain CDR1, CDR2 and CDR3; or
(iii) the variable heavy chain (VH) and/or the variable light chain (VL);
from one of the scFvs shown as SEQ ID No. 13-22.

In the sequences shown as SEQ ID No. 13-22, the VH and VL portions of the sequence are shown in bold and the CDR1 and CDR2 sequences for the heavy and light chains are underlined. The CDR3 sequences for VH and VL are given in Table 1.

```
SEQ ID No. 13_(CP_01_E09)
QVQLVESGGGVVQPGRSLRLSCAASGFTFSSYAMHWVRQAPGKGLEWVAVI
SYDGSNKYYADSVKGRFTISRDNSKNTLYLQMNSLRAEDTAVYYCARAHNS
SSWSFDYWGQGTLVTVSSGGGGSGGGGSGGGASDIQMTQSPSSLSASVGDR
VTITCRASQSISSYLNWYQQKPGKAPKLLIYDASNLETGVPSRFSGSGSGT
DFTFTISSLQPEDIATYYCQQYDNLPLTFGGGTKVDIKRTAAA

SEQ ID No. 14 (CP_01_D12)
EVQLLESGGGVVQPGRSLRLSCAASGFTFSSYAMHWVRQAPGKGLEWVAVI
SYDGSNKYYADSVKGRFTISRDNSKNTLYLQMNSLRAEDTAVYYCAKGGDT
YGFLDNWGQGTMVTVSSGGGGSGGGGSGGGASDIQMTQSPSTLSASVGDRV
TITCRASQSISSWLAWYQQKPGKAPKLLIYKASSLESGVPSRFSGSGSGTD
FTLTISSLQPEDFATYYCQQFNAYPLTFGGGTKVEIKRTAAA

SEQ ID No. 15 (CP_01_D10)
QVQLVESGGGLVQPGRSLRLSCAASGFTFSSYAMHWVRQAPGKGLEWVAVI
SYDGSSKYYADSVKGRFTISRDNSKNTLYLQMNSLRAEDTAVYYCAKGGGS
FGAFDIWGQGTLVTVSSGGGGSGGGGSGGGASDIQMTQSPSSLSASVGDRV
TITCRASQSISRYLNWYQQKPGKAPNLLIYAASSLQSGVPSRFSGSGSGTD
FTLTISSLQPEDFATYYCQQYNSYPLTFGGGTKLEIKRTAAA

SEQ ID No. 16 (CP_01_C08)
EVQLLESGGGAVQPGRSLRLSCAASGFTFSSYAMHWVRQAPGKGLEWVAVI
SYDGSNKYYADSVKGRFTISRDNSKNTLYLQMNSLRAEDTAVYYCASGYSS
SWYLDYWGQGTLVTVSSGGGGSGGGGSGGGASDIQMTQSPSSVSASVGDRV
TITCQASQDISNYLNWYQQKPGKAPKLLIYDASNLETGVPSRFSGSGSGTD
FTFTISSLQPEDIATYYCQQYDNLPLTFGGGTKVEIKRTAAA

SEQ ID No. 17(CP_01_C11)
QVQLVESGAEVKKPGASVKVSCKASGYTFTGYYMHWVRQAPGQGLEWMGRI
NPNSGGTNYAQKFQGRVTMTRDTSISTAYMELSRLRSDDTAVYYCASGGAG
WNWGQGTMVTVSSGGGGSGGGGSGGGASNFMLTQPHSVSESPGKTATISCT
RSSGSIASNYVQWYQQRPGSAPTTVIYEDNQRPFGVPDRFSGSIDSSSNSA
SLTISGLKTEDEADYYCQSHDSSNVVFGGGTQLTVLGQPAA

SEQ ID No. 18 (CP_01_F03)
EVQLVESGGGVVQPGRSLRLSCAASGFTFSSYAMHWVRQAPGKGLEWVAVI
SYDGSNKYYADSVKGRFTISRDNSKNTLYLQMNSLRAEDTAVYYCARGY?A
SSWSQGLWGQGTLVTVSSGGGGSGGGGSGGGASDIQMTQSPSSLSASVRDR
VTITCQASQDISNYLNWYQQKPGKAPKLLIYDASNLETGVPSRFSGSGSGT
DFTFTISSLQPEDIATYYCQQYDNLPPTFGGGTKVEIKRTAAA

SEQ ID No. 19 (CP_01_E07)
QVQLVESGGGVVQPGRSLRLSCAASGFTFSSYGMHWVRQAPGKGLEWVAVI
SYDGSNKYYADSVKGRFTISRDNSKNTLYLQMNSLRAEDTAVYYCAKDLGG
SGGAFDIWGQGTLVTVSSGGGGSGGGGSGGGASDIVMTQTPHSLSVTPGQP
ASISCKSSQSLLYSDGKTYLYWYLQKPGQPPQLLIYEVSNRFSGVPDRFSG
SGSGTDFTLKISRVEAEDVGVYYCMQSIQLYTFGQGTKVDIKRTAAA

SEQ ID No. 20 (CP_01_D03)
QVQLVESGGGVVQPGRSLRLSCAAPGFTFSSYGMHWVRQAPGKGLEWVAVI
SYDGSNKYYADSVKGRFTISRDNSKNTLYLQMNSLRAEDTAVYYCARNKQY
GMDVWGQGTLVTVSSGGGGSGGGGSGGGASDIVMTQSPATLSLAPGERATL
SCRASQSVGSNLAWYQQKPGQAPSLLIYDASTRATGIPARFSGSGSGTDFT
LTISSLQSEDIAVYYCQQYHRWPLTFGGGTKVEIKRTAAA

SEQ ID No. 21 (CP_01_F06)
EVQLLESGGGVVQPGRSLRLSCAASGFTFSSYGMHWVRQAPGKGLEWVAVI
SYDGSNKYYADSVKGRFTISRDNSKNTLYLQMNSLRAEDTAVYYCAKDDGA
MRYWGQGTMVTVSSGGGGSGGGGSGGGASDIQMTQSPDSLAVSLGERATIN
CKSSQSVLYSSNNKNYLAWYQQKPGQPPKLLIYWASTRESGVPDRFSGSGS
GTDFTLTISSLQAEDVAVYYCQQYYDSPYTFGQGTKVDIKRTAAA
```

-continued

SEQ ID No. 22 (CP_01_F02)
QVQLVESGGGVVQPGRPLRLSCAASGFTFSSYAMHWVRQAPGKGLEWVAVI
SYDGSNKYYADSVKGRFTISRDNSKNTLYLQMNSLRAEDTAVYYCARAGYS
YADYWGQGTMVTVSSGGGGSGGGGSGGGASDIQMTQSPSSLSASVGDRVTI
TCRASQGIRNDLGWYQQKPGKAPKRLIYAASSLQSGVPSRFSGSGSGTEFT
LTISSLQPEDFATYYCLQHNSYPLTFGGGTKVDIKRTAAA

TRBC2-Specific

Using phage display, several antibody binding domains have been identified which are highly selective for binding TRBC2 over TRBC1, as described in Example 12.

The agent may comprise an antibody or a functional fragment thereof having a variable heavy chain (VH) and/or a variable light chain (VL) which comprises one or more of the complementarity determining regions (CDR3s) shown in the Table 2.

TABLE 2

| Clone ID | VH dp number | VL dp number | CDR3 group | Heavy CDR3 | | CDR3 group | Light CDR3 | | TRBC2 binding | TRBC1 Binding |
|---|---|---|---|---|---|---|---|---|---|---|
| CP_03_E05 | Vh3_DP-47_(3-23) | Vlambda6_6a | 38 | TRSSGAF | DI | 11 | HSYDSNH | SV | 217270 | 1617 |
| CP_03_D05 | Vh1_DP-8, 75_(1-02) | Vlambda3_DPL23_(3r) | 33 | PRGRGSAF | DI | 27 | QAWDTNLG | G | 212721 | 762 |
| CP_03_H06 | Vh3_DP-35_(3-11) | Vlambda6_6a | 20 | ARVGM | DV | 19 | QSFDADNLH | V | 167971 | 391 |
| CP_03_C12 | Vh1_DP-8, 75_(1-02) | Vk2_DPK12_(A2) | 27 | DTGPI | DY | 5 | MQGIQLP | PT | 167371 | 789 |
| CP_03_G02 | Vh1_DP-7_(1-46) | Vk1_DPK9_(O12, O2) | 10 | GVWNSGSYLGF | D | 30 | QQSYSTP | LT | 151586 | 787 |
| CP_03_D04 | Vh3_DP-46_(3-30.3) | Vlambda6_6a | 28 | GGFTVPGGAF | DI | 13 | QSYDASN | VI | 143051 | 1210 |
| CP_03_F10 | Vh1_DP-8, 75_(1-02) | Vlambda2_2c | 42 | FGERYAF | DI | 9 | SAYTGSN | YV | 139767 | 1683 |
| CP_03_G09 | Vh6_DP-74_(6-1) | Vlambda3_3j | 34 | DQWLANYYYYGM | | 34 | QVWDSNS | W | 138659 | 979 |
| CP_03_F09 | Vh1_DP-7_(1-46) | Vlambda6_6a | 8 | NRGGSYKSVGM | D | 36 | QSYDEVS | VV | 131852 | 889 |
| CP_03_D09 | Vh1_DP-15_(1-08) | Vlambda6_6a | 11 | VSSYYGM | DV | 28 | QSYNSSNH | W | 128690 | 544 |
| CP_03_F02 | Vh1_DP-15_(1-08) | Vlambda6_6a | 3 | APASSAH | DH | 14 | QSYDSSH | VV | 127081 | 1507 |
| CP_02_E03 | Vh3_DP-46_(3-30.3) | Vk1_DPK9_(O12, O2) | 16 | QRGYYYGM | DV | 12 | QQSRSTP | LT | 122650 | 1979 |
| CP_03_H07 | Vh3_DP-31_(3-09) | Vlambda2_DPL11_(2a2) | 14 | SSVAAGAF | DI | 22 | SSYTSSST | WV | 120948 | 1233 |
| CP_03_C02 | Vh5_DP-73_(5-51) | Vlambda2_DPL10_(2b2) | 13 | LSGRGLGF | DY | 10 | SSYAGSNL | WV | 100238 | 1904 |
| CP_03_D08 | Vh1_DP-8, 75_(1-02) | Vlambda2_DPL11_(2a2) | 5 | DHYF | DY | 21 | NSYTRSST | LV | 99580 | 1011 |
| CP_03_E09 | Vh3_DP-46_(3-30.3) | Vlambda6_6a | 19 | SGRRVTAI | DY | 8 | QSYDDTN | VV | 92074 | 453 |
| CP_03_E11 | Vh1_DP-8, 75_(1-02) | Vlambda3_3h | 37 | MGRYSSSW | NI | 3 | QAWDTNIG | G | 91813 | 940 |
| CP_03_B05 | Vh5_DP-73_(5-51) | Vlambda2_DPL10_(2b2) | 12 | HSRFGPAF | DI | 23 | SSYAGSNN | YV | 88004 | 815 |
| CP_03_H02 | Vh1_DP-8, 75_(1-02) | Vlambda3_DPL23_(3r) | 25 | DREAF | DI | 3 | QAWDTNIG | G | 87576 | 1829 |
| CP_03_D02 | Vh5_DP-73_(5-51) | Vlambda2_DPL10_(2b2) | 7 | LRGRYSYGYSDAF | D | 17 | SSYAGSST | FV | 84907 | 1096 |
| CP_03_E01 | Vh1_DP-8, 75_(1-02) | Vlambda3_DPL16_(31) | 36 | LLNAVTYAF | DI | 4 | NSRDSSGF | PV | 81606 | 498 |
| CP_03_C11 | Vh1_DP-8, 75_(1-02) | Vlambda2_DPL11_(2a2) | 2 | IGVIGGF | DY | 18 | SSYTSSS | IL | 78572 | 1079 |
| CP_03_B12 | Vh3_DP-47_(3-23) | Vlambda6_6a | 9 | IEYSSSSPYF | DY | 16 | QSYDSNNR | VL | 70734 | 1120 |
| CP_03_E03 | Vh1_DP-7_(1-46) | Vlambda3_DPL16_(31) | 18 | DLLPTTVTTTGAF | DI | 7 | SSRDSSGNH | LV | 69661 | 356 |

TABLE 2-continued

| Clone ID | VH dp number | VL dp number | CDR3 group | Heavy CDR3 | | CDR3 group | Light CDR3 | | TRBC2 binding | TRBC1 Binding |
|---|---|---|---|---|---|---|---|---|---|---|
| CP_03_F01 | Vh1_DP-8, 75_(1-02) | Vlambda3_DPL23_(3r) | 40 | DSGSYS................ | .DY | 3 | QAWDTNIG........ | .G | 66921 | 1633 |
| CP_03_C01 | Vh6_DP-74_(6-1) | Vlambda3_3j | 31 | ASYPYYYYYGM........... | .D | 29 | QVWDSSTAN....... | . | 58194 | 825 |
| CP_03_G07 | Vh6_DP-74_(6-1) | Vlambda6_6a | 41 | ALGHF................. | .DF | 32 | QSYDSSNHH....... | .V | 57147 | 1278 |
| CP_03_E02 | Vh5_DP-73_(5-51) | Vlambda2_DPL11_(2a2) | 35 | FTTGSAL............... | .YM | 26 | SSYAGNSN........ | .LV | 52212 | 362 |
| CP_03_C07 | Vh1_DP-8, 75_(1-02) | Vlambda3_DPL23_(3r) | 17 | DASGY................. | .DY | 3 | QAWDTNIG........ | .G | 43547 | 1074 |
| CP_03_H04 | Vh1_DP-8, 75_(1-02) | Vlambda1_DPL5_(1b) | 39 | DLGTYYGSGD............ | .DY | 2 | GTWDSSLSAG...... | .Q | 35180 | 1103 |
| CP_03_E06 | Vh1_DP-8, 75_(1-02) | Vlambda3_DPL16_(31) | 15 | VGELLGAF.............. | .DI | 35 | SSLDSNDNH....... | .PI | 34777 | 917 |
| CP_03_H03 | Vh1_DP-5_(1-24) | Vlambda1_DPL2_(1c) | 23 | GL.................... | .GV | 37 | AAWDDSLNG....... | .Y | 33358 | 1405 |
| CP_03_G11 | Vh5_DP-73_(5-51) | Vlambda2_DPL12_(2e) | 4 | HSGVGGLAF............. | .DI | 31 | SSYAGSST........ | .YV | 30854 | 836 |
| CP_03_G01 | Vh6_DP-74_(6-1) | Vk1_L9 | 30 | GGSIAAALAF............ | .DV | 20 | HQYDVYP......... | .PT | 30762 | 1039 |
| CP_03_H01 | Vh1_DP-15_(1-08) | Vlambda3_DPL16_(31) | 22 | VEYSRNGM.............. | .LI | 6 | NSRDSSGNH....... | .LV | 29826 | 1203 |
| CP_03_F11 | Vh1_DP-15_(1-08) | Vlambda6_6a | 32 | GRYN.................. | .DV | 15 | QSYDSSN......... | .WV | 24172 | 1152 |
| CP_03_C06 | Vh1_DP-14_(1-18) | Vlambda6_6a | 26 | LDYYYGM............... | .DI | 33 | QSYDSSN......... | .QV | 23031 | 937 |
| CP_03_D03 | Vh1_DP-15_(1-08) | Vlambda6_6a | 6 | GGLSSAF............... | .DV | 24 | QSYDSSN......... | .VV | 22905 | 1283 |
| CP_03_G05 | Vh5_DP-73_(5-51) | Vlambda2_DPL12_(2e) | 21 | YGGGL................. | .DY | 25 | SSYAGSYT........ | .LV | 22037 | 813 |
| CP_03_G12 | Vh3_DP-47_(3-23) | Vlambda2_DPL11_(2a2) | 24 | PDHLTVF............... | .DV | 1 | SSYTPSS......... | .VL | 20349 | 942 |
| CP_03_C10 | Vh1_DP-8, 75_(1-02) | Vlambda3_DPL23_(3r) | 29 | VGYYGM................ | .DV | 3 | QAWDTNIG........ | .G | 18438 | 896 |
| CP_03_F04 | Vh1_DP-8, 75_(1-02) | Vlambda3_DPL23_(3r) | 29 | YEGYAGF............... | .DY | 3 | QAWDTNIG........ | .G | 13541 | 1047 |

The agent may comprise an antibody or functional fragment thereof which comprises:

(i) the heavy chain CDR3 and/or the light chain CDR3;
(ii) Heavy chain CDR1, CDR2 and CDR3 and/or light chain CDR1, CDR2 and CDR3; or
(iii) the variable heavy chain (VH) and/or the variable light chain (VL); from one of the scFvs shown as SEQ ID No. 23-32.

In the sequences shown as SEQ ID No. 23-32, the VH and VL portions of the sequence are shown in bold and the CDR1 and CDR2 sequences for the heavy and light chains are underlined. The CDR3 sequences for VH and VL are given in Table 2.

```
SEQ ID No. 23 (CP_03_E05)
EVQLVESGGGVVQPGGSLRLSCAASGFTFSSYAMSWVRQAPGKGLEWVSAI
SGSGGSTYYADSVKGRFSISRDNSKNTLYLQMNSLRAEDTAVYYCARTRSS
GAFDIWGQGTLVTVSSGGGGSGGGGSGGGASNFMLTQPHSVSESPGKTVTI
SCTRSSGSIASKYVQWYQQRPGSSPTTVIYEDNQRPSGVPDRFSGSIDTSS
NSASLTISGLRTEDEADYYCHSYDSNNHSVFGGGTKVTVLGQPAA

SEQ ID No. 24 (CP_03_D05)
QVQLVESGAEVKKPGASVKVSCKASGYTFTGYYMHWVRQAPGQGLEWMGRI
NPNSGGTNYAQKFQGRVTMTRDTSISTAYMELSRLRSDDTAVYYCASPRGR
GSAFDIWGQGTLVTVSSGGGGSGGGGSGGGASSYELTQPPSVSVSPGQTAT
ISCSGDQLGGKYGHWYQKKPGQSPVLVLYQDRKRPAGIPERFSGSSSGNTI
TLTISGTQAVDEADYYCQAWDTNLGGVFGGGTKVTVLGQPAA

SEQ ID No. 25 (CP_03_H06)
QVQLVESGGGLVKPGGSLRLSCAASGFTFSDYYMSWIRQAPGKGLEWVSYI
SSSGSTIYYADSVEGRFTISRDNAKNSLYLQMNSLRTEDTAVYYCARARVG
GMDVWGQGTMVTVSSGGGGSGGGGSGGGASNFMLTQPHSVSESPGKTVTIS
CTRSSGSIASNYVQWYQQRPGSSPTTVIYEDNQRPSGVPDRFSGSIDSSSN
SASLTISGLKTEDEADYYCQSFDADNLHVVFGGGTKLTVLGQPAA

SEQ ID No. 26 (CP_03_C12)
EVQLVQSGAEVKKPGASVKVSCKASGYTFTGYYMHWVRQAPGQGLEWMGWI
NPNSGGTNYAQKFQGRVTMTRDTSISTAYMELSSLRSEDTAVYYCARDTGP
IDYWGQGTMVTVSSGGGGSGGGGSGGGASDIVMTQTPLSLSVTPGQPASIS
CKSSQSLLHSDGKTYLYWYLQKPGQPPQLLVYEVSNRFSGVPDKFSGSGSG
TDFTLKISRVEAEDVGVYYCMQGIQLPPTFGGGTKVDIKRTAAA

SEQ ID No. 27 (CP_03_G02)
EVQLVQSGAEVKKPGSSVKVSCKASGGTFSSYAISWVRQAPGQGLEWMGII
NPSGGSTSYAQKFQGRVTMTRDTSTSIVYMELSSLRSEDTAVYYCARGVWN
SGSYLGFDYWGQGTLVTVSSGGGGSGGGGSGGGASDIQMTQSPSSLSASVG
DRVTITCQASQDISNYLNWYQQKPGKAPKLLIYAASSLQSGVPSRFSGSGS
GTDFTLTISSLQPEDFATYYCQQSYSTPLTFGGGTKLEIKRTAAA

SEQ ID No. 28 (CP_03_D04)
EVQLVESGGGVVQPGRSLRLSCAASGFTFSSYAMHWVRQAPGKGLEWVAVI
SYDGSNKYYADSVKGRFTISRDNSKNTLYLQMNSLRAEDTAVYYCARGGFT
VPGGAFDIWGQGTLVTVSSGGGGSGGGGSGGGASNFMLTQPHSVSDSPGKT
VTISCTRSSGRIGSNFVQWYQQRPGSSPTTVIYEDDQRPSGVPARFSGSID
SSSNSASLTISGLTTADEAGYYCQSYDASNVIFGGGTKLTVLGQPAA

SEQ ID No. 29 (CP_03_F10)
EVQLVESGAEVKKPGASVKVSCKASGYTFTGYYMHWVRQAPGQGLEWMGRI
NPNSGGTNYAQKFQGRVTMTRDTSISTAYMELSSLRSEDTAVYYCARFGER
YAFDIWGQGTLVTVSSGGGGSGGGGSGGGASQSELTQPPSASGSPGQSVTI
SCTGTSTDVGAFHFVSWYQHTPGKAPKLLISEVRKRASGVPDRFSGSRSGN
TASLTVSGLQSEDEADYFCSAYTGSNYVFGSGTKLTVLGQPAA

SEQ ID No. 30 (CP_03_G09)
QVQLQQSGPGLVKPSQTLSLTCAISGDSVSSNSAAWNWIRQSPSRGLEWLG
RTYYRSKWYNDYAVSVKSRITINPDTSKNQFSLQLNSVTPEDTAVYYCARD
QWLANYYYGMDVWGQGTLVTVSSGGGGSGGGGSGGGASSYELTQPLSVSV
ALGQTARITCGGNNIGSKNVHWYQQKPGQAPVLVIYRDNNRPSGIPERFSG
SNSGNTATLTISKAQAGDEADYYCQVWDSNSWVFGGGTKLTVLGQPAA

SEQ ID No. 31 (CP_03_F09)
QMQLVQSGAEVKKPGASVKVSCKASGYTFASYYMHWVRQAPGQGLEWMGII
NPSGGSTSYAQKFQGRVTMTRDTSTSTVYMELSRLRSDDTAVYYCASNRGG
SYKSVGMDVWGQGTTVTVSSGGGGSGGGGSGGGASNFMLTQPQSVSESPGK
TVTISCTRSSGNFASKYVQWYQQRPGSSPTTVIYENYQRPSGVPDRFSGSI
DSSSNSATLTISGLKTEDEADYYCQSYDEVSVVFGGGTQLTVLGQPAA

SEQ ID No. 32 (CP_03_D09)
EVQLVQSGAEVKKPGSSVKVSCEASGYTFTSYAISWVRQAPGQGLEWMGWM
NPNSGNTGYAQKFQGRVTMTRNTSISTAYMELSSLRSEDTAVYYCARVSSY
YGMDVWGQGTLVTVSSGGGGSGGGGSGGGASNFMLTQPLSVSESPGKTVTI
SCTRSSGSIASNYVQWYQQRPGSAPTTVIYEDNQRPSGVPDRFSGSIDSSS
NSASLTISGLKTEDEADYYCQSYNSSNHWVFGGGTKVTVLGQPAA
```

Variants of the above amino acid sequences may also be used in the present invention, provided that the resulting antibody binds TRBC1 or TRBC2 and does not significantly cross-react. Typically such variants have a high degree of sequence identity with one of the sequences specified above.

Methods of alignment of sequences for comparison are well known in the art.

The NCBI Basic Local Alignment Search Tool (BLAST) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Variants of the VL or VH domain or scFv typically have at least about 75%, for example at least about 80%, 90%, 95%, 96%, 97%, 98% or 99% sequence identity with the sequences given as SEQ ID Nos 1-3, 13-32.

Typically variants may contain one or more conservative amino acid substitutions compared to the original amino acid or nucleic acid sequence. Conservative substitutions are those substitutions that do not substantially affect or decrease the affinity of an antibody to bind TRBC1 or TRBC2. For example, a human antibody that specifically binds TRBC1 or TRBC2 may include up to 1, up to 2, up to 5, up to 10, or up to 15 conservative substitutions in either or both of the VH or VL compared to any of the sequences given as SEQ ID No. 1-3 or 13-32 and retain specific binding to TRBC1 or TRBC2.

Functionally similar amino acids which may be exchanged by way of conservative substitution are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Preparation of Antibodies

Preparation of antibodies may be performed using standard laboratory techniques. Antibodies may be obtained from animal serum, or, in the case of monoclonal antibodies or fragments thereof, produced in cell culture. Recombinant DNA technology may be used to produce the antibodies according to established procedure, in bacterial or mammalian cell culture.

Methods for the production of monoclonal antibodies are well known in the art. Briefly, monoclonal antibodies are typically made by fusing myeloma cells with the spleen cells from a mouse or rabbit that has been immunized with the desired antigen. Herein, the desired antigen is TRBC1 or TRBC2 peptide, or a TCRβ chain comprising either TRBC1 or TRBC2.

Alternatively, antibodies and related molecules, particularly scFvs, may be made outside the immune system by combining libraries of VH and VL chains in a recombinant manner. Such libraries may be constructed and screened using phage-display technology as described in Example 12.

Identification of TRBC1/TRBC2 Selective Antibodies

Antibodies which are selective for either TRBC1 or TRBC2 may be identified using methods which are standard in the art. Methods for determining the binding specificity of an antibody include, but are not limited to, ELISA, western blot, immunohistochemistry, flow cytometry, Förster resonance energy transfer (FRET), phage display libraries, yeast two-hybrid screens, co-immunoprecipitation, bimolecular fluorescence complementation and tandem affinity purification.

To identify an antibody which is selective for either TRBC1 or TRBC2 the binding of the antibody to each of TRBC1 and TRBC2 is assessed. Typically, this is assessed by determining the binding of the antibody to each TRBC separately. An antibody which is selective binds to either TRBC1 or TRBC2 without significant binding to the other TRBC.

Antibody Mimetics

The agent may alternatively be a molecule which is not derived from or based on an immunoglobulin. A number of "antibody mimetic" designed repeat proteins (DRPs) have been developed to exploit the binding abilities of non-antibody polypeptides.

Repeat proteins such as ankyrin or leucine-rich repeat proteins are ubiquitous binding molecules which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. DARPins (Designed Ankyrin Repeat Proteins) are one example of an antibody mimetic based on this technology.

For Anticalins, the binding specificity is derived from lipocalins, a family of proteins which perform a range of functions in vivo associated with physiological transport and storage of chemically sensitive or insoluble compounds. Lipocalins have a robust intrinsic structure comprising a highly conserved β-barrel which supports four loops at one terminus of the protein. These loops for the entrance to a binding pocket and conformational differences in this part of the molecule account for the variation in binding specificity between different lipocalins.

Avimers are evolved from a large family of human extracellular receptor domains by in vitro exon shuffling and phage display, generating multi-domain proteins with binding and inhibitory properties.

Versabodies are small proteins of 3-5 kDa with >15% cysteines which form a high disulfide density scaffold, replacing the hydrophobic core present in most proteins. The replacement of a large number of hydrophobic amino acids, comprising the hydrophobic core, with a small number of disulphides results in a protein that is smaller, more hydrophilic, more resistant to proteases and heat and has a lower density of T-cell epitopes. All four of these properties result in a protein having considerably reduced immunogenicity. They may also be manufactured in *E. coli*, and are highly soluble and stable.

Conjugates

The antibody or mimetic may be a conjugate of the antibody or mimetic and another agent or antibody, for example the conjugate may be a detectable entity or a chemotherapeutic entity.

The detectable entity may be a fluorescent moiety, for example a fluorescent peptide. A "fluorescent peptide" refers to a polypeptide which, following excitation, emits light at a detectable wavelength. Examples of fluorescent proteins include, but are not limited to, fluorescein isothiocyanate (FITC), phycoerythrin (PE), allophycocyanin (APC), green fluorescent protein (GFP), enhanced GFP, red fluorescent protein (RFP), blue fluorescent protein (BFP) and mCherry.

A selective TRBC1 or TRBC2 agent conjugated to a detectable entity may be used to determine the TRBC of a malignant T cell.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinum coordination complexes such as cisplatin and carboplatin, anthracenediones, substituted urea such as hydroxyurea, methyl hydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents;

antiandrogens such as flutamide, gonadotropin-releasing hormone analogs and leuprolide; and non-steroidal antiandrogens such as flutamide.

A TRBC selective agent conjugated to a chemotherapeutic entity enables the targeted delivery of the chemotherapeutic entity to cells which express either TRBC1 or TRBC2.

Bi-Specific T-Cell Engagers

A wide variety of molecules have been developed which are based on the basic concept of having two antibody-like binding domains.

Bispecific T-cell engaging molecules are a class of bispecific antibody-type molecules that have been developed, primarily for the use as anti-cancer drugs. They direct a host s immune system, more specifically the T cells cytotoxic activity, against a target cell, such as a cancer cell. In these molecules, one binding domain binds to a T cell via the CD3 receptor, and the other to a target cells such as a tumor cell (via a tumor specific molecule). Since the bispecific molecule binds both the target cell and the T cell, it brings the target cell into proximity with the T cell, so that the T cell can exert its effect, for example, a cytotoxic effect on a cancer cell. The formation of the T cell:bispecific Ab:cancer cell complex induces signaling in the T cell leading to, for example, the release of cytotoxic mediators. Ideally, the agent only induces the desired signaling in the presence of the target cell, leading to selective killing.

Bispecific T-cell engaging molecules have been developed in a number of different formats, but one of the most common is a fusion consisting of two single-chain variable fragments (scFvs) of different antibodies. These are sometimes known as BiTEs (Bi-specific T-cell Engagers).

The agent used in the method of the present invention may be a bi-specific molecule which selectively recognises TRBC1 or TRBC2 and is capable of activating a T cell. For example the agent may be a BiTE. The agent used in the method may comprise:

(i) a first domain which binds either TRBC1 or TRBC2; and (ii) a second domain capable of activating a T cell.

The bi-specific molecule may comprise a signal peptide to aid in its production. The signal peptide may cause the bi-specific molecule to be secreted by a host cell, such that the bi-specific molecule can be harvested from the host cell supernatant.

The signal peptide may be at the amino terminus of the molecule. The bi-specific molecule may have the general formula: Signal peptide-first domain-second domain.

The bi-specific molecule may comprise a spacer sequence to connect the first domain with the second domain and spatially separate the two domains.

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

The bi-specific molecule may comprise JOVI-1, or a functional fragment thereof, as defined above.

Chimeric Antigen Receptor (CAR)

Chimeric antigen receptors (CARs), also known as chimeric T-cell receptors, artificial T-cell receptors and chimeric immunoreceptors, are engineered receptors, which graft an arbitrary specificity onto an immune effector cell. In a classical CAR, the specificity of a monoclonal antibody is grafted on to a T-cell. CAR-encoding nucleic acids may be transferred to T-cells using, for example, retroviral vectors. In this way, a large number of cancer-specific T-cells can be generated for adoptive cell transfer. Phase I clinical studies of this approach show efficacy.

The target-antigen binding domain of a CAR is commonly fused via a spacer and transmembrane domain to an endodomain, which comprises or associates with an intercellular T-cell signalling domain. When the CAR binds the target-antigen, this results in the transmission of an activating signal to the T-cell it is expressed on.

The agent used in the method of the present invention may be a CAR which selectively recognises TRBC1 or TRBC2. The agent may be a T-cell which expresses a CAR which selectively recognises TRBC1 or TRBC2.

The CAR may also comprise a transmembrane domain which spans the membrane. It may comprise a hydrophobic alpha helix. The transmembrane domain may be derived from CD28, which gives good receptor stability.

The endodomain is the portion of the CAR involved in signal-transmission. The endodomain either comprises or associates with an intracellular T-cell signalling domain. After antigen recognition, receptors cluster and a signal is transmitted to the cell. The most commonly used T-cell signalling component is that of CD3-zeta which contains 3 ITAMs. This transmits an activation signal to the T-cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of the CAR may comprise the CD28 endodomain and OX40 and CD3-Zeta endodomain.

The CAR may comprise a signal peptide so that when the CAR is expressed inside a cell, such as a T-cell, the nascent protein is directed to the endoplasmic reticulum and subsequently to the cell surface, where it is expressed.

The CAR may comprise a spacer sequence to connect the TRBC-binding domain with the transmembrane domain and spatially separate the TRBC-binding domain from the endodomain. A flexible spacer allows to the TRBC-binding domain to orient in different directions to enable TRBC binding.

The spacer sequence may, for example, comprise an IgG1 Fc region, an IgG1 hinge or a CD8 stalk, or a combination thereof. The linker may alternatively comprise an alternative linker sequence which has similar length and/or domain spacing properties as an IgG1 Fc region, an IgG1 hinge or a CD8 stalk.

Figure 15:
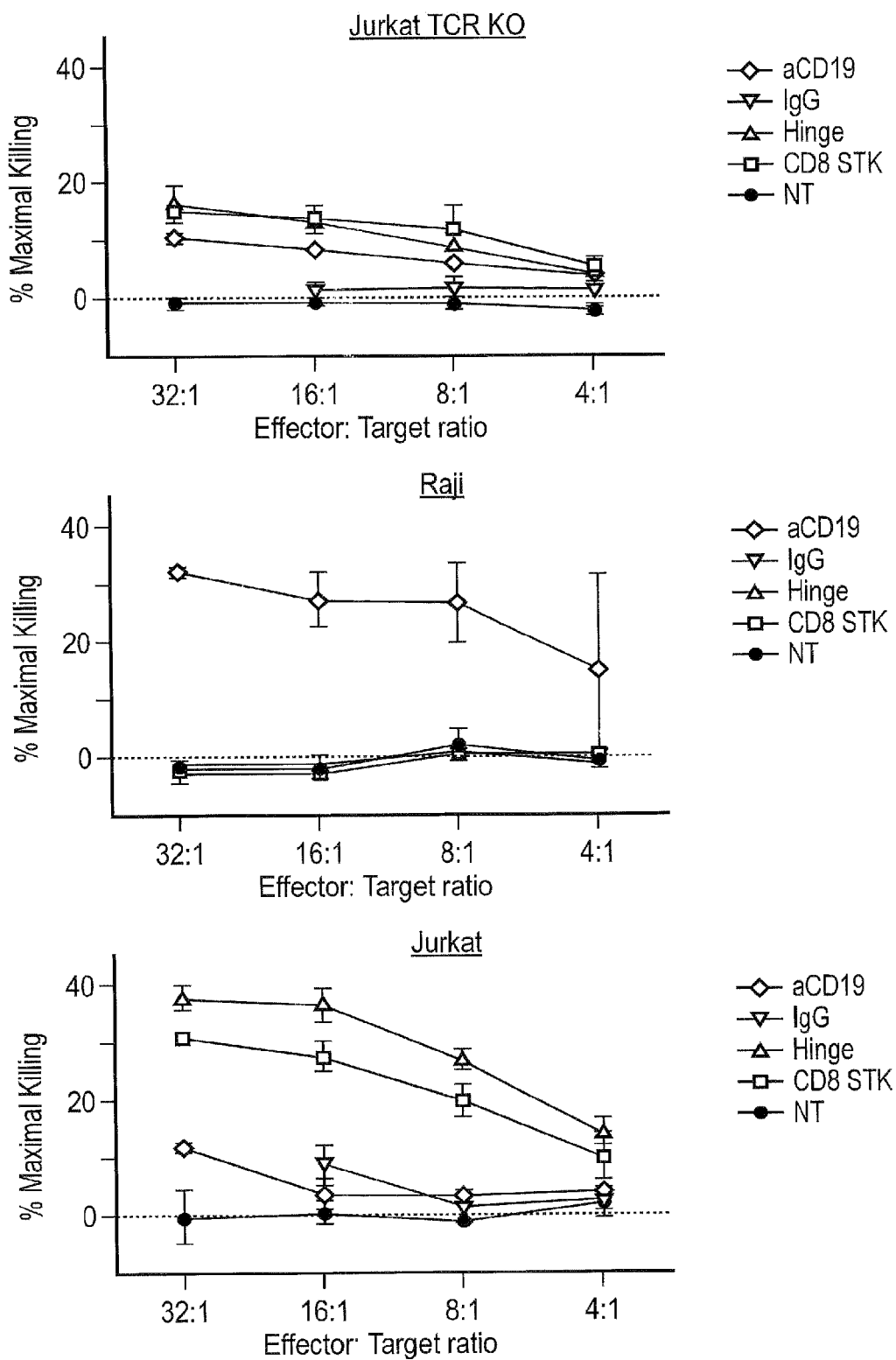
FIG. 15: Function of JOVI-1 based CAR. Normal donor peripheral blood T-cells were transduced with the different CARs described above. T-cells were also transduced with a CD19-specific CAR as a control. These T-cells were then challenged with target cells: Jurkats-TCR knock-out and Jurkats wild-type and Raji cells (a CD19+ B-cell lymphoma line). Chromium release data is shown of the effectors against different targets. JOVI-1 CAR T-cells kill Jurkats but not Raji cells or Jurkats with TCR knocked out.
Figure 16:
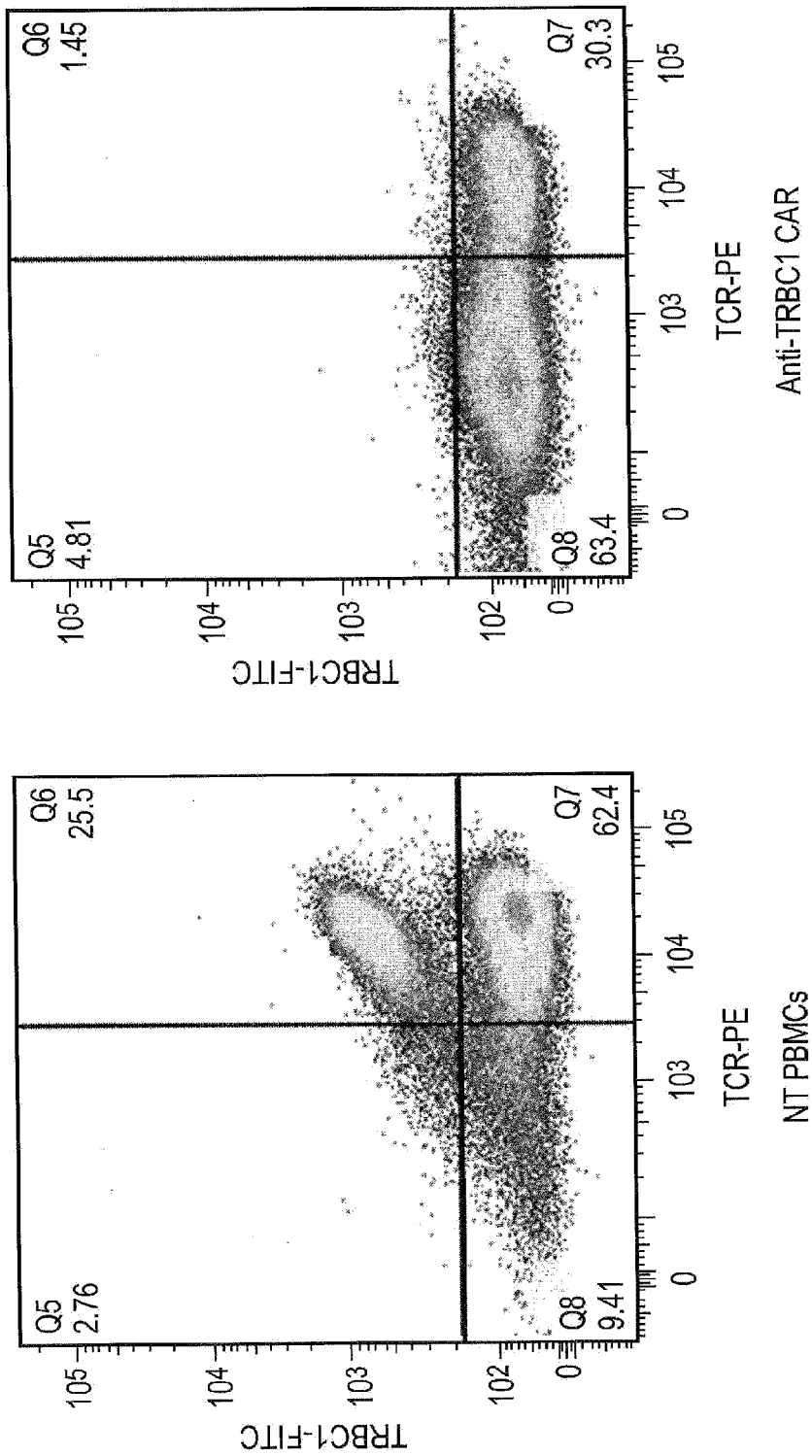
FIG. 16: Self-Purging of JOVI-1 CAR T-cell cultures. Since T-cells comprise of approximately equal numbers of T-cells which are either TRBC1 or TRBC2 positive, it is possible that after introduction of CARs a certain amount of "fratricide" or self-purging of the culture may occur. It was demonstrated that this was the case. In this example, CAR T-cells were stained after transduction and analysed by flow-cytometry. Comparing mock-transduced versus transduced, one can observe that the T-cell population loses TRBC1 positive T-cells.
Figure 17:
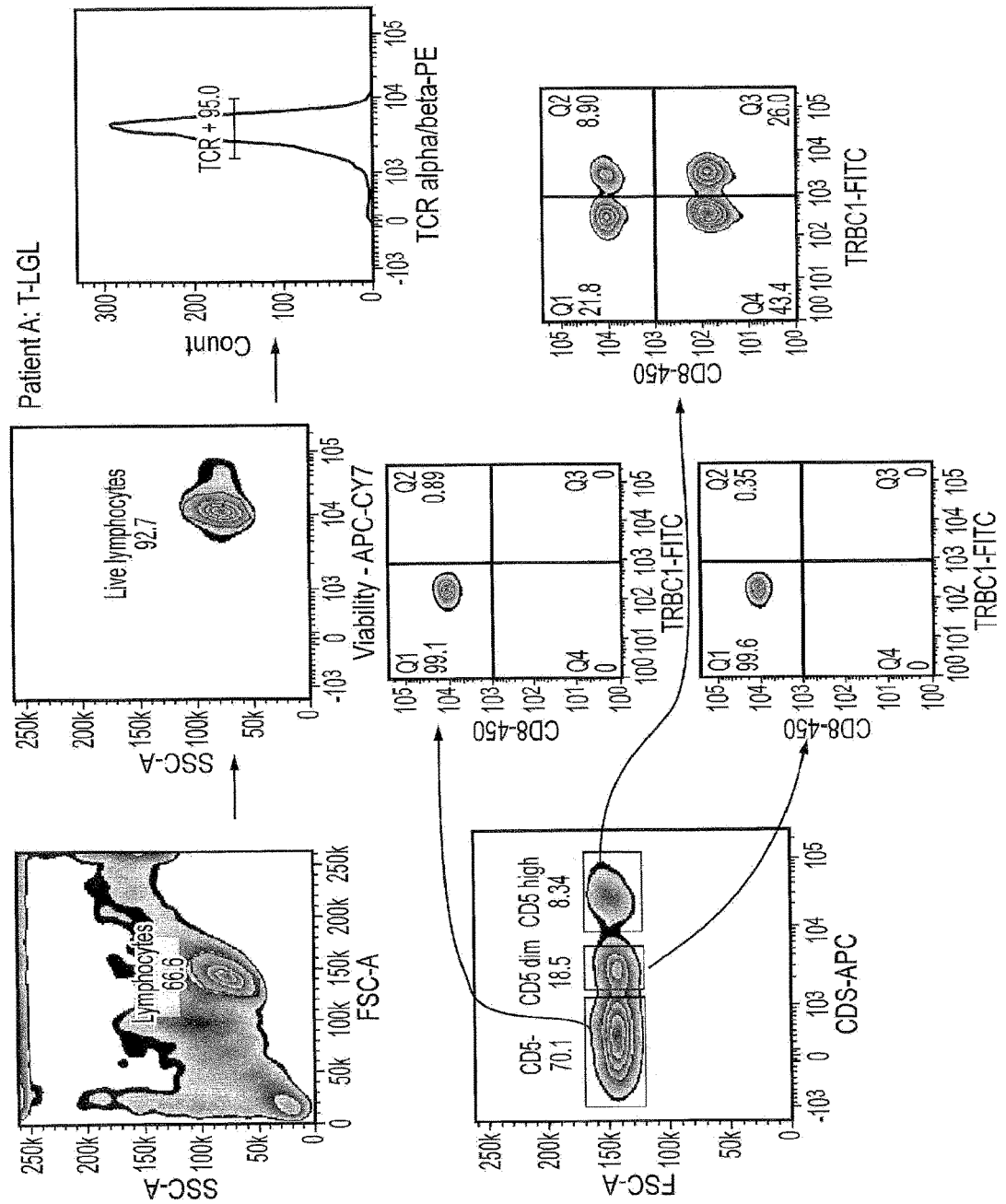
FIG. 17: Investigating the clonality of T-cell large granular Leukaemia (T-LGL)—Patient A
Figure 18:
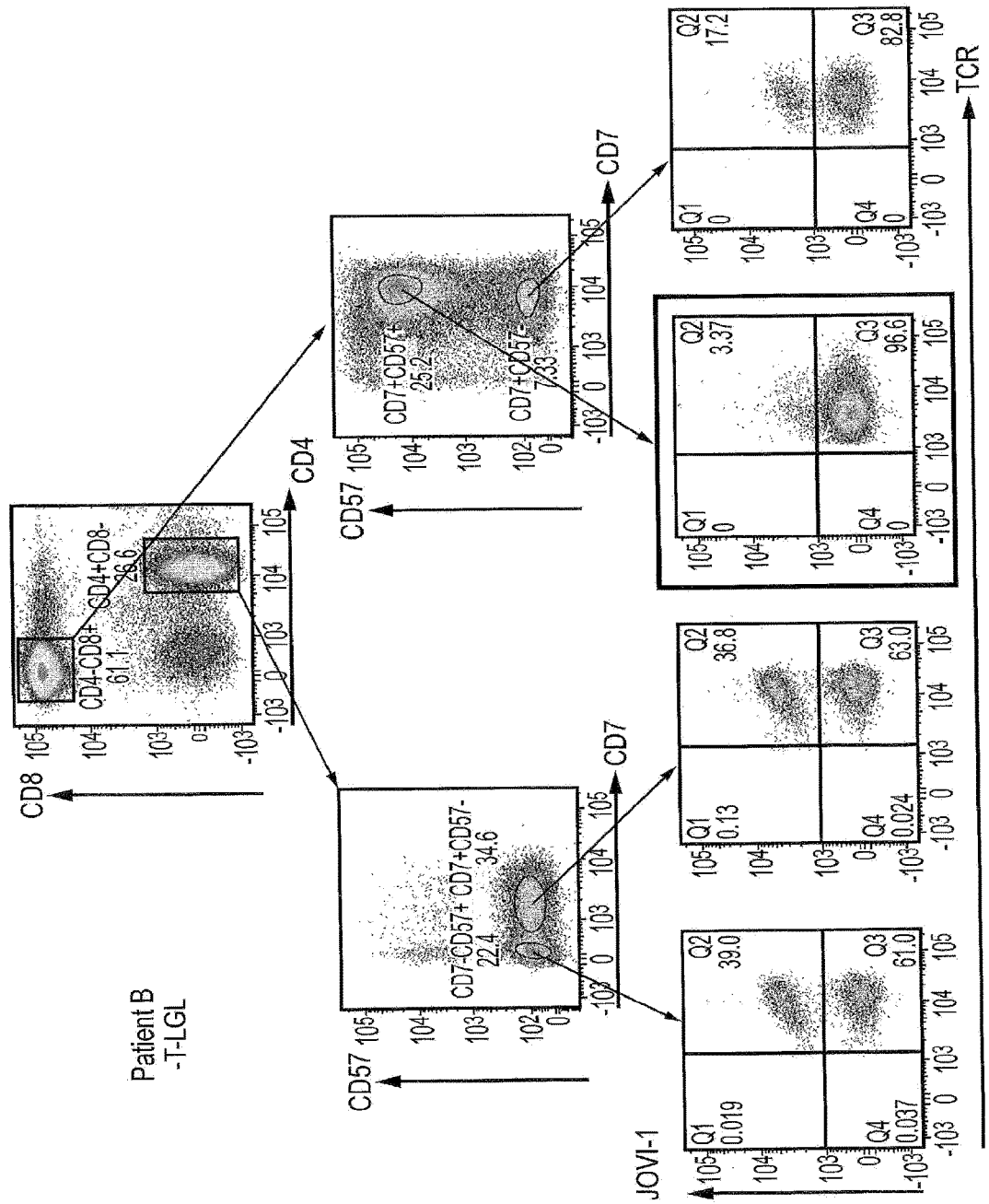
FIG. 18: Investigating the clonality of T-cell large granular Leukaemia (T-LGL)—Patient B
Figure 19:
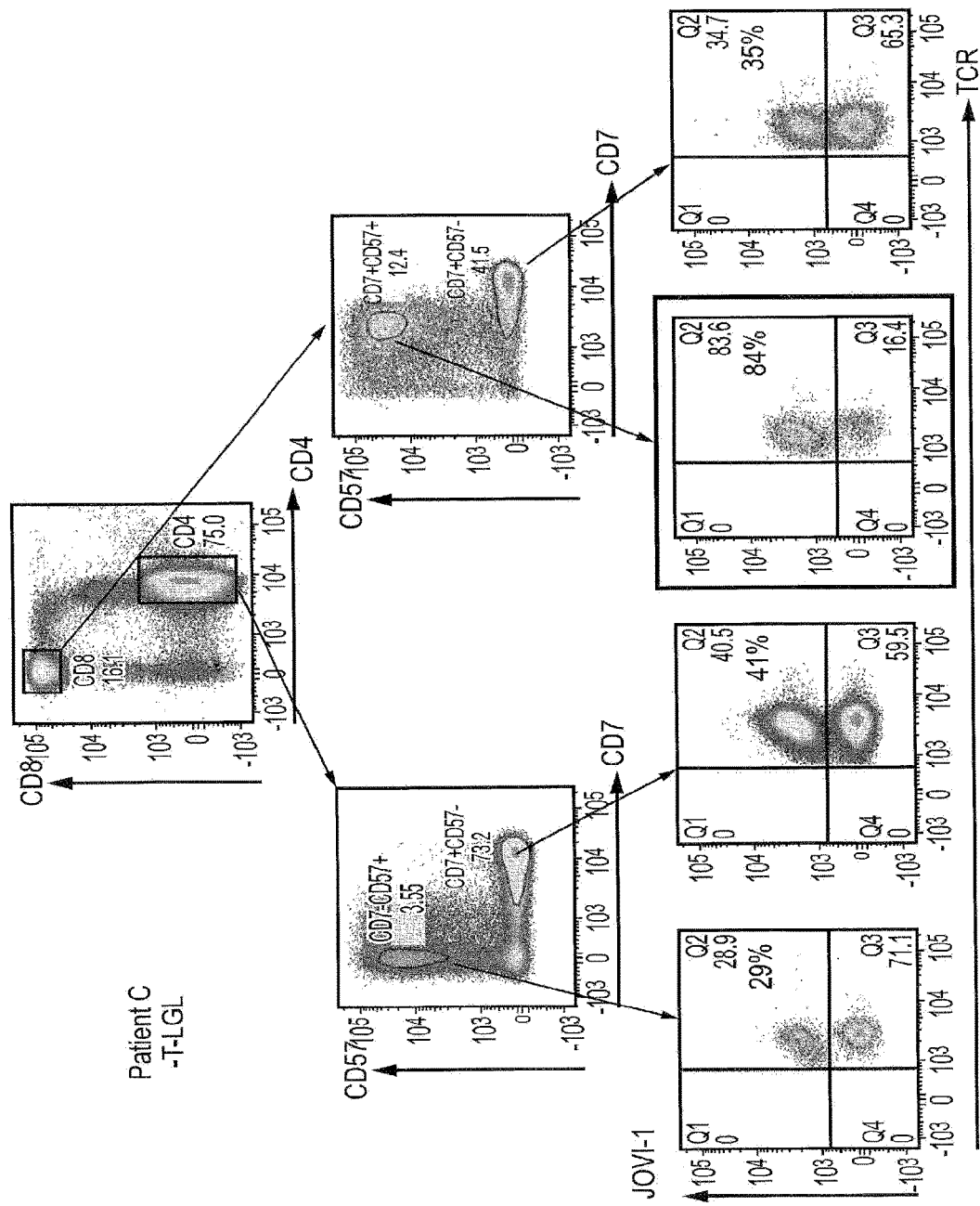
FIG. 19: Investigating the clonality of T-cell large granular Leukaemia (T-LGL)—Patient C
Figure 20:
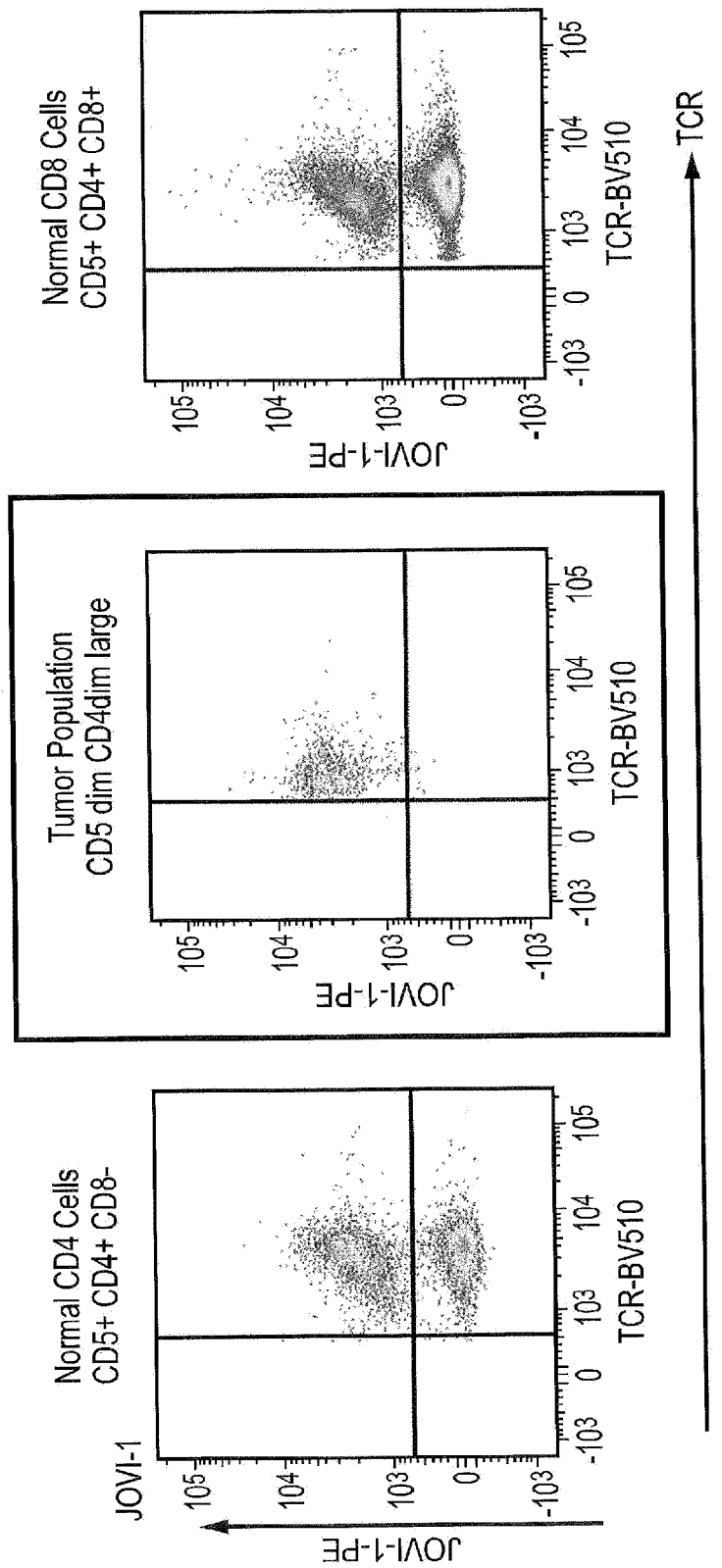
FIG. 20: Investigating the clonality of polyclonal T-cell lymphoma (PCTL)—Patient D

It was found that CARs comprising a spacer based on an IgG1 hinge or a CD8 stalk showed the best performance against Jurkat cells (FIG. 15). The spacer may an therefore comprise an IgG1 hinge or a CD8 stalk or a spacer which has a similar length and/or domain spacing properties as an IgG1 hinge or a CD8 stalk.

A human IgG1 spacer may be altered to remove Fc binding motifs.

The CAR may comprise the JOVI-1 antibody, or a functional fragment thereof, as defined above.

The CAR may comprise an amino acid sequence selected from the group consisting of SEQ ID No. 33, 34 and 35.

```
>SEQ_ID_33 JOVI-1 CAR with CD8 stalk spacer
METDTLLLWWLLVWIPGSTGEVRLQQSGPDLIKPGASVKMSCKASGYTF

TGYVMHWVKQRPGQGLEWIGFINPYNDDIQSNERFRGKATLTSDKSSTT

AYMELSSLTSEDSAVYYCARGAGYNFDGAYRFFDFWGQGTTLTVSSGGG
```

-continued
GSGGGGSGGGGSDVVMTQSPLSLPVSLGDQASISCRSSQRLVHSNGNTY

LHWYLQKPGQSPKLLIYRVSNRFPGVPDRFSGSGSGTDFTLKISRVEAE

DLGIYFCSQSTHVPYTFGGGTKLEIKRSDPTTTPAPRPPTPAPTIASQP

LSLRPEACRPAAGGAVHTRGLDFACDIFWVLVVVGGVLACYSLLVTVAF

IIFWVRSKRSRLLHSDYMNMTPRRPGPTRKHYQPYAPPRDFAAYRSRDQ

RLPPDAHKPPGGGSFRTPIQEEQADAHSTLAKIRVKFSRSADAPAYQQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

>SEQ_ID_34 JOVI-1 CAR with H-CH2-CH3pvaa spacer
METDTLLLWWLLVWIPGSTGEVRLQQSGPDLIKPGASVKMSCKASGYTF

TGYVMHWVKQRPGQGLEWIGFINPYNDDIQSNERFRGKATLTSDKSSTT

AYMELSSLTSEDSAVYYCARGAGYNFDGAYRFFDFWGQGTTLTVSSGGG

GSGGGGSGGGGSDVVMTQSPLSLPVSLGDQASISCRSSQRLVHSNGNTY

LHWYLQKPGQSPKLLIYRVSNRFPGVPDRFSGSGSGTDFTLKISRVEAE

DLGIYFCSQSTHVPYTFGGGTKLEIKRSDPAEPKSPDKTHTCPPCPAPP

VAGPSVFLFPPKPKDTLMIARTPEVTCVVVDVSHEDPEVKFNWYVDGVE

VHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGKKDPKFWVLVVVGGVLACYSLLVTVAFIIFWVR

SKRSRLLHSDYMNMTPRRPGPTRKHYQPYAPPRDFAAYRSRDQRLPPDA

HKPPGGGSFRTPIQEEQADAHSTLAKIRVKFSRSADAPAYQQGQNQLYN

ELNLGRREEYDVLDKRRGRDPEMGGKPRRKNPQEGLYNELQKDKMAEAY

SEIGMKGERRRGKGHDGLYQGLSTATKDTYDALHMQALPPR

>SEQ_ID_35 JOVI-1 CAR with IgG1 hinge spacer
METDTLLLWWLLVWIPGSTGEVRLQQSGPDLIKPGASVKMSCKASGYTF

TGYVMHWVKQRPGQGLEWIGFINPYNDDIQSNERFRGKATLTSDKSSTT

AYMELSSLTSEDSAVYYCARGAGYNFDGAYRFFDFWGQGTTLTVSSGGG

GSGGGGSGGGGSDVVMTQSPLSLPVSLGDQASISCRSSQRLVHSNGNTY

LHWYLQKPGQSPKLLIYRVSNRFPGVPDRFSGSGSGTDFTLKISRVEAE

DLGIYFCSQSTHVPYTFGGGTKLEIKRSDPAEPKSPDKTHTCPPCPKDP

KFWVLVVVGGVLACYSLLVTVAFIIFWVRSKRSRLLHSDYMNMTPRRPG

PTRKHYQPYAPPRDFAAYRSRDQRLPPDAHKPPGGGSFRTPIQEEQADA

HSTLAKIRVKFSRSADAPAYQQGQNQLYNELNLGRREEYDVLDKRRGRD

PEMGGKPRRKNPQEGLYNELQKDKMAEAYSEIGMKGERRRGKGHDGLYQ

GLSTATKDTYDALHMQALPPR

In the CAR sequences given above, one or more of the 6 CDRs each independently may or may not comprise one or more amino acid mutations (eg substitutions) compared to the sequences given as SEQ ID No. 7 to 12, provided that the resultant CAR retains the ability to bind to TRBC1.

Variants of the above amino acid sequences may also be used in the present invention, provided that the resulting CAR binds TRBC1 or TRBC2 and does not significantly cross-react. Typically such variants have a high degree of sequence identity with one of the sequences given as SEQ ID No. 33, 34 or 35.

Variants of the CAR typically have at least about 75%, for example at least about 80%, 90%, 95%, 96%, 97%, 98% or 99% sequence identity with one of the sequences given as SEQ ID Nos 33, 34 and 35.

Nucleic Acid

The present invention further provides a nucleic acid encoding an agent such as a BiTE or CAR of the first aspect of the invention.

The nucleic acid sequence may encode a CAR comprising one of the amino acid sequences shown as SEQ ID No. 33, 34 and 35.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3 ′ and/or 5 ′ ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Vector

The present invention also provides a vector, or kit of vectors, which comprises one or more nucleic acid sequence(s) of the invention. Such a vector may be used to introduce the nucleic acid sequence(s) into a host cell so that it expresses a CAR according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention also relates to a cell, such as an immune cell, comprising a CAR according to the first aspect of the invention.

The cell may comprise a nucleic acid or a vector of the present invention.

The cell may be a T-cell or a natural killer (NK) cell.

T cell may be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEM RA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing the a CAR according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing a CAR according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR cells are generated by introducing DNA or RNA coding for the CAR by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding a CAR according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with a nucleic acid sequence(s) encoding a CAR of the invention.

The T or NK cells may then by purified, for example, selected on the basis of expression of the antigen-binding domain of the antigen-binding polypeptide.

The present invention also provides a kit which comprises a T or NK cell comprising a CAR according to the first aspect of the invention.

Pharmaceutical Composition

The present invention also relates to a pharmaceutical composition containing a plurality of cells expressing a CAR of the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

T-Cell Lymphoma and/or Leukaemia

The present invention relates to agents, cells and methods for treating a T-cell lymphoma and/or leukaemia.

A method for treating a T-cell lymphoma and/or leukaemia relates to the therapeutic use of an agent. Herein the agent may be administered to a subject having an existing disease of T-cell lymphoma and/or leukaemia in order to lessen, reduce or improve at least one symptom associated with the disease and/or to slow down, reduce or block the progression of the disease.

The method of the present invention may be used for the treatment of any lymphoma and/or leukaemia associated with the clonal expansion of a cell expressing a T-cell receptor (TCR) comprising a β constant region. As such the present invention relates to a method for treating a disease which involves malignant T cells which express a TCR comprising a TRBC.

The method of the present invention may be used to treat a T-cell lymphoma in which the malignant T-cell expresses a TCR comprising a TRBC. 'Lymphoma' is used herein according to its standard meaning to refer to a cancer which typically develops in the lymph nodes, but may also affect the spleen, bone marrow, blood and other organs. Lymphoma typically presents as a solid tumour of lymphoid cells. The primary symptom associated with lymphoma is lymphadenopathy, although secondary (B) symptoms can include fever, night sweats, weight loss, loss of appetite, fatigue, respiratory distress and itching.

The method of the present invention may be used to treat a T-cell leukaemia in which the malignant T-cell expresses a TCR comprising a TRBC. 'Leukaemia' is used herein according to its standard meaning to refer to a cancer of the blood or bone marrow.

The following is an illustrative, non-exhaustive list of diseases which may be treated by the method of the present invention.

Peripheral T-Cell Lymphoma

Peripheral T-cell lymphomas are relatively uncommon lymphomas and account fewer than 10% of all non-Hodgkin lymphomas (NHL). However, they are associated with an aggressive clinical course and the causes and precise cellular origins of most T-cell lymphomas are still not well defined.

Lymphoma usually first presents as swelling in the neck, underarm or groin. Additional swelling may occur where other lymph nodes are located such as in the spleen. In general, enlarged lymph nodes can encroach on the space of blood vessels, nerves, or the stomach, leading to swollen arms and legs, to tingling and numbness, or to feelings of being full, respectively. Lymphoma symptoms also include nonspecific symptoms such as fever, chills, unexplained weight loss, night sweats, lethargy, and itching.

The WHO classification utilizes morphologic and immunophenotypic features in conjunction with clinical aspects and in some instances genetics to delineate a prognostically and therapeutically meaningful categorization for peripheral T-cell lymphomas (Swerdlow et al.; WHO classification of tumours of haematopoietic and lymphoid tissues. 4th ed.; Lyon: IARC Press; 2008). The anatomic localization of neoplastic T-cells parallels in part their proposed normal cellular counterparts and functions and as such T-cell lymphomas are associated with lymph nodes and peripheral blood. This approach allows for better understanding of some of the manifestations of the T-cell lymphomas, including their cellular distribution, some aspects of morphology and even associated clinical findings.

The most common of the T-cell lymphomas is peripheral T-cell lymphoma, not otherwise specified (PTCL-NOS) comprising 25% overall, followed by angioimmunoblastic T-cell lymphoma (AITL) (18.5%)

Peripheral T-Cell Lymphoma, not Otherwise Specified (PTCL-NOS)

PTCL-NOS comprises over 25% of all peripheral T-cell lymphomas and NIT-cell lymphomas and is the most common subtype. It is determined by a diagnosis of exclusion, not corresponding to any of the specific mature T-cell lymphoma entities listed in the current WHO 2008. As such it is analogous to diffuse large B-cell lymphoma, not otherwise specified (DLBCL-NOS).

Most patients are adults with a median age of 60 and a male to female ratio 2:1. The majority of cases are nodal in origin, however, extranodal presentations occur in approximately 13% of patients and most commonly involve skin and gastrointestinal tract.

The cytologic spectrum is very broad, ranging from polymorphous to monomorphous. Three morphologically defined variants have been described, including lymphoepithelioid (Lennert) variant, T-zone variant and follicular variant. The lymphoepithelioid variant of PTCL contains abundant background epithelioid histiocytes and is commonly positive for CD8. It has been associated with a better prognosis. The follicular variant of PTCL-NOS is emerging as a potentially distinct clinicopathologic entity.

The majority of PTCL-NOS have a mature T-cell phenotype and most cases are CD4-positive. 75% of cases show variable loss of at least one pan T-cell marker (CD3, CD2, CD5 or CD7), with CD7 and 005 being most often downregulated. CD30 and rarely CD15 can be expressed, with CD15 being an adverse prognostic feature. CD56 expression, although uncommon, also has negative prognostic impact. Additional adverse pathologic prognostic factors include a proliferation rate greater than 25% based on KI-67 expression, and presence of more than 70% transformed cells. Immunophenotypic analysis of these lymphomas has offered little insight into their biology.

Angioimmunoblastic T-Cell Lymphoma (AITL)

AITL is a systemic disease characterized by a polymorphous infiltrate involving lymph nodes, prominent high endothelial venules (HEV) and peri-vascular expansion of follicular dendritic cell (FDC) meshworks. AITL is considered as a de-novo T-cell lymphoma derived from $\alpha\beta$ T-cells of follicular helper type (TFH), normally found in the germinal centres.

AITL is the second most common entity among peripheral T-cell lymphoma and NK/T-cell lymphomas, comprising about 18.5% of cases. It occurs in middle aged to elderly adults, with a median age of 65 years old, and an approximately equal incidence in males and females. Clinically, patients usually have advanced stage disease, with generalized lymphadenopathy, hepatosplenomegaly and prominent constitutional symptoms. Skin rash with associated pruritus is commonly present. There is often polyclonal hypergammaglobulinemia, associated with autoimmune phenomena.

Three different morphologic patterns are described in AITL. The early lesion of AITL (Pattern I) usually shows preserved architecture with characteristic hyperplastic follicles. The neoplastic proliferation is localized to the periphery of the follicles. In Pattern 11 the nodal architecture is partially effaced with retention of few regressed follicles. The subcapsular sinuses are preserved and even dilated. The paracortex contains arborizing HEV and there is a proliferation of FDC beyond the B-cell follicle. The neoplastic cells are small to medium in size, with minimal cytologic atypia. They often have clear to pale cytoplasm, and may show distincT-cell membranes. A polymorphous inflammatory background is usually evident.

Although AITL is a T-cell malignancy, there is a characteristic expansion of B-cells and plasma cells, which likely reflects the function of the neoplastic cells as TFH cells. Both EBV-positive and EBV-negative B-cells are present. Occasionally, the atypical B-cells may resemble Hodgkin/Reed-Sternberg-like cells morphologically and immuno phenotypically, sometimes leading to a diagnostic confusion with that entity. The B-cell proliferation in AFL may be extensive and some patients develop secondary EBV-positive diffuse large B-cell lymphomas (DLBCL) or—more rarely—EBV-negative B-cell tumors, often with plasmacytic differentiation.

The neoplastic CD4-positive T-cells of AITL show strong expression of CD10 and CD279 (PD-1) and are positive for CXCL13. CXCL13 leads to an increased B-cell recruitment to lymph nodes via adherence to the HEV, B-cell activation, plasmacytic differentiation and expansion of the FDC meshworks, all contributing to the morphologic and clinical features of AFL. Intense PD-1-expression in the perifollicular tumor cells is particularly helpful in distinguishing AITL Pattern I from reactive follicular and paracortical hyperplasia.

The follicular variant of PTCL-NOS is another entity with a TFH phenotype. In contradistinction to AITL, it does not have prominent HEV or extra-follicular expansion of FDC meshworks. The neoplastic cells may form intrafollicular aggregates, mimicking B-cell follicular lymphoma, but also can have interfollicular growth pattern or involve expanded mantle zones. Clinically, the follicular variant of PTCL-NOS is distinct from AITL as patients more often present with early stage disease with partial lymph node involvement and may lack the constitutional symptoms associated with AITL.

Anaplastic Large Cell Lymphoma (ALCL)

ALCL may be subdivided as ALCL-'anaplastic lymphoma kinase' (ALK)+ or ALCL-ALK−.

ALCL-ALK+ is one of the best-defined entities within the peripheral T-cell lymphomas, with characteristic "hallmark cells" bearing horseshoe-shaped nuclei and expressing ALK and CD30. It accounts for about 7% of all peripheral T-cell and NK-cell lymphomas and is most common in the first three decades of life. Patients often present with lymphadenopathy, but the involvement of extranodal sites (skin, bone, soft tissues, lung, liver) and B symptoms is common.

ALCL, ALK+ shows a wide morphologic spectrum, with 5 different patterns described, but all variants contain some hallmark cells. Hallmark cells have eccentric horseshoe- or kidney-shaped nuclei, and a prominent perinuclear eosinophilic Golgi region. The tumour cells grow in a cohesive pattern with predilection for sinus involvement. Smaller tumour cells predominate in the small cell variant, and in the lymphohistiocytic variant abundant histiocytes mask the presence of tumour cells, many of which are small.

By definition, all cases show ALK and CD30 positivity, with expression usually weaker in the smaller tumour cells. There is often loss of pan-T-cell markers, with 75% of cases lacking surface expression of CD3.

ALK expression is a result of a characteristic recurrent genetic alteration consisting of a rearrangement of ALK gene on chromosome 2p23 to one of the many partner genes, resulting in an expression of chimeric protein. The most common partner gene, occurring in 75% of cases, is Nucleophosmin (NPM1) on chromosome 5q35, resulting in t(2; 5)(p23;q35). The cellular distribution of ALK in different translocation variants may vary depending on the partner gene.

ALCL-ALK− is included as a provisional category in the 2008 WHO classification. It is defined as a CD30 positive T-cell lymphoma that is morphologically indistinguishable from ALCL-ALK+ with a cohesive growth pattern and presence of hallmark cells, but lacking ALK protein expression.

Patients are usually adults between the ages of 40 and 65, in contrast to ALCL-ALK+, which is more common in children and young adults. ALCL-ALK− can involve both lymph nodes and extranodal tissues, although the latter is seen less commonly than in ALCL-ALK+. Most cases of ALCL-ALK− demonstrate effacement of lymph node architecture by sheets of cohesive neoplastic cells with typical "hallmark" features. In contrast to the ALCL-ALK+, the small cell morphologic variant is not recognized.

Unlike its ALK+ counterpart, ALCL-ALK− shows a greater preservation of surface T-cell marker expression, while the expression of cytotoxic markers and epithelial membrane antigen (EMA) is less likely. Gene expression signatures and recurrent chromosomal imbalances are different in ALCL-ALK− and ALCL-ALK+, confirming that they are distinct entities at a molecular and genetic level.

ALCL-ALK− is clinically distinct from both ALCL-ALK+ and PTCL-NOS, with significant differences in prognosis among these three different entities. The 5 year overall survival of ALCL-ALK− is reported as 49% which is not as good as that of ALCL-ALK+ (at 70%), but at the same time it is significantly better than that of PTCL-NOS (32%).

Enteropathy-Associated T-Cell Lymphoma (EATL)

EATL is an aggressive neoplasm which thought to be derived from the intraepithelial T-cells of the intestine. Two morphologically, immunohistochemically and genetically distinct types of EATL are recognized in the 2008 WHO classification: Type I (representing the majority of EATL) and Type II (comprising 10-20% of cases).

Type I EATL is usually associated with overt or clinically silent gluten-sensitive enteropathy, and is more often seen in patients of Northern European extraction due to high prevalence of celiac disease in this population.

Most commonly, the lesions of EATL are found in the jejunum or ileum (90% of cases), with rare presentations in duodenum, colon, stomach, or areas outside of the gastrointestinal tract. The intestinal lesions are usually multifocal with mucosal ulceration. Clinical course of EATL is aggressive with most patients dying of disease or complications of disease within 1 year.

The cytological spectrum of EATL type I is broad, and some cases may contain anaplastic cells. There is a polymorphous inflammatory background, which may obscure the neoplastic component in some cases. The intestinal mucosa in regions adjacent to the tumour often shows features of celiac disease with blunting of the villi and increased numbers of intraepithelial lymphocytes (IEL), which may represent lesional precursor cells.

By immunohistochemistry, the neoplastic cells are often CD3+CD4−CD8−CD7+CD5−CD56−βF1+, and contain cytotoxic granule-associated proteins (TIA-1, granzyme B, perforin). CD30 is partially expressed in almost all cases. CD103, which is a mucosal homing receptor, can be expressed in EATL.

Type II EATL, also referred to as monomorphic CD56+ intestinal T-cell lymphoma, is defined as an intestinal tumour composed of small- to medium-sized monomorphic T-cells that express both CD8 and CD56. There is often a lateral spread of tumour within the mucosa, and absence of an inflammatory background. The majority of cases express the γδ TCR, however there are cases associated with the αβ TCR.

Type H EATL has a more world-wide distribution than Type I EATL and is often seen in Asians or Hispanic populations, in whom celiac disease is rare. In individuals of European descent EATL, II represents about 20% of intestinal T-cell lymphomas, with a history of celiac disease in at least a subset of cases. The clinical course is aggressive.

Hepatosplenic T-Cell Lymphoma (HSTL)

HSTL is an aggressive systemic neoplasm generally derived from γδ cytotoxic T-cells of the innate immune system, however, it may also be derived from αβ T-cells in rare cases. It is one of the rarest T-cell lymphomas, and typically affects adolescents and young adults (median age, 35 years) with a strong male predominance.

Extranodal NK/T-Cell Lymphoma Nasal Type

Extranodal NK/T-cell lymphoma, nasal type, is an aggressive disease, often with destructive midline lesions and necrosis. Most cases are of NK-cell derivation, but some cases are derived from cytotoxic T-cells. It is universally associated with Epstein-Barr Virus (EBV).

Cutaneous T-Cell Lymphoma

The method of the present invention may also be used to treat cutaneous T-cell lymphoma Cutaneous T-cell lymphoma (CTCL) is characterised by migration of malignant T-cells to the skin, which causes various lesions to appear. These lesions change shape as the disease progresses, typically beginning as what appears to be a rash and eventually forming plaques and tumours before metastasizing to other parts of the body.

Cutaneous T-cell lymphomas include those mentioned in the following illustrative, non-exhaustive list; mycosis fungoides, pagetoid reticulosis, Sézary syndrome, granulomatous slack skin, lymphomatoid papulosis, pityriasis lichenoides chronica, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma and angiocentric lymphoma.

The signs and symptoms of CTCL vary depending on the specific disease, of which the two most common types are mycosis fungoides and Sézary syndrome. Classic mycosis fungoides is divided into three stages:

Patch (atrophic or nonatrophic): Nonspecific dermatitis, patches on lower trunk and buttocks; minimal/absent pruritus;

Plaque: Intensely pruritic plaques, lymphadenopathy; and

Tumor: Prone to Ulceration

Sézary syndrome is defined by erythroderma and leukemia. Signs and symptoms include edematous skin, lymphadenopathy, palmar and/or plantar hyperkeratosis, alopecia, nail dystrophy, ectropion and hepatosplenomegaly.

Of all primary cutaneous lymphomas, 65% are of the T-cell type. The most common immunophenotype is CD4 positive. There is no common pathophysiology for these diseases, as the term cutaneous T-cell lymphoma encompasses a wide variety of disorders.

The primary etiologic mechanisms for the development of cutaneous T-cell lymphoma (ie, mycosis fungoides) have not been elucidated. Mycosis fungoides may be preceded by a T-cell-mediated chronic inflammatory skin disease, which may occasionally progress to a fatal lymphoma.

Primary Cutaneous ALCL (C-ALCL)

C-ALCL is often indistinguishable from ALC-ALK− by morphology. It is defined as a cutaneous tumour of large cells with anaplastic, pleomorphic or immunoblastic morphology with more than 75% of cells expressing CD30. Together with lymphomatoid papulosis (LyP), C-ALCL belongs to the spectrum of primary cutaneous CD30-positive T-cell lymphoproliferative disorders, which as a group comprise the second most common group of cutaneous T-cell lymphoproliferations after mycosis fungoides.

The immunohistochemical staining profile is quite similar to ALCL-ALK−, with a greater proportion of cases staining positive for cytotoxic markers. At least 75% of the tumour cells should be positive for CD30. CD15 may also be expressed, and when lymph node involvement occurs, the differential with classical Hodgkin lymphoma can be difficult. Rare cases of ALCL-ALK+ may present with localized cutaneous lesions, and may resemble C-ALCL.

T-Cell Acute Lymphoblastic Leukaemia

T-cell acute lymphoblastic leukaemia (T-ALL) accounts for about 15% and 25% of ALL in paediatric and adult cohorts respectively. Patients usually have high white blood cell counts and may present with organomegaly, particularly mediastinal enlargement and CNS involvement.

The method of the present invention may be used to treat T-ALL which is associated with a malignant T cell which expresses a TCR comprising a TRBC.

T-Cell Prolymphocytic Leukaemia

T-cell-prolymphocytic leukemia (T-PLL) is a mature T-cell leukaemia with aggressive behaviour and predilection for blood, bone marrow, lymph nodes, liver, spleen, and skin involvement. T-PLL primarily affects adults over the age of 30. Other names include T-cell chronic lymphocytic leukaemia, "knobby" type of T-cell leukaemia, and T-prolymphocytic leukaemia/T-cell lymphocytic leukaemia.

In the peripheral blood, T-PLL consists of medium-sized lymphocytes with single nucleoli and basophilic cytoplasm with occasional blebs or projections. The nuclei are usually round to oval in shape, with occasional patients having cells with a more irregular nuclear outline that is similar to the cerebriform nuclear shape seen in Sezary syndrome. A small cell variant comprises 20% of all T-PLL cases, and the Sezary cell-like (cerebriform) variant is seen in 5% of cases.

T-PLL has the immunophenotype of a mature (post-thymic) T-lymphocyte, and the neoplastic cells are typically positive for pan-T antigens CD2, CD3, and CD; and negative for TdT and CD1a. The immunophenotype CD4+/CD8− is present in 60% of cases, the CD4+/CD8+ immunophenotype is present in 25%, and the CD4−/CD8+ immunophenotype is present in 15% of cases Pharmaceutical Composition The method of the present invention may comprise the step of administering the agent in the form of a pharmaceutical composition.

The agent may be administered with a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents.

Administration

The administration of the agent can be accomplished using any of a variety of routes that make the active ingredient bioavailable. For example, the agent can be administered by oral and parenteral routes, intraperitoneally, intravenously, subcutaneously, transcutaneously, intramuscularly, via local delivery for example by catheter or stent.

Typically, a physician will determine the actual dosage which will be most suitable for an individual subject and it will vary with the age, weight and response of the particular patient. The dosage is such that it is sufficient to reduce or deplete the number of clonal T-cells expressing either TRBC1 or TRBC2.

Use

The present invention also provides an agent for use in treating a T-cell lymphoma according to the method of the first aspect. The agent may be any agent as defined above.

The present invention also relates to the use of an agent as defined above in the manufacture of a medicament for the treatment of a T-cell lymphoma according to the method of the first aspect.

Kit

The present invention further provides a kit comprising an agent as defined above for use in the treatment of a T-cell lymphoma according to the method of the first aspect.

The kit may also comprise a reagent(s) suitable for determining the TRBC of a malignant T-cell. For example the kit may comprise PCR primers or an antibody (antibodies) which are specific for either TRBC1 or TRBC2.

Method for Determining T-Cell Lymphoma and/or Leukaemia

The present invention further relates to a method for determining the presence of a T-cell lymphoma or leukaemia in a subject which comprises the step of determining the proportion of T-cells in a sample from a subject which are either TRBC1 or TRBC2 positive.

T-cell lymphomas involve the clonal expansion of individual malignant T-cells. As such the presence of a T-cell lymphoma in a subject may be identified by determining the proportion of either TRBC1 or TRBC2 T-cells in a sample derived from a patient.

The sample may be a peripheral blood sample, a lymph sample or a sample taken directly from a tumour e.g. a biopsy sample.

The proportion of total T-cells which are TRBC1 or TRBC2 positive which indicates the presence of a T-cell lymphoma or leukaemia may be, for example 80, 85, 90, 95, 98 or 99% of a total population of cells.

The method may involve determining infiltration by a distinct population of T-cells in a biopsy or a sample. Herein, the presence of a T-cell lymphoma or leukaemia is indicated where 80, 85, 90, 95, 98 or 99% of a total population of T cells in the sample are either TRBC1 or TRBC2.

The total T-cells in a sample may identified by determining the number of cells in the sample which express CD3, CD4, CD8 and/or CD45. A combination of these markers may also be used.

The proportion of total T cells in a sample which express either TRBC1 or TRBC2 may be determined using methods which are known in the art, for example flow cytometry, immunohistochemistry or fluorescent microscopy.

The invention will now be further described by way of Examples, which are meant to serve to assist one of ordinary skill in the art in carrying out the invention and are not intended in any way to limit the scope of the invention.

EXAMPLES

Example 1—Discrimination of TRBC1 and TRBC2-Expressing Cells

The JOVI-1 antibody has been previously disclosed by Viney et al. (Hybridoma; 1992; 11(6); 701-713) and is available commercially (Abcam, ab5465). The present inventors determined that JOVI-1 is able to discriminate cells based on specific expression of TRBC1 or TRBC2.

Figure 4:
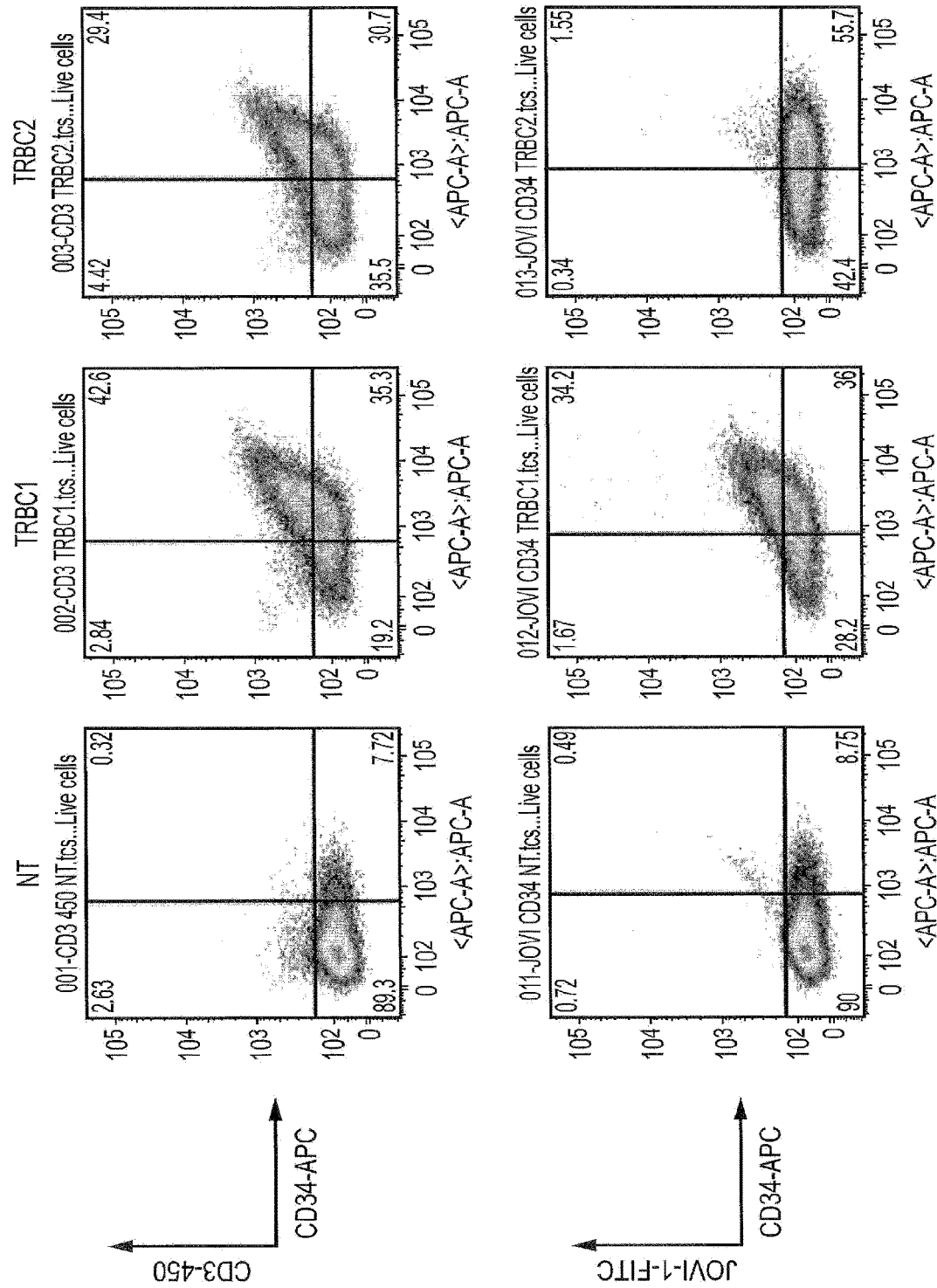
FIG. 4: Definitive demonstration that the JOVI-1 antibody binds to TRBC1 but not TRBC2. Genetic engineering of cells was used to definitively demonstrate that the JOVI-1 monoclonal antibody recognizes TRBC1 variant of the TCRβ constant chain. A tri-cistronic retroviral cassette was generated. This coded for both the TCRα and TCRβ chains of a human TCR which recognizes the minor histocompatibility antigen HA1, along with truncated human CD34 as a convenient marker gene. The HA1 TCR is natively TRBC2. A second retroviral cassette was generated which was identical to the first except the 4 residues in the TCR β constant region which differentiate TRBC1 from TRBC2 were changed to those coded by TRBC1. Jurkat T-cells which have both their TCRα and TCRβ chains knocked-out were transduced with either vector. These cells were stained with either a pan-TCR/CD3 antibody or the monoclonal JOVI-1 conjugated along with antibodies against CD34 and analysed in a flow cytometer. The upper row demonstrates staining with a pan-TCR/CD3 antibody v CD34 (marker of transduction), the lower row demonstrates staining with JOVI-1 vs CD34. Transduced cells demonstrate similar TCR/CD3 staining but only TRBC1+ve cells stain with JOVI-1. Hence, JOVI-1 is specific to TRBC1 and further it is possible to use an antibody to distinguish TRBC1 and 2 TCRs.

The inventors generated two plasmid vectors supplying the complete variable and constant regions of the TCR, differing only in expression of either TRBC1 or TRBC2. These plasmids were used to generate retroviral supernatant by transient transfection of 293T-cells. This supernatant was used to stably transduce Jurkats TCR-knockout T-cells (a TALL cell line with a mutation at the TCR beta chain locus precluding expression of this chain, and thereby the entire surface TCR/CD3 complex). This resulted in the production of cell lines which were identical other than expression of either TRBC1 or TRBC2. Staining of these cell lines revealed full expression of the surface TCR/CD3 complex, and that only cells expressing TRBC1 stained with the JOVI-1 antibody (FIG. 4).

Figure 6:
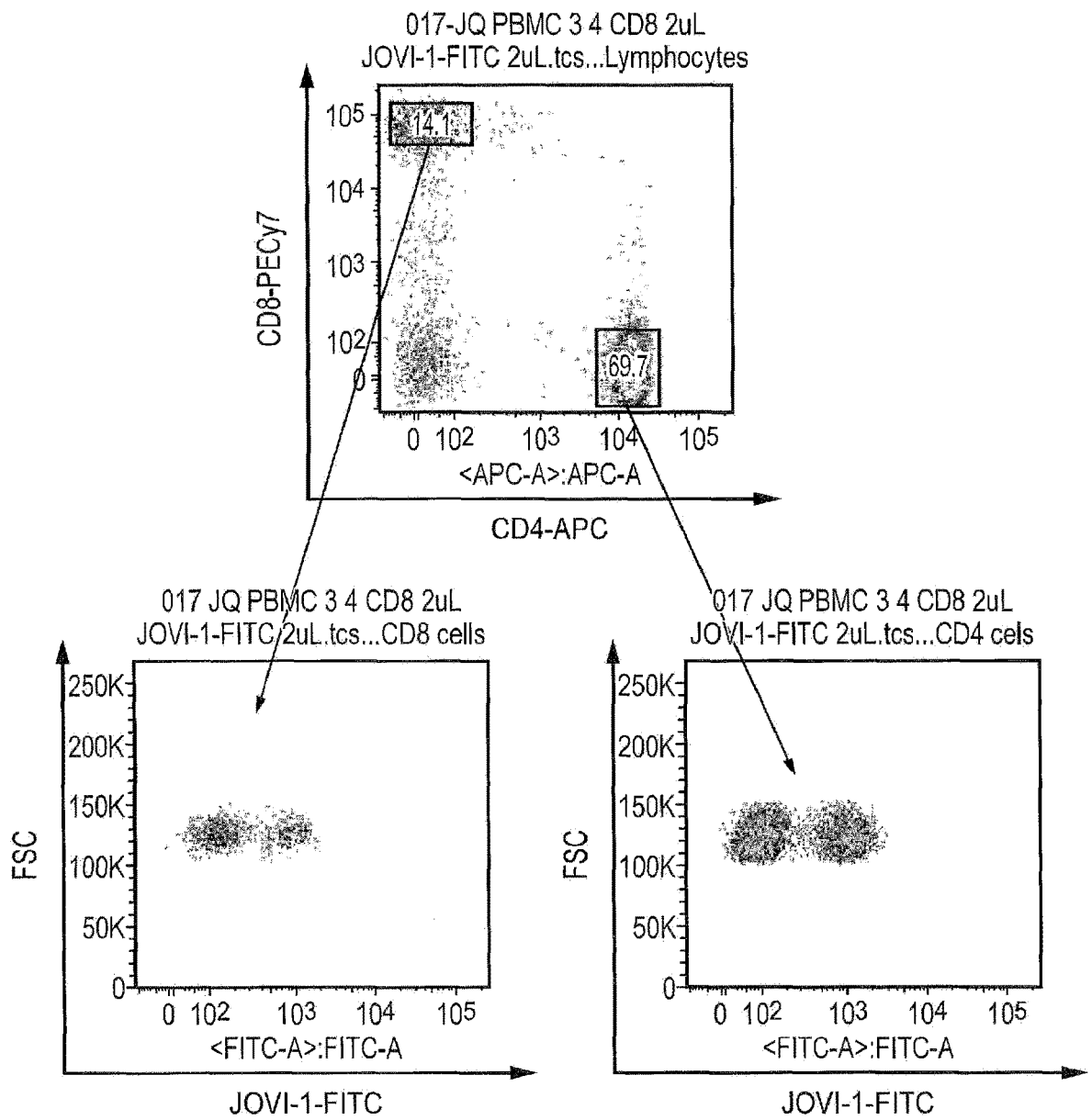
FIG. 6: Example of normal donor T-cell expression of TRBC1. Normal donor peripheral blood mononuclear cells were stained with antibodies against CD3, CD4, CD8 and JOVI-1 and analysed by flow cytometry. CD4+ and CD8+ T-cell populations are shown on the upper panel. Each of this population is gated and forward scatter vs JOVI-1 staining are shown on the Y and X-axes respectively. These data show that both CD4+ and CD8+ compartments contain cells which are TRBC1 +ve and −ve. This is representative data from one donor.
Figure 7:
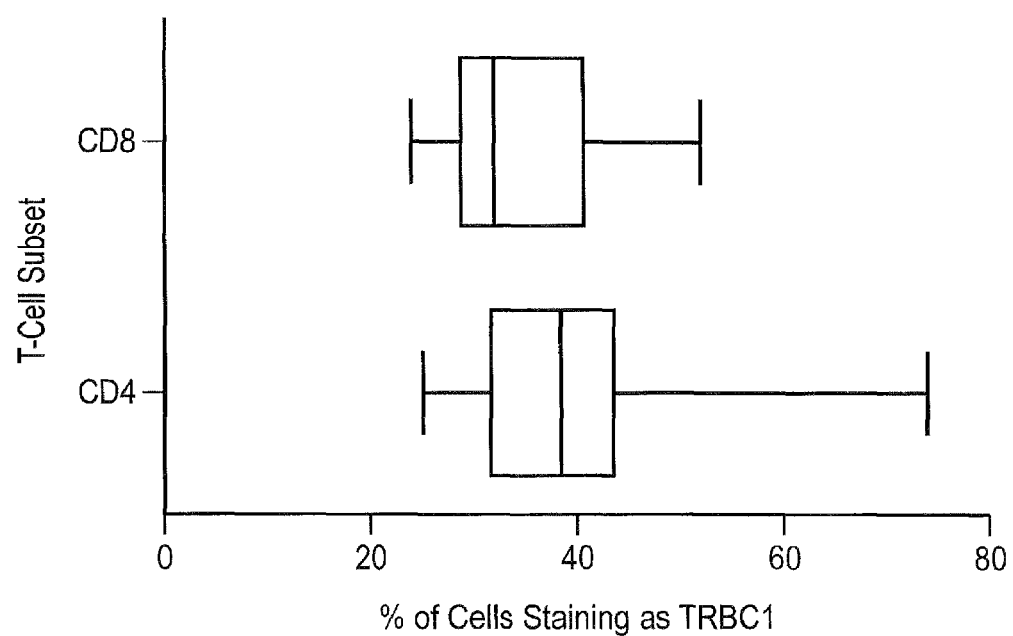
FIG. 7: TRBC1+ T-cells in several normal donors. Ten normal donors were bled and peripheral blood mononuclear cells were stained as described in FIG. 4 above. The aggregate data of the proportion of TRBC1 T-cells in both CD4 and CD8 compartments is shown in a bar graph along with median and range. All donors had TRBC1+ and TRBC1− compartments. Median % of TRBC1+ cells=36%.

Example 2 ® Normal Donor CD4+ and CD8+ T-Cells Contain Separate TRBC1-Positive and TRBC1-Negative Populations The inventors tested the JOVI-1 antibody on primary human T-cells of normal donors. These analyses revealed that all donors had a proportion of both CD4+ and CD8+ T cells which expressed TRBC1 and a proportion of each which did not. Approximately 20-50% of normal 004+ and CD8+ T-cells are TRBC1 +ve (FIGS. 6 and 7).

Example 3—Clonal T-Cell Lines Expressing TCR are TRBC1 Positive or Negative

Figure 8:
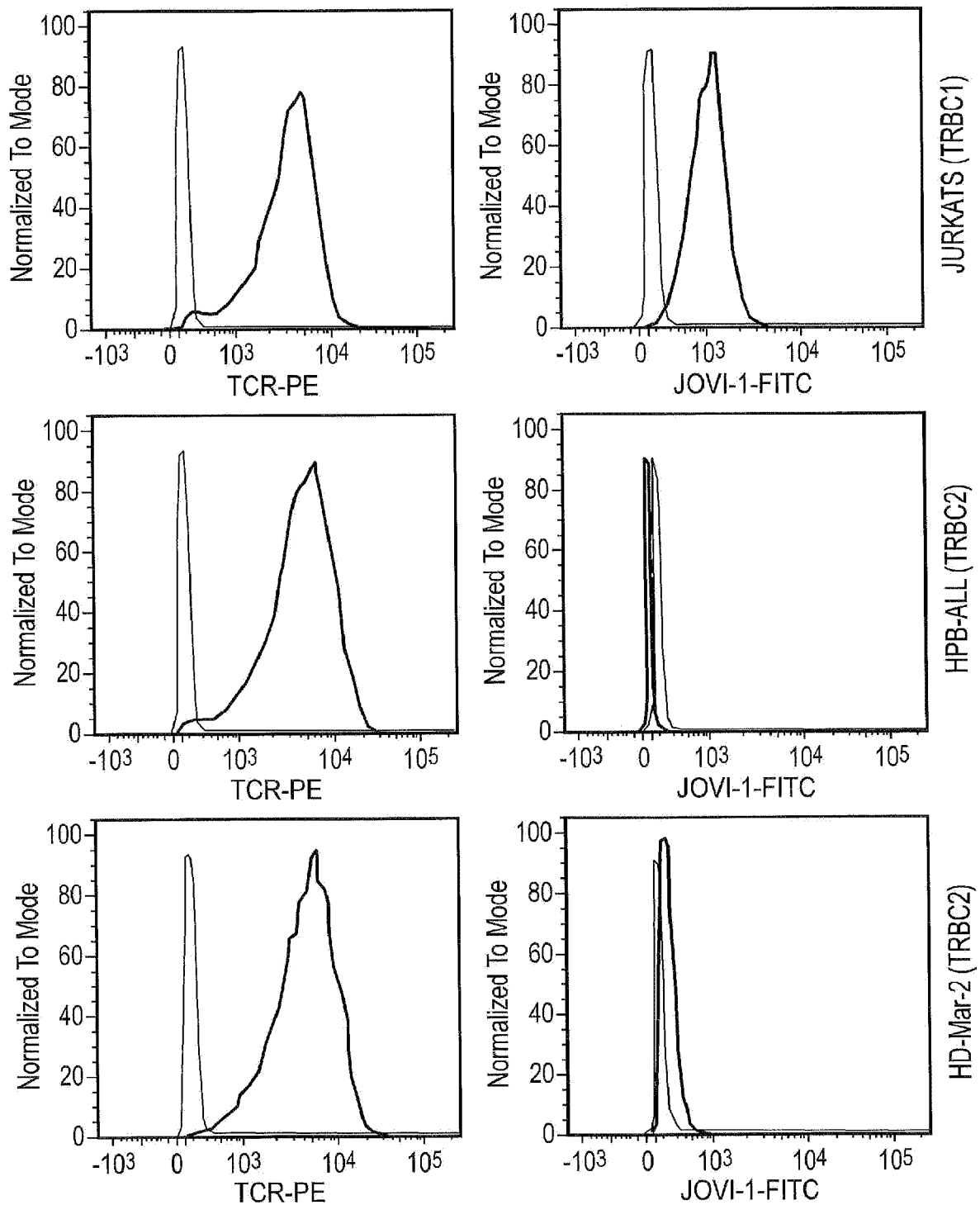
FIG. 8: T-cell malignancy derived cell lines stained with JOVI-1. Several cell lines have been derived from T-cell malignancies. Many of these cell lines still express the TCR. We selected Jurkats (A T-cell leukaemia cell line), HPB-ALL (another T-cell leukaemia cell line) and HD-Mar-2 (a T-cell lymphoma cell line) for study. By staining these cell lines with a pan-TCR/CD3 antibody, we were able to demonstrate that all three express TCR (left panels, staining overlaid over isotype control staining). Next, by staining with JOVI-1 we were able to determine that these T-cell lines are either TRBC1 negative or positive. Only Jurkats cells (TRBC1+) and not HPB-ALL or HD-Mar-2 (TRBC2+) cells stain with JOVI-1, supporting exclusive expression of either TRBC1 or 2.

Cell lines are derived from an original clonal tumour population in a patient. Staining of T-cell lines expressing TCR reveals that T-cells express either TRBC1 or TRBC2, confirming this as a marker of clonality. Of three T-cell lines tested, Jurkats cells (known to be TRBC1+) and not HPB-ALL or HD-Mar-2 (known to be TRBC2+) cells stain with JOVI-1, supporting exclusive expression of either TRBC1 or 2 (FIG. 8).

Example 4—Primary Clonal T-Cell in Patients with T-Prolymphocyctic Leukaemia are TRBC1 Positive or Negative Clonal T-cells extracted from peripheral blood of patients with T-prolymphocytic leukaemia (T-PLL) are either uniformly TRBC1 positive or TRBC1 negative.

Example 5—The Effect of Mutation of the Residues that are Unique to TCBC1

Figure 5:
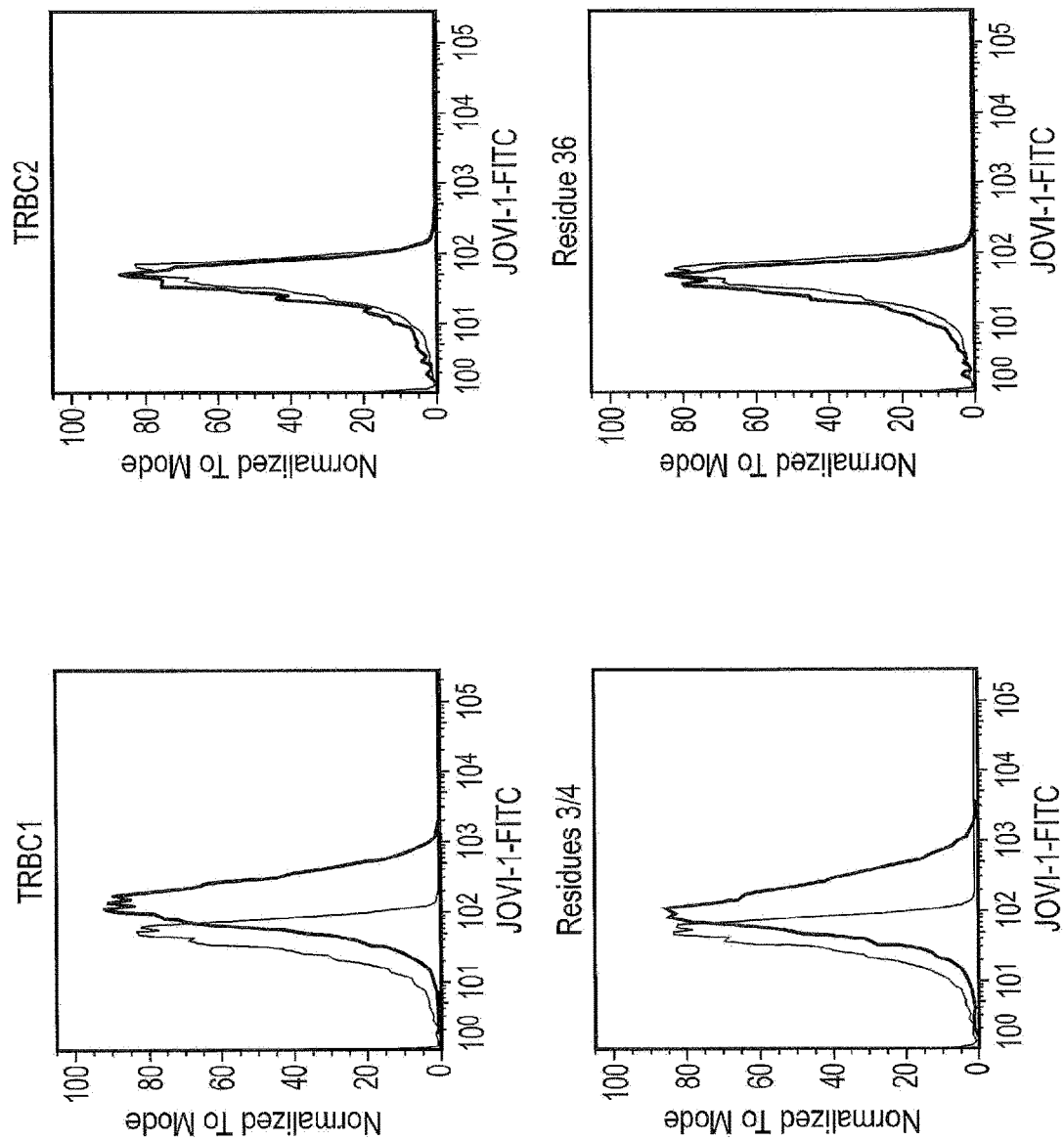
FIG. 5: The JOVI-1 mAb differentiates TRBC1 from TRBC2 by recognizing residues 3 and 4 of the TRBC. To precisely determine how JOVI-1 discriminates TRBC1 from TRBC2, the HA1 TCR TRBC2 construct detailed above was mutated to make two TRBC1/2 hybrids. An additional variant was generated so that only residues 3 and 4 of the TCRβ constant chain were changed from those of TRBC2 to those found in TRBC1. A further variant was made where only residue 36 was changed from that found in TRBC2 to TRBC1. TCR knock-out Jurkat T-cells were transduced with these new constructs. The original TRBC2 and TRBC1 transduced Jurkats described in FIG. 4 were used as controls. The Jurkat T-cells were stained with JOVI-1 and analysed with a flow cytometer. Staining of JOVI-1 is overlaid over that of non-transduced TCR knock-out Jurkat T-cells. JOVI-1 stained Jurkats expressing the TRBC1 TCR but not the TRBC2 TCR. JOVI-1 stained TRBC1/2 hybrid where only TRBC residues 3 and 4 were those of TRBC1. JOVI-1 did not stain Jurkat T-cells where only TRBC residue 36 was that of TRBC1.

Plasmid vectors, coding for TCRs which are identical, except for hybrid TRBC1/2 mutations in the TCR β chain constant region, were generated. Analysis showed that JOVI-1 recognizes differences in residues at positions 3 and 4 of TCR β constant chain indicating that these residues are accessible to antibody recognition and are likely the best targets to generate agents discriminating TRBC1 from TRBC2 or TRBC2 from TRBC1 (FIG. 5).

Example 6—Specific Lysis of TRBC1 but not TRBC2 TCR Expressing T-Cells

Wild-type Jurkat T-cells (CD34−, TRBC1+) were mixed with TCRαβ knock-out Jurkat T-cells transduced with TRBC2 co-expressed with the 0034 marker gene (CD34+ TRBC2+). These cells were incubated with JOVI-1 alone or incubated with JOVI-1 and complement for 1 hour. Cells were washed and stained for CD34, Annexin V and 7-AAD. Cells were analysed by flow-cytometry.

CD34 expression in the live population as defined by Annexin-V negative and 71AAD dim population is shown in FIGS. 9A-9B. Selective killing of TRBC1 T-cells (CD34−) was observed (FIGS. 9A-9B).

Wild-type Jurkat T-cells are naturally TRBC1+ and do not express the truncated CD34 marker gene. As described above the inventors derived a TRBC2+ Jurkat line by transducing TCRαβ knock-out Jurkat T-cells with a retroviral vector which codes for a TRBC2 TCR as well as the truncated CD34 marker gene. These T-cells were then mixed together. Next, the inventors incubated the T cells with either JOVI-1 alone or with JOVI-1 and complement for 1 hour. Conveniently, the inventors could discriminate TRBC1 and 2 populations by staining for the CD34 marker gene and thus avoided failing to detect TRBC1 TCRs due to TCR internalization after prolonged exposure to anti-TCR mAb. Cells were washed and stained for C034, Annexin V and 7-AAD. The cells were analysed by flow-cytometry. By gating on live cells (i.e. cells which were Annexin V negative and 7-AAD dim), the inventors could determine that TRBC1 T-cells were selectively killed by JOVI-1 in the presence of complement (FIGS. 9A-9B).

Example 7—Polyclonal Epstein Barr Virus (EBV) Specific T-Cells can be Split into Two Approximately Equal TRBC1/2 Populations Peripheral blood T-cells were drawn from a normal blood donor. Mononuclear cells were isolated and most of the cells were cryopreserved. A small number of cells were infected with a laboratory strain of EBV (B95-8). Over some weeks, an immortalized EBV infected cell line, known as a lymphoblastoid cell line (LCL) emerged. Such a cell line is known to present a large collection of different EBV antigens. The previously cryopreserved mononuclear cells were thawed and repeatedly stimulated with this LCL line weekly for 4 weeks in the presence of IL2. This process selectively expands EBV specific T-cells from the peripheral blood mononuclear population. It is also known that such a process results in a polyclonal line where >90% of the T-cells are EBV specific and represents the donor's EBV immune system. The specificity of this line is checked by showing a high degree of killing of autologous LCLs but not allogeneic LCLs or K562 cells (FIG. 10A). This cell line was then stained with JOVI-1 and shown to contain an approximately equal mixture of TRBC1 and TRBC2 T-cells (FIG. 10B).

Thus, if a therapeutic agent was administered which depleted either the TRBC1 or TRBC2 compartment, an adequate EBV immunity would remain. Since EBV immunity is regarded as a model system for an immune response it is reasonable to postulate that immunity to other pathogens would be equally conserved.

Example 8—JOV1 Staining of a Circulating Peripheral T-Cell Lymphoma

Figure 12:
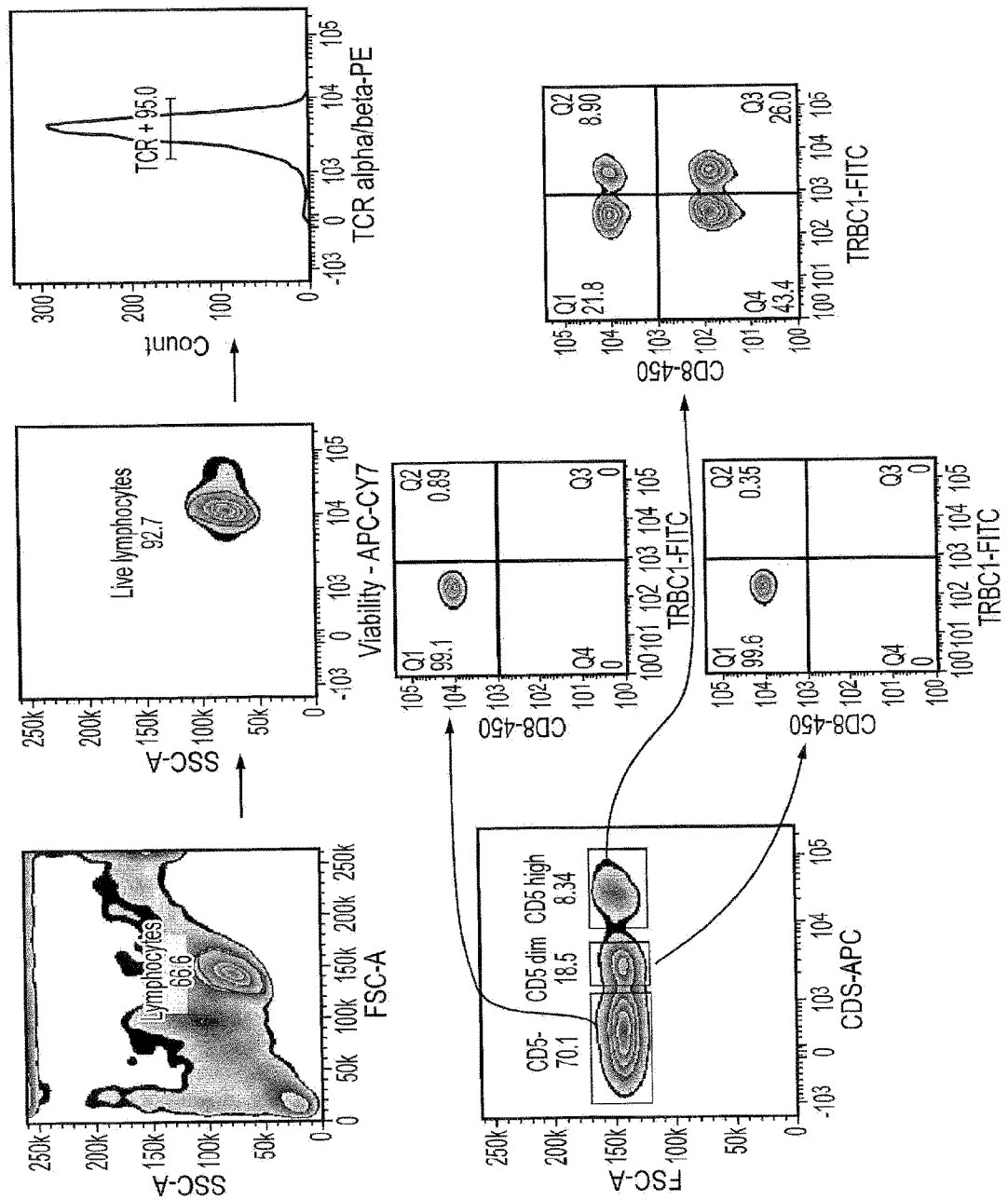
FIG. 12: Demonstration that a peripheral T-cell lymphoma is TRBC restricted, but normal circulating T-cells are not. Peripheral blood T-cells from a patient with circulating T-cell lymphoma cells were drawn. Peripheral mononuclear cells were isolated and stained with a panel of antibodies including CD5, TCR and JOVI-1. Normal and malignant T-cells could be differentiated on flow by CD5 expression intensity. CD5 bright (normal T-cells) had approximately equal TRBC1 and 2 populations. The CD5 intermediate and dim populations (the tumour) were all TRBC2 positive. If this patient had a TRBC2 directed therapy, the lymphoma would be eradicated and approximately half of their T-cells would be spared.

The hypothesis was that T-cell lymphomas, being clonal, would express either TRB1 or TRBC2 T-cell receptors, while normal T-cells being polyclonal would comprise of a population of T-cells which are a mixture of those that have TRBC1 or TRBC2. To demonstrate this, a blood sample of a T-cell lymphoma from a patient whose lymphoma was circulating in peripheral blood was obtained. Peripheral blood mononuclear cells were isolated and stained with a panel of antibodies which included CD5 and JOVI1. The total T-cell population (which contains both lymphoma and normal T-cells) was first identified. This population was comprised of T-cells with normal (bright) CD5 expression and T-cells with intermediate/dim CD5 expression. The former represent normal T-cells, while the latter represent the lymphoma. JOVI-1 binding was investigated next and the results are shown in FIG. 12.

The CD5 intermediate and dim populations (the tumour) were all TRBC2 positive.

Example 9—Elucidation of the VH/VL Sequences of JOVI-1

Using 5' RACE with primers which anneal to the constant regions of mouse IgG CH1 and the constant region of mouse kappa, we isolated a single functional VH sequence and a single functional VL sequence from the hybridoma JOVI-1. Sequences of the VH and VL are SEQ ID 1 and 2 respectively (see above). An annotated sequence of VH and VL is shown in FIG. 11.

Figure 13:
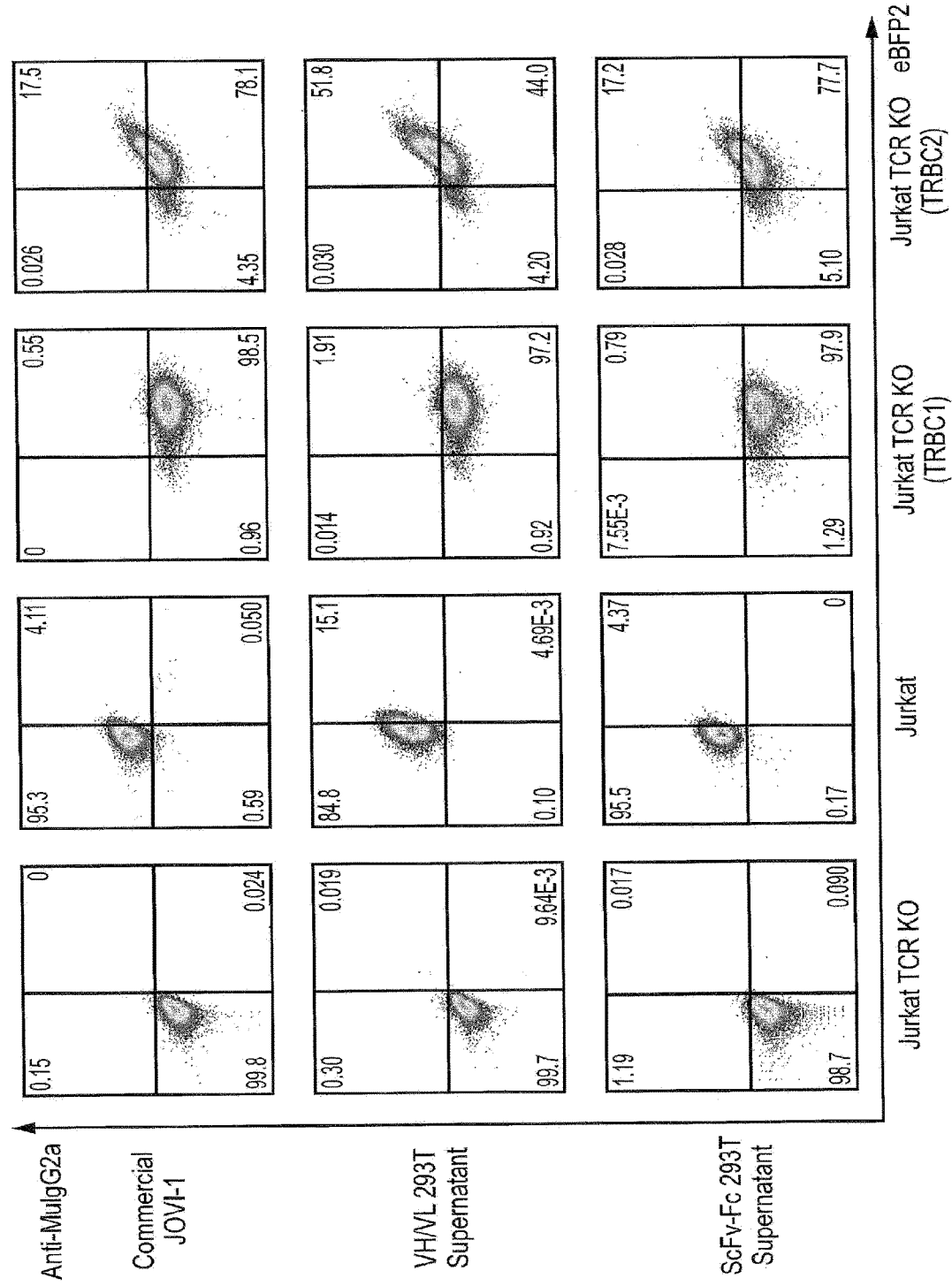
FIG. 13: Demonstration that the VH and VL derived from JOVI-1 were correct and that they can fold as a single-chain variable fragment. Original hybridoma supernatant, recombinant JOVI-1 antibody and scFv-Fc generated from transfected 293T cells were used to stain a number of cell lines: Jurkat TCR knock-outs, wild-type Jurkats, Jurkat TCR knock-out transduced with a TRBC1 TCR in a vector co-expressing eBFP2; Jurkat TCR knock-out transduced with a TRBD2 TCR in a vector co-expressing eBFP2. Staining was analysed by flow cytometry. Both the recombinant antibody and the scFv bound cells expressing TRBC2.
Figure 14:
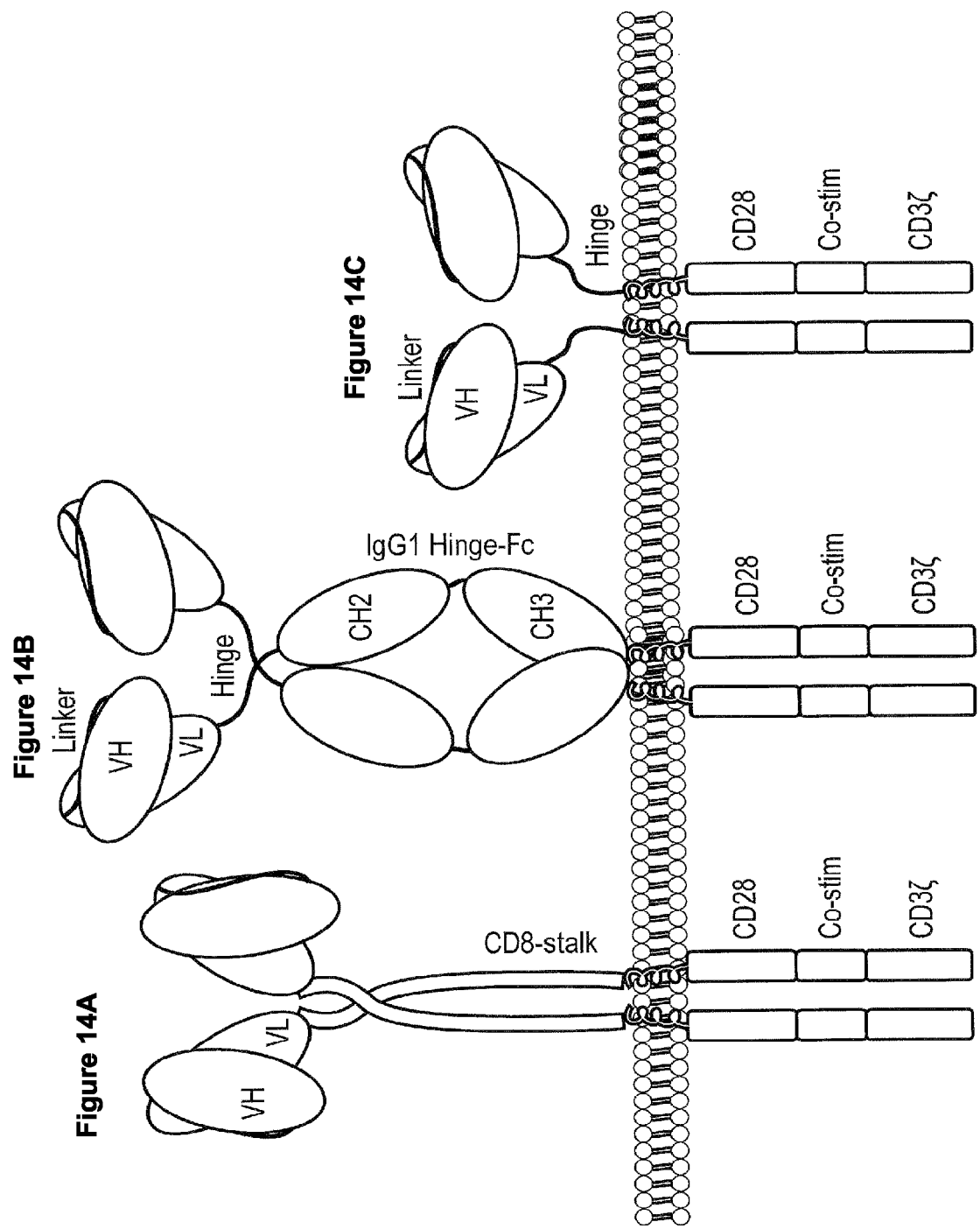
FIGS. 14A-14C: JOVI-1 based CARs in different formats. CARs typically comprise of a binding domain, a spacer, a transmembrane domain and an intracellular signalling domain. In this study CARs were generated which comprise of the JOVI-1 scFv; a spacer derived from either the CD8 stalk, the hinge-CH2-CH3 domain of human IgG1 with mutations which remove FcR binding; or a spacer derived from human IgG1.

These VH and VL sequences were cloned back in frame with mouse IgG heavy chain and kappa light chain respectively. In addition, the VH and VL were fused to form a single-chain variable fragment (scFv), this was fused to the hinge-CH2-CH3 region of mouse IgG2a to create a scFv-Fv. The amino acid sequence of the scFv is given in the Detailed Description as SEQ ID No. 3. Recombinant antibody and recombinant scFv-Fc were generated by transfection into 293T cells. Along with JOVI-1 from the hybridoma, the following cells were stained: Jurkats with TCR knocked out; wild-type Jurkats; Jurkat TCR knock out transduced with TRBC1 co-expressed with eBFP2 and Jurkat TCR knock-out transduced with TRBC2 co-expressed with eBFP2. Both recombinant antibody and scFv-Fc derived from JOVI bound TRBC2 confirming that we had identified the correct VH/VL, and that JOVI-1 VH/VL can fold as a scFv. This binding data is shown in FIG. 13.

Example 10—Function of JOVI-1 Based CAR

The JOVI-1 scFv was cloned into CAR formats. To elucidate which spacer length would result in the optimal JOVI-1 based CAR, $3^{rd}$ generation CARs were generated with either a human Fc spacer, a human CD8 stalk spacer or with a spacer derived from an IgG1 hinge (FIG. 4). Primary human T-cells from normal donors were transduced with these CARs and killing of Jurkats and Jurkats with TCR knocked-out were compared. CARs with JOVI-1 scFvs which had either an IgG1 hinge spacer or a CD8 stalk spacer killed Jurkats, but not Jurkats with TCR knockout (FIG. 5), demonstrating the expected specificity. Since the normal donor T-cells transduced with the CARs should have a mixture of TRB1/2 T-cells, it was expected that the cultures would "self-purge". Indeed, this was observed. JOVI-1 staining of the CAR T-cell cultures which become 100% TRBC2 negative in shown in FIG. 6.

Materials & Methods
Demonstration of Specificity of JOVI-1

A tri-cistronic retroviral cassette was generated which coded for a well characterized human TCR as well as a convenient marker gene. The coding sequences for the TCRα and β chains were generated using de-novo gene synthesis from overlapping oligonucleotides. These chains were connected in frame to a foot-and-mouth disease 2A peptide to allow co-expression. The truncated CD34 marker gene was cloned from cDNA by PCR and co-expressed with the TCR chains using an internal ribosome entry sequence (iRES). This cassette was introduced into a retroviral vector. Variants of this construct were generated by splice by over-lap PCR with primers which introduced the desired mutations. The veracity of the constructs was confirmed by Sanger sequencing. The Jurkat 76 line is a well characterized derivate of the Jurkat T-cell line which has both TCR α and β chains knocked out. This Jurkat line was transduced with the above retroviral vectors using standard techniques.

Staining and Analysis of Jurkats, Peripheral Blood T-Cells and Cell Lines

Jurkats were obtained from ECACC and engineered as detailed above. Other T-cell lines were also obtained from ECACC. Peripheral blood was drawn by venopunture from normal donors. Blood was ficolled to isolate mononuclear cells. Cells were stained with JOVI-1 as well as commercially available monoclonal antibodies which recognize all TCRs and CD3. In the case of engineered T-cells, cells were stained with antibodies which recognize CD34. In case of peripheral blood mononuclear cells, cells were stained with antibodies which recognize CD4 and CD8. The antibodies were purchased conjugated with suitable fluorophores so that independent fluorescent signals could be obtained while analyzing the cells with a flow-cytometer.

Demonstration of Specific Lysis of TRBC1 T-Cells

Wild-type Jurkat T-cells (TRBC1-TCR), and Jurkat T-cells TCR KO with TRBC2 TCR introduced were mixed together at a ratio of 1:1. This mixture of Jurkats was then incubated with JOVI-1 monoclonal antibody at 1 ug/ml in the absence or presence of complement. Four hours later, cells were stained with Annexin-V and 7AAD and CD34. Conveniently, the marker gene CD34 can distinguish between wild-type (TRBC1) and transgenic (TRBC2) Jurkats. Cell populations were analysed by flow-cytometry. Live cells were selectively studied by gating on flow cytometric events which are negative for Annexin-V and dim for 7AAD. In this way, the survival of transgenic (TRBC2) vs wild-type (TRBC1) T-cells was studied.

Example 11—Investigating the Clonality of T-Cell Lymphoproliferative Disorders Four patients: three with T-cell large granular lymphocyte lymphoproliferative disorder (T-LGL); and one with peripheral T-cell lymphoma (PCTL) were tested to confirm that malignant cells were uniformly either TRBC1 positive or negative.

Whole blood or bone marrow was collected from patients with T-lymphoproliferative orders. Peripheral blood mononuclear cells (PBMCs) were obtained by Ficoll gradient centrifugation. Freshly obtained PBMCs were pelleted and stained for 20 minutes with appropriate pre-conjugated antibodies. The cells were then washed and resuspended in phosphate buffered saline for immediate flow cytometric analysis on BD LSR Fortessa II. Live lymphocytes were identified by FSc/SSc properties and failure to uptake a dead cell discriminating dye. T-cells were identified by staining with anti-TCR alpha/beta antibody. Tumour and normal T-cell populations were identified using appropriate cell surface stains for each sample, based upon immunophenotype previously identified by clinical laboratory analysis.

The results are shown in FIGS. 18 to 21B.

In patient A (T-LGL, FIG. 18), normal T-cells were CD7bright and contained mixed CD4/CD8 cells, and a mixed population of TRBC1 or TRBC1− cells. In contrast, malignant cells were CD7− or CD7dim, were uniformly CD8+CD4−, and were uniformly TRBC1−.

In patient B (T-LGL, FIG. 19), malignant cells were identified by CD4−, CD8+, CD7+CD57+ and were clonally TRBC1− (highlighted panel). Normal CD4+CD8− and CD4-CD8+ T-cells contained TRBC1+ and TRBC1− populations.

In patient C (T-LGL, FIG. 20), normal CD4+ and CD8+ T-cells populations were 30-40% TRBC1+. Malignant cells were identified by CD4−, CD8+, CD7+CD57+ and were clonally TRBC1+ (highlighted panel, note 84% of cells are TRBC1− remaining 16% likely to be contaminating 'normal' T-cells). Normal CD4+CD8− and CD4-CD8+ T-cells contained TRBC1+ and TRBC1− populations.

In patient D (PTCL-NOS, FIGS. 21A-21B), malignant cells in the bone marrow, identified on the basis of FSChigh CD5dim CD4dim, were uniformly TRBC1+, whereas CD4+CD8− and CD4-CD8+ T-cells contained both TRBC1+ and TRBC1− populations.

Example 12—Generation of Monoclonal Human Antibodies which Distinguish Between the Two Isoforms of the T-Cell Receptor β Chain Constant Domain Using Phage Display In order to generate antibodies which distinguished between TRBC2 and TRBC1 peptide fragments covering the region of difference between the two TRBC isoforms were synthesised. Of the four amino acid differences between TRBC2 and TRBC1, two are found at the beginning of the constant domains. Peptides (see below) representing these regions were synthesised and used for antibody generation.

TRBC2 (SEQ ID No. 36)
VLEDLKNVFPPEVAV

TRBC1 (SEQ ID No. 37)
VLEDLNKVFPPEVAV

These peptides were prepared in biotinylated, non-biotinylated and cysteine modified forms (by addition of a C terminal cysteine). The cysteine modified forms of TRBC1 and TRBC2 were subsequently conjugated to modified bovine serum albumin (Imm-Link BSA, Innova 462-001) or ovalbumin Ovalbumin, Innova 461-001) according to manufacturers recommended conditions.

Results

Antibody Phage Display Selections

Figure 21A:
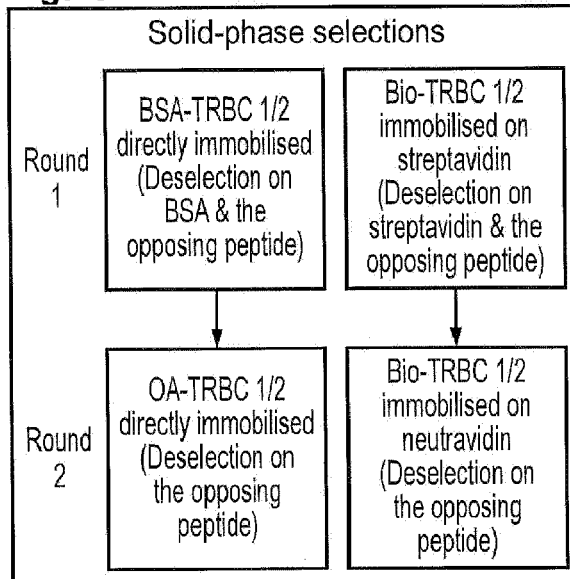
FIGS. 21A-21B: TRBC peptide phage selection strategies.
Figure 21B:
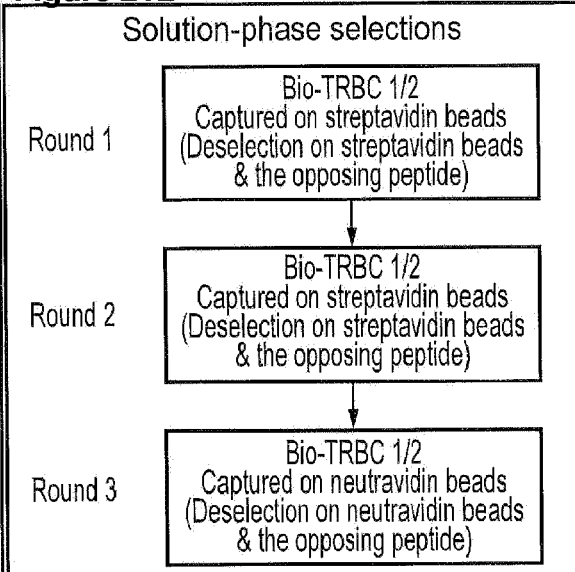

A human phage display library was constructed and phage selections carried out as described in as described in (Schofield et al., 2007 Genome Biol 8, R254). In order to identify TRBC1 and TRBC2 specific antibodies from the antibody library, multiple rounds of phage display selections were carried out. Two phage selection strategies were used in parallel to maximise the chance of generating a large panel of specific binders. These strategies are known as solid phase and solution phase selections (FIGS. 21A-21B). In solid phase selections, phage antibodies are allowed to bind to the target antigen immobilised on a solid surface (Schofield et al., 2007, as above). In solution phase selections, phage antibodies binds to the biotinylated antigen in solution and the phage antibody-antigen complex is then captured by streptavidin or neutravidin coated paramagnetic beads. Within the solid phase selection strategy, two different immobilisation or antigen presentation approaches were employed. Using the first approach, TRBC peptides conjugated to bovine serum albumin (BSA) or ovalbumin (OA) were immobilised on Maxisorp™ immunotubes via direct adsorption. Using the second approach, biotinylated TRBC peptides were immobilised indirectly on Maxisorp™ immunotubes tubes that were pre-coated with streptavidin or neutravidin.

In order to select antibodies that are specific to the desired peptide, all selections were carried out in presence of an excess of the opposing peptide. For example, all TRBC1 selections were carried out in the presence of a 10-fold molar excess of non-biotinylated TRBC2. This method is known as 'deselection' and it was expected to deplete antibodies that recognise shared epitopes on both TRBC peptides as these preferentially bind to the excess TRBC2 in solution. In order to avoid enriching for antibody clones that bind to the carrier protein (BSA or OA) or the immobilisation partner (streptavidin or neutravidin from Thermo fisher scientific) two strategies were employed in combination.

The first strategy was to switch the conjugation or immobilisation partner between rounds of selection. For directly immobilised peptides the first round of selections were carried out on BSA-peptide and for round-2 OA-peptide conjugate was used. Similarly, biotinylated TRBC peptides were immobilised on streptavidin for the round-1 and neutravidin was used for immobilisation in round-2.

The second strategy was to deplete the phage library of any binders to the conjugation/immobilisation partner by performing a 'deselection' in round-1. For directly immobilised peptides, 'deselection was performed by carrying out the phage-peptide binding step in the presence of 10-fold molar excess of free BSA in solution. In the case of biotinylated peptides immobilised on streptavidin, the phage library was pre-incubated with streptavidin coated paramagnetic beads. The beads were removed prior to the addition of the phage to antigen tubes thereby limiting the entry streptavidin binders into the selection. The different selection conditions used are summarised in FIGS. 21A-21B. See Table 3 for detailed information on selection conditions.

Figure 22A:
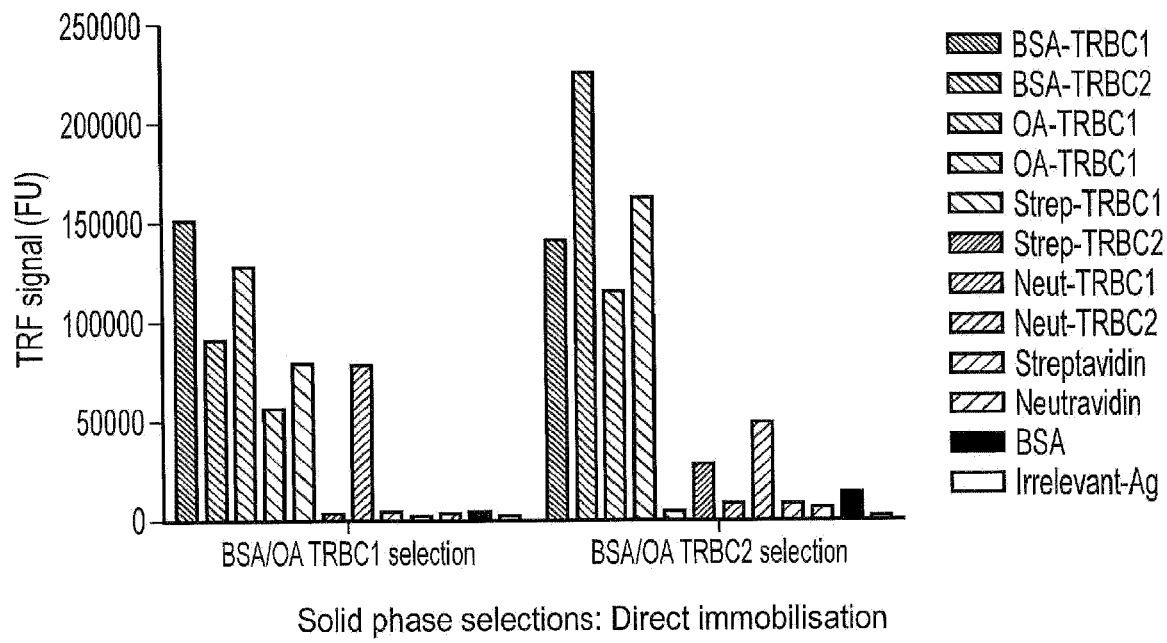
FIGS. 22A-22C: Analysis of polyclonal phage outputs from TRBC peptide phage display selections. TRF binding assay using polyclonal phage from solid phase selections carried out on TRBC peptides directly immobilised as BSA/OA conjugates (FIG. 22A), solid phase selections on TRBC peptides immobilised on streptavidin/neutravidin (FIG. 22B) and from solution phase selections (FIG. 22C).
Figure 22B:
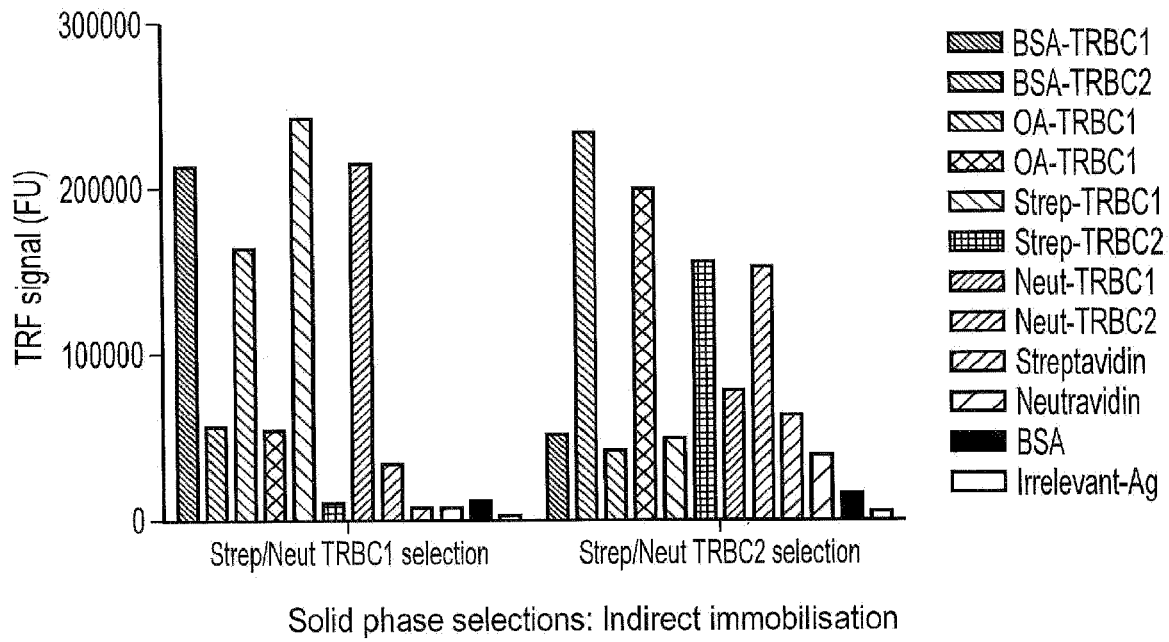
Figure 22C:
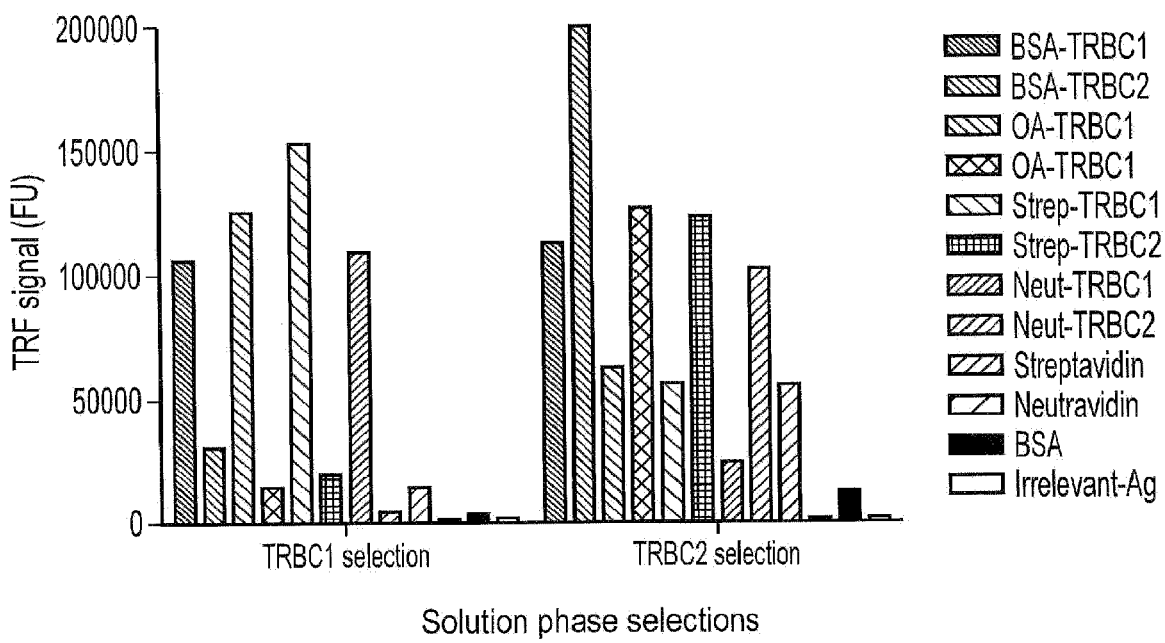
Figure 23:
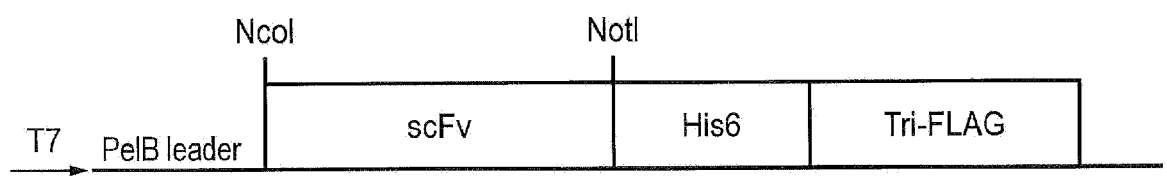
FIG. 23: Schematic representation of pSANG10-3F vector. Gene encoding single chain antibody (scFv) is cloned at NcoI/NotI site downstream of T7 promoter and pelB leader (for periplasmic translocation). The vector also contains a C-terminal hexa-histidine tag (His6) for purification and tri-FLAG tag detection.

Polyclonal phage prepared from round-2 selection output was tested in ELISA using various presentations of the peptides or the support proteins. This included TRBC peptides directly immobilised as either BSA or OA conjugates or biotinylated peptides indirectly immobilised on streptavidin or neutravidin. Control proteins included were streptavidin, neutravidin, BSA and an irrelevant antigen. Phage binding was detected using a mouse anti-M13 antibody (GE healthcare) followed by an anti-mouse Fc antibody labelled with Europium (Perkin Elmers) using time resolved fluorescence (FIGS. 22A-22C). This result demonstrated the preferential binding of polyclonal phage populations to the respective TRBC peptide (as compared to the opposing TRBC peptide). For example, polyclonal phage prepared from TRBC1 selections showed significantly higher binding signal to TRBC1 than TRBC2 and vice versa. There was limited or no binding to the immobilisation or conjugation partners and the irrelevant antigen.

Single Chain Antibody (scFv) Sub-Cloning and Monoclonal Screening

Figure 24A:
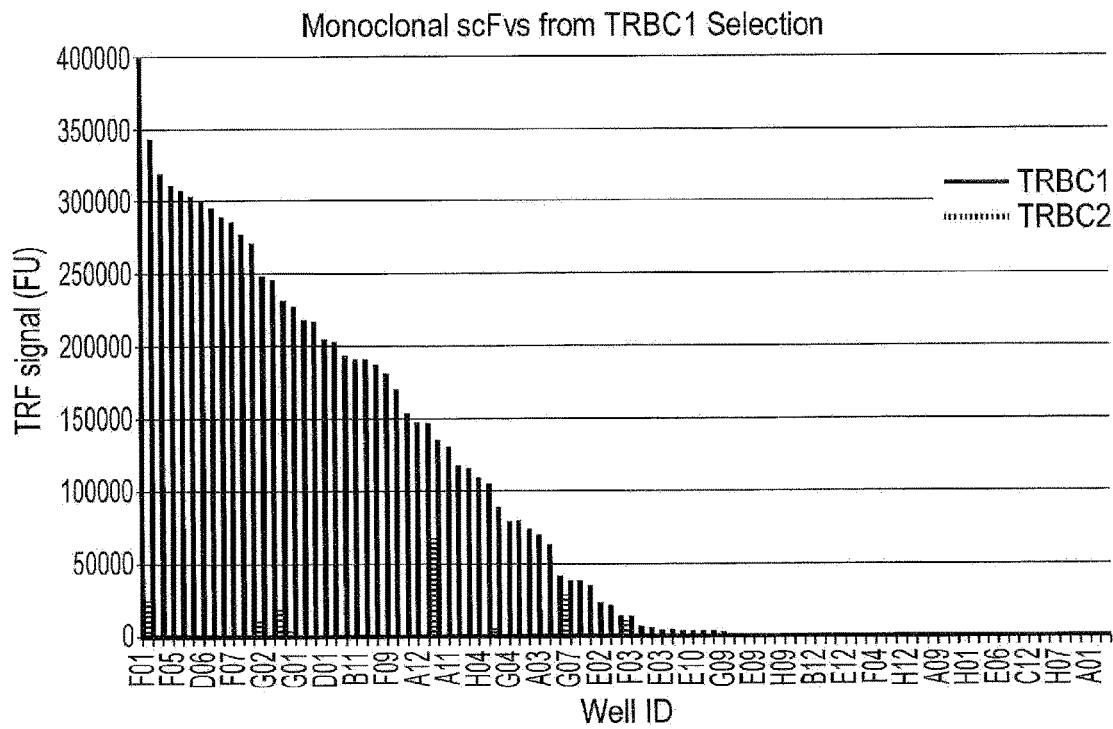
FIGS. 24A-24B: Primary screening for TRBC1 and TRBC2 specific binders. Binding of 94 scFvs from TRBC1 (FIG. 24A) and TRBC2 (FIG. 24B) selections to biotinylated TRBC1 and TRBC2 (0.5 µg/ml) immobilised on neutravidin (10 µg/ml) coated Nunc Maxisorp™ 96 well plates. The scFv binding to the immobilised peptides was detected using an anti-FLAG antibody conjugated to europium.
Figure 24B:
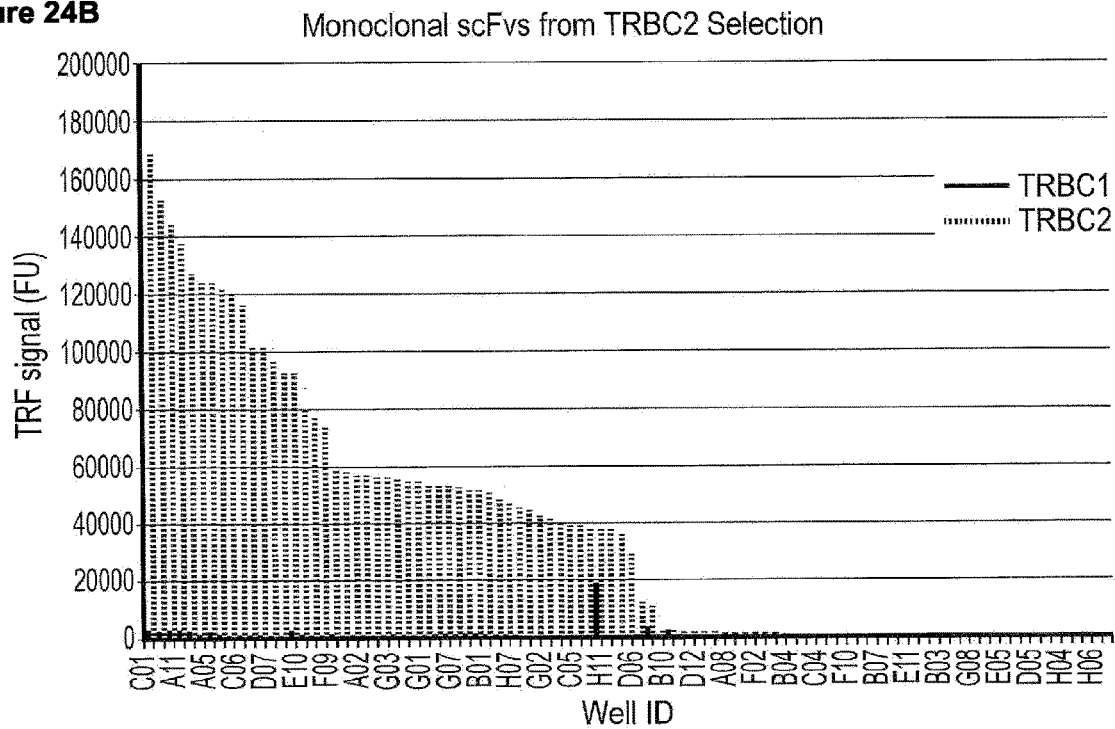
Figure 25A:
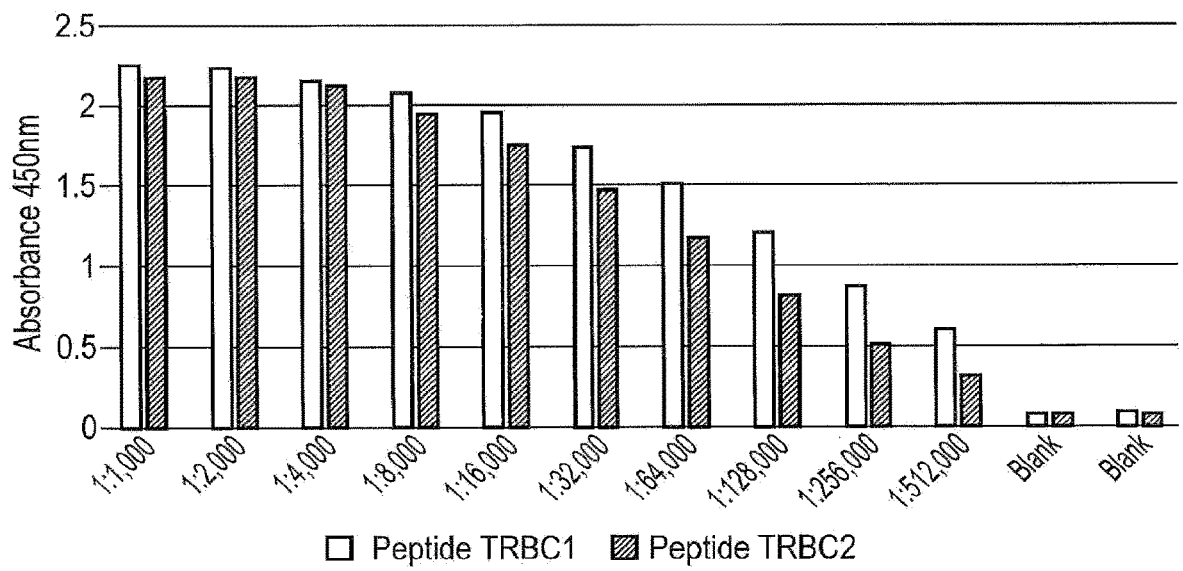
FIGS. 25A-25B: Binding of polyclonal antibody sera from rabbit #13174 immunized with TRBC1 against TRBC1 and TRBC2 peptides.
Figure 25B:
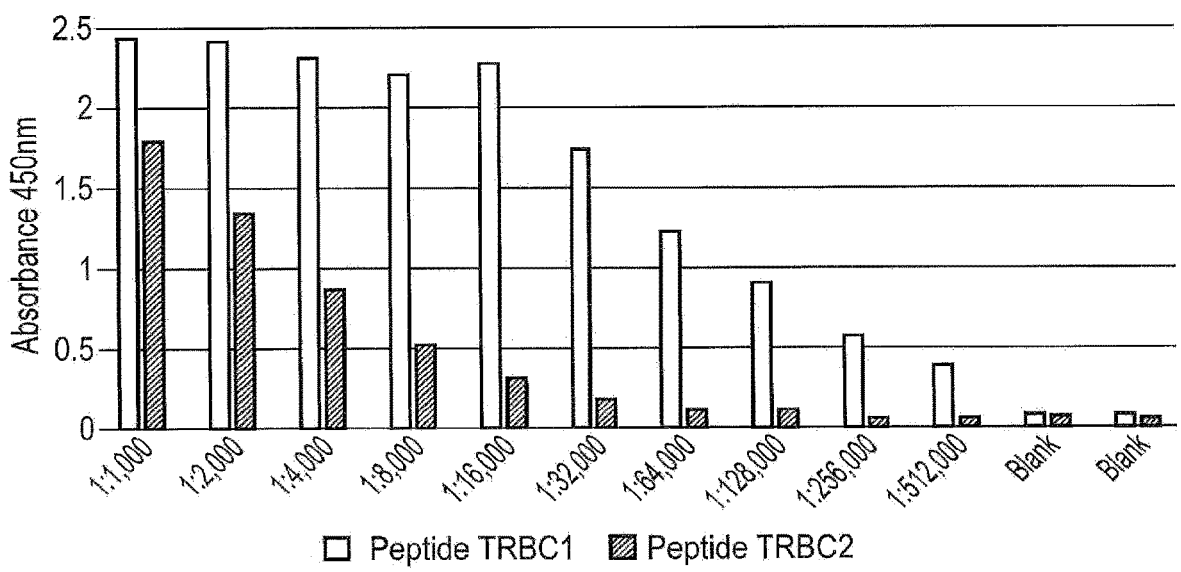
Figure 26A:
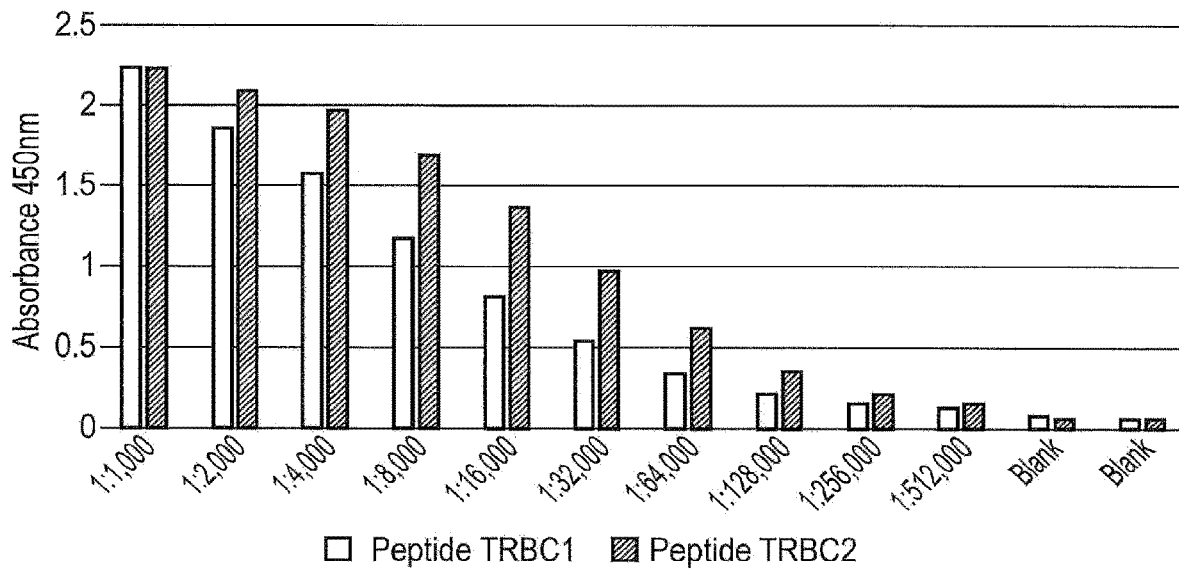
FIGS. 26A-26B: Binding of polyclonal antibody sera from rabbit #17363 immunized with TRBC2 peptide against TRBC1 and TRBC2 peptides.
Figure 26B:
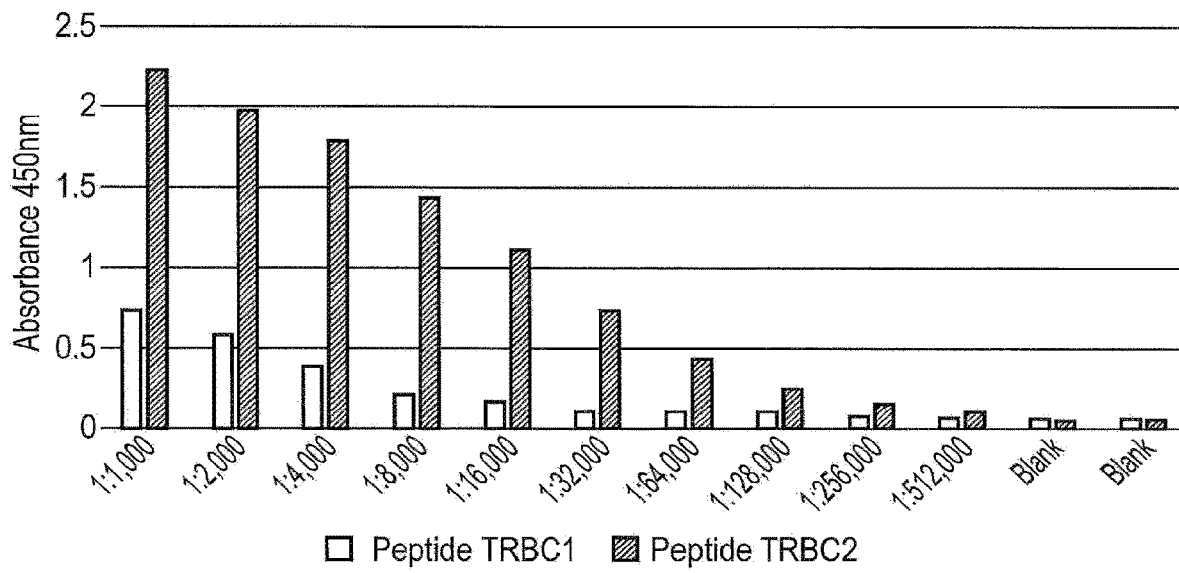
Figure 27A:
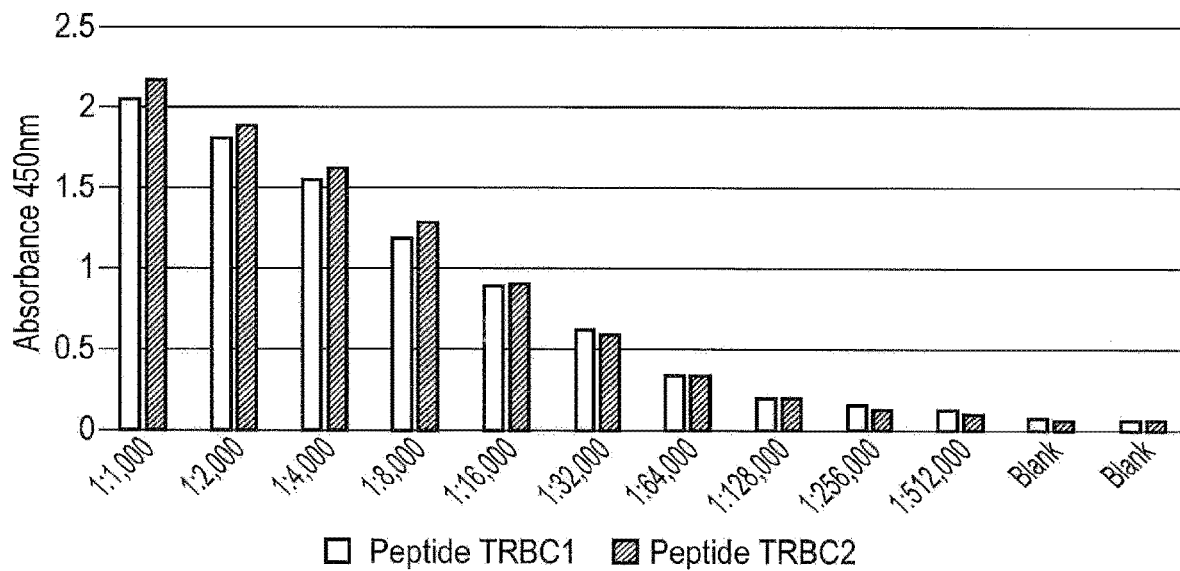
FIGS. 27A-27B: Binding of polyclonal antibody sera from rabbit #17364 immunized with TRBC2 peptide against TRBC1 and TRBC2 peptides.
Figure 27B:
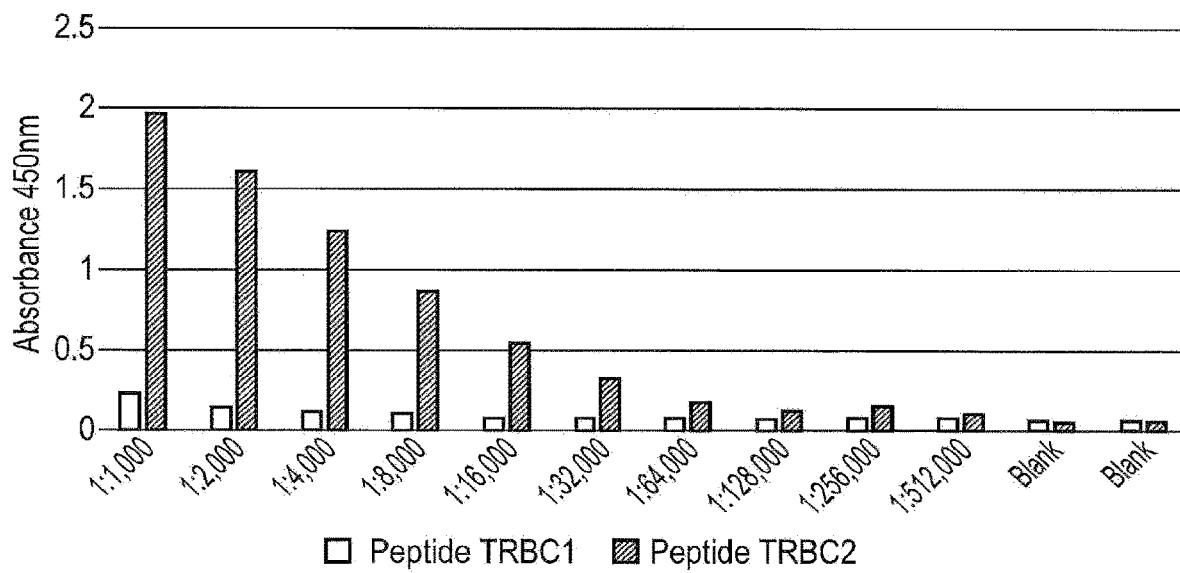

The scFv populations from round-2 and round-3 selection outputs were sub-cloned into the pSANG10-3F expression vector and transformed into *E. coli* BL21 (DE3) cells. 1128 individual transformants (564 clones/TRBC peptide) were picked into 12×96 well culture plates (94 clones/plate) and antibody expression was induced using autoinduction media. Recombinant monoclonal antibodies secreted into culture supernatant after overnight induction were tested for binding to biotinylated TRBC1 and TRBC2 immobilised on neutravidin coated Nunc Maxisorp™ 96 well plates. Out of the 564 clones screened from the TRBC1 selections, 255 clones were found to be specific for TRBC1 (>10000 TRF units for TRBC1 and <1000 TRF units for TRBC2). 138 TRBC2 specific binders (>10000 TRF units for TRBC2 and <2000 TRF units for TRBC1) were identified from the 564 clones screened from the TRBC2 selections. FIGS. 24A-24B shows a representative binding profile from a single 96 well plate arising from selection on either TRBC1 (FIG. 24A) or TRBC2 (FIG. 24B). The details of specific binders generated using different selection conditions is summarised in Table 5.

142 and 138 specific binders were picked from the TRBC1 and TRBC2 selections respectively for sequence analysis and further characterisation. Sequences of cherry-picked clones were generated by Sanger sequencing using BigDye® terminator v3.1 cycle sequencing kit (Life technologies). DNA sequences were analysed to determine protein sequence and the CDRs of the VH and VL domains were identified. Analysis of the VH and VL CDR3 regions identified 74 unique TRBC1 and 42 unique TRBC2 clones (where unique is defined as any combination of VH CDR3 and VL CDR3 sequence). The TRBC1-specific clones and their VH CDR3 and VL CDR3 sequences are summarised in Table 1 above. The TRBC2-specific clones and their VH CDR3 and VL CDR3 sequences are summarised in Table 2 above.

TABLE 3A

Details of solid phase TRBC selections
Solid phase selections

| Selection antigen | No. of rounds | Antigen concentration | Immobilisation | Round 1 deselection antigens | Round 2 deselection antigens |
|---|---|---|---|---|---|
| BSA TRBC1 (Round 1), OA TRBC1 (Round 2) | 2 | 10 µg/ml | Direct | BSA (100 µg/ml), TRBC2 (30 µM) | TRBC2 (30 µM) |
| BSA TRBC2 (Round 1), OA TRBC2 (Round 2) | 2 | 10 µg/ml | Direct | BSA (100 µm/ml), TRBC1 (30 µM) | TRBC1 (30 µM) |
| Bio-TRBC1 (Round 1&2) | 2 | 3 µg/ml | Streptavidin beads (Round 1), Neutravidin (Round 2) | Streptavidin beads, TRBC2 (30 µg/ml) | Neutravidin beads, TRBC2 (30 µg/ml) |
| Bio-TRBC2 (Round 1&2) | 2 | 3 µg/ml | Streptavidin beads (Round 1), Neutravidin (Round 2) | Streptavidin beads, TRBC1 (30 µg/ml) | Neutravidin beads, TRBC1 (30 µg/ml) |

TABLE 3B

Details of solution phase TRBC selections
Solution phase selections

| Selection antigen | No. of rounds | Antigen concentration | Round 1 deselection antigens | Round 2 deselection antigens | Round 3 deselection antigens |
|---|---|---|---|---|---|
| Bio-TRBC1 (Round 1, 2&3) | 3 | 500 nM | Streptavidin beads, TRBC2 (5 μM) | Streptavidin beads, TRBC2 (5 μM) | Neutravidin beads, TRBC2 (5 μM) |
| Bio-TRBC2 (Round 1, 2&3) | 3 | 500 nM | Streptavidin beads, TRBC1 (5 μM) | Streptavidin beads, TRBC1 (5 μM) | Neutravidin beads, TRBC1 (5 μM) |

TABLE 4

Selection output numbers

| Selection type | No. of rounds | Antigen | No. of plaque forming units (Round 1) | No. of plaque forming units (Round 2) | No. of plaque forming units (Round 3) |
|---|---|---|---|---|---|
| Solid phase | 2 | BSA/OA TRBC1 | $1.0 \times 10^4$ | $6.0 \times 10^5$ | N.D |
| Solid phase | 2 | BSA/OA TRBC2 | $1.5 \times 10^3$ | $2.2 \times 10^6$ | N.D |
| Solid phase | 2 | Bio-TRBC1 | $5.0 \times 10^3$ | $2.0 \times 10^5$ | N.D |
| Solid phase | 2 | Bio-TRBC2 | $3.0 \times 10^3$ | $1.0 \times 10^4$ | N.D |
| Solution phase | 3 | Bio-TRBC1 | $1.5 \times 10^6$ | $>10^8$ | $>10^8$ |
| Solution phase | 3 | Bio-TRBC2 | $2.7 \times 10^5$ | $>10^8$ | $>10^8$ |

TABLE 5

Details of monoclonal screening

| Selection number | Selection type | Selection antigen | Selection output | No. of clones screened | No. of specific binders |
|---|---|---|---|---|---|
| 262 | Solid-phase, indirect immobilisation | TRBC1 | Round-2 | 186 | 93 |
| 263 | Solid-phase, indirect immobilisation | TRBC2 | Round-2 | 186 | 68 |
| 264 | Solution-phase | TRBC1 | Round-2 | 186 | 83 |
| 265 | Solution-phase | TRBC2 | Round-2 | 186 | 29 |
| 266 | Solution-phase | TRBC1 | Round-3 | 94 | 47 |
| 267 | Solution-phase | TRBC2 | Round-3 | 94 | 33 |
| 268 | Solid-phase, direct immobilisation (BSA/OA) | TRBC1 | Round-2 | 94 | 32 |
| 269 | Solid-phase, direct immobilisation (BSA/OA) | TRBC2 | Round-2 | 94 | 9 |

Example 13—TRBC Polyclonal Antibody Production Via Peptide Immunisation of Rabbits In order to generate antibodies which distinguish between TRBC2 and TRBC1, 2 peptides that cover the principle area of differentiation between the two TRBC isoforms were synthesized and used for the immunization of rabbits. The following peptide sequences were used:

TRBC1:
(SEQ ID No. 38)
VLEDLNKVFPPEVAVC

TRBC2:
(SEQ ID No. 39)
VLEDLKNVFPPEVAVC 15 mg of TRBC1 and TRBC2 peptides were synthesized. Keyhole Lympet Hemocyanin was conjugated to TRBC1 and TRBC2 peptides via C terminal cysteines present on the peptides. For each peptide 2 New England rabbits were immunized a total of three times with KLH conjugated TRBC1 or TRBC2 peptide. After the third immunization rabbits were sacrificed and bled, and the serum collected for purification. The crude serum obtained from the rabbits were passed through a crosslinked beaded agarose resin column coupled with the peptide used for immunization to collect antibodies specific for the common segments and the TRBC isoform specific epitope of the peptide. The initially purified supernatant was then purified further through a column with the alternative peptide immobilized, to remove the antibodies specific to common segments of the peptide.

ELISA Setup

Coating Antigen(s): A: peptide TRBC1
B: peptide TRBC2
Coating Concentration: 4 ug/ml, 100 μl/well
Coating Buffer: Phosphate Buffered Saline, pH7.4
Secondary Antibody: Anti-RABBIT IgG (H&L) (GOAT) Antibody Peroxidase Conjugated The results are shown in FIGS. 25A-25B and 26A-26B. It is possible to make polyclonal serum comprising TRBC1 or TRBC2-specific antibodies by this method.

The invention claimed is:

1. A method of depleting malignant T-cells in a human subject with a TRBC2 positive T-cell lymphoma or leukaemia, the method comprising:
   determining the percentage of total T-cells in a sample from the subject which is TRBC1 positive and determining the percentage of total T-cells in the sample which is TRBC2 positive,
   detecting a percentage of TRBC1 positive T-cells that is greater than 80% or detecting a percentage of TRBC2 positive T-cells that is greater than 80%,
   diagnosing the subject as having a TRBC2 positive T-cell lymphoma or leukaemia when the percentage of TRBC2 positive cells is greater than 80%, and
   selectively depleting T-cells in the subject determined to have the TRBC2 positive T cell lymphoma or leukaemia by administering an agent that selectively binds to and depletes malignant and normal T cells that are TRBC2-positive,
   wherein the agent is an engineered T-cell expressing a CAR which selectively binds TRBC2 and which comprises: (i) a spacer comprising an IgG1 hinge or a CD8 stalk, and (ii) an endodomain comprising a CD28 co-stimulatory component and a CD3-Zeta component.

2. The method of claim 1 wherein the sample is a peripheral blood sample or a biopsy.

3. A method of selectively depleting TRBC2 positive malignant T-cells without depleting the entire T-cell compartment in a human subject, the method comprising:
   determining whether a malignant T cell in a sample containing T cells from the subject expresses TRBC2, and
   selectively depleting malignant and normal T-cells in the subject that express TRBC2 by administering to the subject an agent that selectively binds to TRBC2 and that depletes said malignant and normal T-cells, wherein the agent is an engineered T-cell expressing a CAR that selectively binds to TRBC2 and that comprises: (i) a spacer comprising an IgG1 hinge or a CD8 stalk, and (ii) an endodomain comprising a CD28 co-stimulatory component and a CD3-Zeta component.

4. The method of claim 3 wherein the malignant T-cells in the subject are T-cell lymphoma or leukaemia cells.

5. The method of claim 4 wherein the malignant T-cells are from a peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

6. The method of claim 1 wherein the malignant T-cells are from a peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

7. The method of claim 1 wherein the IgG1 hinge is an IgG1 hinge altered to remove Fc binding motifs.

8. The method of claim 3 wherein the IgG1 hinge is an IgG1 hinge altered to remove Fc binding motifs.

* * * * *

SEQUENCE LISTING

<160> NUMBER OF SEQ ID NOS: 272

<210> SEQ ID NO 1
<211> LENGTH: 124
<212> TYPE: PRT
<213> ORGANISM: Artificial Sequence
<220> FEATURE:
<223> OTHER INFORMATION: Variable heavy chain (VH) Jovi-1 VH

<400> SEQUENCE: 1

```
Glu Val Arg Leu Gln Gln Ser Gly Pro Asp Leu Ile Lys Pro Gly Ala
1               5                  10                  15

Ser Val Lys Met Ser Cys Lys Ala Ser Gly Tyr Thr Phe Thr Gly Tyr
            20                  25                  30

Val Met His Trp Val Lys Gln Arg Pro Gly Gln Gly Leu Glu Trp Ile
        35                  40                  45

Gly Phe Ile Asn Pro Tyr Asn Asp Asp Ile Gln Ser Asn Glu Arg Phe
    50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser Ser
        115                 120
```

<210> SEQ ID NO 2
<211> LENGTH: 113
<212> TYPE: PRT
<213> ORGANISM: Artificial Sequence
<220> FEATURE:
<223> OTHER INFORMATION: Variable light chain (VL) Jovi-1 VL

<400> SEQUENCE: 2

```
Asp Val Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

Arg
```

<210> SEQ ID NO 3
<211> LENGTH: 252
<212> TYPE: PRT
<213> ORGANISM: Artificial Sequence
<220> FEATURE:
<223> OTHER INFORMATION: Jovi-1 scFv

<400> SEQUENCE: 3

```
Glu Val Arg Leu Gln Gln Ser Gly Pro Asp Leu Ile Lys Pro Gly Ala
1               5                   10                  15

Ser Val Lys Met Ser Cys Lys Ala Ser Gly Tyr Thr Phe Thr Gly Tyr
            20                  25                  30

Val Met His Trp Val Lys Gln Arg Pro Gly Gln Gly Leu Glu Trp Ile
        35                  40                  45

Gly Phe Ile Asn Pro Tyr Asn Asp Asp Ile Gln Ser Asn Glu Arg Phe
    50                  55                  60

Arg Gly Lys Ala Thr Leu Thr Ser Asp Lys Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser Ser Gly Gly Gly Gly
            115                 120                 125

Ser Gly Gly Gly Gly Ser Gly Gly Gly Gly Ser Asp Val Val Met Thr
            130                 135                 140

Gln Ser Pro Leu Ser Leu Pro Val Ser Leu Gly Asp Gln Ala Ser Ile
145                 150                 155                 160

Ser Cys Arg Ser Ser Gln Arg Leu Val His Ser Asn Gly Asn Thr Tyr
                165                 170                 175

Leu His Trp Tyr Leu Gln Lys Pro Gly Gln Ser Pro Lys Leu Leu Ile
            180                 185                 190

Tyr Arg Val Ser Asn Arg Phe Pro Gly Val Pro Asp Arg Phe Ser Gly
            195                 200                 205

Ser Gly Ser Gly Thr Asp Phe Thr Leu Lys Ile Ser Arg Val Glu Ala
210                 215                 220

Glu Asp Leu Gly Ile Tyr Phe Cys Ser Gln Ser Thr His Val Pro Tyr
225                 230                 235                 240

Thr Phe Gly Gly Gly Thr Lys Leu Glu Ile Lys Arg
            245                 250

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 7
<212> TYPE: PRT
<213> ORGANISM: Artificial Sequence
<220> FEATURE:
<223> OTHER INFORMATION: Complementarity determining region (CDR)
      variable heavy chain (VH) CDR1

<400> SEQUENCE: 7
```

```
Gly Tyr Thr Phe Thr Gly Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: VH CDR2

<400> SEQUENCE: 8

Asn Pro Tyr Asn Asp Asp
1               5

<210> SEQ ID NO 9
<211> LENGTH: 15
<212> TYPE: PRT
<213> ORGANISM: Artificial Sequence
<220> FEATURE:
<223> OTHER INFORMATION: VH CDR3

<400> SEQUENCE: 9

Gly Ala Gly Tyr Asn Phe Asp Gly Ala Tyr Arg Phe Phe Asp Phe
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Variable light chain (VL) CDR1

<400> SEQUENCE: 10

Arg Ser Ser Gln Arg Leu Val His Ser Asn Gly Asn Thr Tyr Leu His
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: VL CDR2

<400> SEQUENCE: 11

Arg Val Ser Asn Arg Phe Pro
1               5

<210> SEQ ID NO 12
<211> LENGTH: 9
<212> TYPE: PRT
<213> ORGANISM: Artificial Sequence
<220> FEATURE:
<223> OTHER INFORMATION: VL CDR3

<400> SEQUENCE: 12

Ser Gln Ser Thr His Val Pro Tyr Thr
1               5

<210> SEQ ID NO 13
<211> LENGTH: 247
<212> TYPE: PRT
<213> ORGANISM: Artificial Sequence
<220> FEATURE:
<223> OTHER INFORMATION: Single chain fragment variable (scFv) CP_01_E09

<400> SEQUENCE: 13
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala His Asn Ser Ser Trp Ser Phe Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Ala Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Ser Tyr Leu Asn Trp Tyr Gln Gln Lys Pro Gly
                165                 170                 175

Lys Ala Pro Lys Leu Leu Ile Tyr Asp Ala Ser Asn Leu Glu Thr Gly
            180                 185                 190

Val Pro Ser Arg Phe Ser Gly Ser Gly Ser Gly Thr Asp Phe Thr Phe
        195                 200                 205

Thr Ile Ser Ser Leu Gln Pro Glu Asp Ile Ala Thr Tyr Tyr Cys Gln
    210                 215                 220

Gln Tyr Asp Asn Leu Pro Leu Thr Phe Gly Gly Gly Thr Lys Val Asp
225                 230                 235                 240

Ile Lys Arg Thr Ala Ala Ala
            245

<210> SEQ ID NO 14
<211> LENGTH: 246
<212> TYPE: PRT
<213> ORGANISM: Artificial Sequence
<220> FEATURE:
<223> OTHER INFORMATION: scFv CP_01_D12

<400> SEQUENCE: 14

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Thr Tyr Gly Phe Leu Asp Asn Trp Gly Gln Gly
            100                 105                 110

Thr Met Val Thr Val Ser Ser Gly Gly Gly Ser Gly Gly Gly
            115                 120                 125

Ser Gly Gly Gly Ala Ser Asp Ile Gln Met Thr Gln Ser Pro Ser Thr
        130                 135                 140

Leu Ser Ala Ser Val Gly Asp Arg Val Thr Ile Thr Cys Arg Ala Ser
145                 150                 155                 160

Gln Ser Ile Ser Ser Trp Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Phe Asn Ala Tyr Pro Leu Thr Phe Gly Gly Gly Thr Lys Val Glu Ile
225                 230                 235                 240

Lys Arg Thr Ala Ala Ala
            245

<210> SEQ ID NO 15
<211> LENGTH: 246
<212> TYPE: PRT
<213> ORGANISM: Artificial Sequence
<220> FEATURE:
<223> OTHER INFORMATION: scFv CP_01_D10

<400> SEQUENCE: 15

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Ser Phe Gly Ala Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Ala Ser Asp Ile Gln Met Thr Gln Ser Pro Ser Ser
        130                 135                 140

Leu Ser Ala Ser Val Gly Asp Arg Val Thr Ile Thr Cys Arg Ala Ser
145                 150                 155                 160

Gln Ser Ile Ser Arg Tyr Leu Asn Trp Tyr Gln Gln Lys Pro Gly Lys
                165                 170                 175

Ala Pro Asn Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

```
Tyr Asn Ser Tyr Pro Leu Thr Phe Gly Gly Gly Thr Lys Leu Glu Ile
225                 230                 235                 240

Lys Arg Thr Ala Ala Ala
                245

<210> SEQ ID NO 16
<211> LENGTH: 246
<212> TYPE: PRT
<213> ORGANISM: Artificial Sequence
<220> FEATURE:
<223> OTHER INFORMATION: scFv CP_01_C08

<400> SEQUENCE: 16

Glu Val Gln Leu Leu Glu Ser Gly Gly Gly Ala Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Tyr Ser Ser Ser Trp Tyr Leu Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Ala Ser Asp Ile Gln Met Thr Gln Ser Pro Ser Ser
130                 135                 140

Val Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Tyr Cys Gln Gln
210                 215                 220

Tyr Asp Asn Leu Pro Leu Thr Phe Gly Gly Gly Thr Lys Val Glu Ile
225                 230                 235                 240

Lys Arg Thr Ala Ala Ala
                245

<210> SEQ ID NO 17
<211> LENGTH: 245
<212> TYPE: PRT
<213> ORGANISM: Artificial Sequence
<220> FEATURE:
<223> OTHER INFORMATION: scFv CP_01_C11

<400> SEQUENCE: 17

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30
```

```
Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Ser Gly Gly Ala Gly Trp Asn Trp Gly Gln Gly Thr Met Val Thr
            100                 105                 110

Val Ser Ser Gly Gly Gly Ser Gly Gly Gly Ser Gly Gly Gly Gly Gly
            115                 120                 125

Ala Ser Asn Phe Met Leu Thr Gln Pro His Ser Val Ser Glu Ser Pro
        130                 135                 140

Gly Lys Thr Ala Thr Ile Ser Cys Thr Arg Ser Ser Gly Ser Ile Ala
145                 150                 155                 160

Ser Asn Tyr Val Gln Trp Tyr Gln Gln Arg Pro Gly Ser Ala Pro Thr
                165                 170                 175

Thr Val Ile Tyr Glu Asp Asn Gln Arg Pro Phe Gly Val Pro Asp Arg
            180                 185                 190

Phe Ser Gly Ser Ile Asp Ser Ser Asn Ser Ala Ser Leu Thr Ile
        195                 200                 205

Ser Gly Leu Lys Thr Glu Asp Glu Ala Asp Tyr Tyr Cys Gln Ser His
210                 215                 220

Asp Ser Ser Asn Val Val Phe Gly Gly Gly Thr Gln Leu Thr Val Leu
225                 230                 235                 240

Gly Gln Pro Ala Ala
            245

<210> SEQ ID NO 18
<211> LENGTH: 247
<212> TYPE: PRT
<213> ORGANISM: Artificial Sequence
<220> FEATURE:
<223> OTHER INFORMATION: scFv CP_01_F03
<220> FEATURE:
<221> NAME/KEY: misc_feature
<222> LOCATION: (101)..(101)
<223> OTHER INFORMATION: Xaa can be any naturally occurring amino acid

<400> SEQUENCE: 18

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Xaa Ala Ser Ser Trp Ser Gln Gly Leu Trp Gly Gln
            100                 105                 110

Gly Thr Leu Val Thr Val Ser Ser Gly Gly Gly Gly Ser Gly Gly Gly
```

```
                115                 120                 125
Gly Ser Gly Gly Gly Ala Ser Asp Ile Gln Met Thr Gln Ser Pro Ser
            130                 135                 140

Ser Leu Ser Ala Ser Val Arg Asp Arg Val Thr Ile Thr Cys Gln Ala
145                 150                 155                 160

Ser Gln Asp Ile Ser Asn Tyr Leu Asn Trp Tyr Gln Gln Lys Pro Gly
                165                 170                 175

Lys Ala Pro Lys Leu Leu Ile Tyr Asp Ala Ser Asn Leu Glu Thr Gly
            180                 185                 190

Val Pro Ser Arg Phe Ser Gly Ser Gly Ser Gly Thr Asp Phe Thr Phe
        195                 200                 205

Thr Ile Ser Ser Leu Gln Pro Glu Asp Ile Ala Thr Tyr Tyr Cys Gln
    210                 215                 220

Gln Tyr Asp Asn Leu Pro Pro Thr Phe Gly Gly Gly Thr Lys Val Glu
225                 230                 235                 240

Ile Lys Arg Thr Ala Ala Ala
                245

<210> SEQ ID NO 19
<211> LENGTH: 251
<212> TYPE: PRT
<213> ORGANISM: Artificial Sequence
<220> FEATURE:
<223> OTHER INFORMATION: scFv CP_01_E07

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Gly Ser Gly Gly Ala Phe Asp Ile Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ala Ser Asp Ile Val Met Thr Gln Thr Pro His
            130                 135                 140

Ser Leu Ser Val Thr Pro Gly Gln Pro Ala Ser Ile Ser Cys Lys Ser
145                 150                 155                 160

Ser Gln Ser Leu Leu Tyr Ser Asp Gly Lys Thr Tyr Leu Tyr Trp Tyr
                165                 170                 175

Leu Gln Lys Pro Gly Gln Pro Pro Gln Leu Leu Ile Tyr Glu Val Ser
            180                 185                 190

Asn Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Ser Ile Gln Leu Tyr Thr Phe Gly Gln Gly
```

```
225                 230                 235                 240

Thr Lys Val Asp Ile Lys Arg Thr Ala Ala Ala
                245                 250

<210> SEQ ID NO 20
<211> LENGTH: 244
<212> TYPE: PRT
<213> ORGANISM: Artificial Sequence
<220> FEATURE:
<223> OTHER INFORMATION: scFv CP_01_D03

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Pro Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Lys Gln Tyr Gly Met Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ala Ser Asp Ile Val Met Thr Gln Ser Pro Ala Thr Leu Ser
    130                 135                 140

Leu Ala Pro Gly Glu Arg Ala Thr Leu Ser Cys Arg Ala Ser Gln Ser
145                 150                 155                 160

Val Gly Ser Asn Leu Ala Trp Tyr Gln Gln Lys Pro Gly Gln Ala Pro
                165                 170                 175

Ser Leu Leu Ile Tyr Asp Ala Ser Thr Arg Ala Thr Gly Ile Pro Ala
            180                 185                 190

Arg Phe Ser Gly Ser Gly Ser Gly Thr Asp Phe Thr Leu Thr Ile Ser
        195                 200                 205

Ser Leu Gln Ser Glu Asp Ile Ala Val Tyr Tyr Cys Gln Gln Tyr His
    210                 215                 220

Arg Trp Pro Leu Thr Phe Gly Gly Gly Thr Lys Val Glu Ile Lys Arg
225                 230                 235                 240

Thr Ala Ala Ala

<210> SEQ ID NO 21
<211> LENGTH: 249
<212> TYPE: PRT
<213> ORGANISM: Artificial Sequence
<220> FEATURE:
<223> OTHER INFORMATION: scFv CP_01_F06

<400> SEQUENCE: 21

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
                35                  40                  45
Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asp Gly Ala Met Arg Tyr Trp Gly Gln Gly Thr Met Val
                100                 105                 110

Thr Val Ser Ser Gly Gly Gly Ser Gly Gly Gly Ser Gly Gly
                115                 120                 125

Gly Ala Ser Asp Ile Gln Met Thr Gln Ser Pro Asp Ser Leu Ala Val
                130                 135                 140

Ser Leu Gly Glu Arg Ala Thr Ile Asn Cys Lys Ser Gln Ser Val
 145                 150                 155                 160

Leu Tyr Ser Ser Asn Asn Lys Asn Tyr Leu Ala Trp Tyr Gln Gln Lys
                165                 170                 175

Pro Gly Gln Pro Pro Lys Leu Leu Ile Tyr Trp Ala Ser Thr Arg Glu
                180                 185                 190

Ser Gly Val Pro Asp Arg Phe Ser Gly Ser Gly Ser Gly Thr Asp Phe
                195                 200                 205

Thr Leu Thr Ile Ser Ser Leu Gln Ala Glu Asp Val Ala Val Tyr Tyr
                210                 215                 220

Cys Gln Gln Tyr Tyr Asp Ser Pro Tyr Thr Phe Gly Gln Gly Thr Lys
 225                 230                 235                 240

Val Asp Ile Lys Arg Thr Ala Ala Ala
                245

<210> SEQ ID NO 22
<211> LENGTH: 244
<212> TYPE: PRT
<213> ORGANISM: Artificial Sequence
<220> FEATURE:
<223> OTHER INFORMATION: scFv CP_01_F02

<400> SEQUENCE: 22

Gln Val Gln Leu Val Glu Ser Gly Gly Gly Val Val Gln Pro Gly Arg
 1               5                  10                  15

Pro Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
                 35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Tyr Ser Tyr Ala Asp Tyr Trp Gly Gln Gly Thr Met
                100                 105                 110

Val Thr Val Ser Ser Gly Gly Gly Gly Ser Gly Gly Gly Gly Ser Gly
                115                 120                 125

Gly Gly Ala Ser Asp Ile Gln Met Thr Gln Ser Pro Ser Ser Leu Ser
                130                 135                 140

Ala Ser Val Gly Asp Arg Val Thr Ile Thr Cys Arg Ala Ser Gln Gly
```

145                 150                 155                 160

Ile Arg Asn Asp Leu Gly Trp Tyr Gln Gln Lys Pro Gly Lys Ala Pro
                165                 170                 175

Lys Arg Leu Ile Tyr Ala Ala Ser Ser Leu Gln Ser Gly Val Pro Ser
                180                 185                 190

Arg Phe Ser Gly Ser Gly Ser Gly Thr Glu Phe Thr Leu Thr Ile Ser
                195                 200                 205

Ser Leu Gln Pro Glu Asp Phe Ala Thr Tyr Tyr Cys Leu Gln His Asn
210                 215                 220

Ser Tyr Pro Leu Thr Phe Gly Gly Gly Thr Lys Val Asp Ile Lys Arg
225                 230                 235                 240

Thr Ala Ala Ala

<210> SEQ ID NO 23
<211> LENGTH: 249
<212> TYPE: PRT
<213> ORGANISM: Artificial Sequence
<220> FEATURE:
<223> OTHER INFORMATION: scFv CP_03_E05

<400> SEQUENCE: 23

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Arg Ser Ser Gly Ala Phe Asp Ile Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Ala Ser Asn Phe Met Leu Thr Gln Pro His Ser Val Ser
    130                 135                 140

Glu Ser Pro Gly Lys Thr Val Thr Ile Ser Cys Thr Arg Ser Ser Gly
145                 150                 155                 160

Ser Ile Ala Ser Lys Tyr Val Gln Trp Tyr Gln Gln Arg Pro Gly Ser
                165                 170                 175

Ser Pro Thr Thr Val Ile Tyr Glu Asp Asn Gln Arg Pro Ser Gly Val
            180                 185                 190

Pro Asp Arg Phe Ser Gly Ser Ile Asp Thr Ser Ser Asn Ser Ala Ser
        195                 200                 205

Leu Thr Ile Ser Gly Leu Arg Thr Glu Asp Glu Ala Asp Tyr Tyr Cys
    210                 215                 220

His Ser Tyr Asp Ser Asn Asn His Ser Val Phe Gly Gly Gly Thr Lys
225                 230                 235                 240

Val Thr Val Leu Gly Gln Pro Ala Ala
                245

<210> SEQ ID NO 24

```
<211> LENGTH: 246
<212> TYPE: PRT
<213> ORGANISM: Artificial Sequence
<220> FEATURE:
<223> OTHER INFORMATION: scFv CP_03_D05

<400> SEQUENCE: 24
```

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Pro Arg Gly Arg Gly Ser Ala Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Ala Ser Ser Tyr Glu Leu Thr Gln Pro Pro Ser Val
    130                 135                 140

Ser Val Ser Pro Gly Gln Thr Ala Thr Ile Ser Cys Ser Gly Asp Gln
145                 150                 155                 160

Leu Gly Gly Lys Tyr Gly His Trp Tyr Gln Lys Pro Gly Gln Ser
                165                 170                 175

Pro Val Leu Val Leu Tyr Gln Asp Arg Lys Arg Pro Ala Gly Ile Pro
            180                 185                 190

Glu Arg Phe Ser Gly Ser Ser Ser Gly Asn Thr Ile Thr Leu Thr Ile
        195                 200                 205

Ser Gly Thr Gln Ala Val Asp Glu Ala Asp Tyr Tyr Cys Gln Ala Trp
    210                 215                 220

Asp Thr Asn Leu Gly Gly Val Phe Gly Gly Gly Thr Lys Val Thr Val
225                 230                 235                 240

Leu Gly Gln Pro Ala Ala
                245

```
<210> SEQ ID NO 25
<211> LENGTH: 249
<212> TYPE: PRT
<213> ORGANISM: Artificial Sequence
<220> FEATURE:
<223> OTHER INFORMATION: scFv CP_03_H06

<400> SEQUENCE: 25
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Glu Gly Arg Phe Thr Ile Ser Arg Asp Asn Ala Lys Asn Ser Leu Tyr

```
                65                  70                  75                  80
Leu Gln Met Asn Ser Leu Arg Thr Glu Asp Thr Ala Val Tyr Tyr Cys
                    85                  90                  95

Ala Arg Ala Arg Val Gly Gly Met Asp Val Trp Gly Gln Gly Thr Met
                100                 105                 110

Val Thr Val Ser Ser Gly Gly Gly Gly Ser Gly Gly Gly Gly Ser Gly
                115                 120                 125

Gly Gly Ala Ser Asn Phe Met Leu Thr Gln Pro His Ser Val Ser Glu
        130                 135                 140

Ser Pro Gly Lys Thr Val Thr Ile Ser Cys Thr Arg Ser Ser Gly Ser
145                 150                 155                 160

Ile Ala Ser Asn Tyr Val Gln Trp Tyr Gln Gln Arg Pro Gly Ser Ser
                165                 170                 175

Pro Thr Thr Val Ile Tyr Glu Asp Asn Gln Arg Pro Ser Gly Val Pro
                180                 185                 190

Asp Arg Phe Ser Gly Ser Ile Asp Ser Ser Asn Ser Ala Ser Leu
                195                 200                 205

Thr Ile Ser Gly Leu Lys Thr Glu Asp Glu Ala Asp Tyr Tyr Cys Gln
        210                 215                 220

Ser Phe Asp Ala Asp Asn Leu His Val Val Phe Gly Gly Gly Thr Lys
225                 230                 235                 240

Leu Thr Val Leu Gly Gln Pro Ala Ala
                245

<210> SEQ ID NO 26
<211> LENGTH: 248
<212> TYPE: PRT
<213> ORGANISM: Artificial Sequence
<220> FEATURE:
<223> OTHER INFORMATION: scFv CP_03_C12

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asp Thr Gly Pro Ile Asp Tyr Trp Gly Gln Gly Thr Met Val
                100                 105                 110

Thr Val Ser Ser Gly Gly Gly Gly Ser Gly Gly Gly Gly Ser Gly Gly
            115                 120                 125

Gly Ala Ser Asp Ile Val Met Thr Gln Thr Pro Leu Ser Leu Ser Val
        130                 135                 140

Thr Pro Gly Gln Pro Ala Ser Ile Ser Cys Lys Ser Ser Gln Ser Leu
145                 150                 155                 160

Leu His Ser Asp Gly Lys Thr Tyr Leu Tyr Trp Tyr Leu Gln Lys Pro
                165                 170                 175

Gly Gln Pro Pro Gln Leu Leu Val Tyr Glu Val Ser Asn Arg Phe Ser
```

```
                180                 185                 190
Gly Val Pro Asp Lys Phe Ser Gly Ser Gly Ser Gly Thr Asp Phe Thr
            195                 200                 205

Leu Lys Ile Ser Arg Val Glu Ala Glu Asp Val Gly Val Tyr Tyr Cys
            210                 215                 220

Met Gln Gly Ile Gln Leu Pro Pro Thr Phe Gly Gly Gly Thr Lys Val
225                 230                 235                 240

Asp Ile Lys Arg Thr Ala Ala Ala
                245
```

<210> SEQ ID NO 27
<211> LENGTH: 249
<212> TYPE: PRT
<213> ORGANISM: Artificial Sequence
<220> FEATURE:
<223> OTHER INFORMATION: scFv CP_03_G02

<400> SEQUENCE: 27

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Ile Val Tyr
65                  70                  75                  80

Met Glu Leu Ser Ser Leu Arg Ser Glu Asp Thr Ala Val Tyr Tyr Cys
                85                  90                  95

Ala Arg Gly Val Trp Asn Ser Gly Ser Tyr Leu Gly Phe Asp Tyr Trp
            100                 105                 110

Gly Gln Gly Thr Leu Val Thr Val Ser Ser Gly Gly Gly Gly Ser Gly
        115                 120                 125

Gly Gly Ser Gly Gly Gly Ala Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Gln Ala Ser Gln Asp Ile Ser Asn Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Leu Thr Phe Gly Gly Gly Thr Lys
225                 230                 235                 240

Leu Glu Ile Lys Arg Thr Ala Ala Ala
                245
```

<210> SEQ ID NO 28
<211> LENGTH: 251
<212> TYPE: PRT
<213> ORGANISM: Artificial Sequence
<220> FEATURE:
<223> OTHER INFORMATION: scFv CP_03_D04

<400> SEQUENCE: 28

```
Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Thr Val Pro Gly Gly Ala Phe Asp Ile Trp Gly
            100                 105                 110

Gln Gly Thr Leu Val Thr Val Ser Ser Gly Gly Gly Ser Gly Gly
        115                 120                 125

Gly Gly Ser Gly Gly Gly Ala Ser Asn Phe Met Leu Thr Gln Pro His
    130                 135                 140

Ser Val Ser Asp Ser Pro Gly Lys Thr Val Thr Ile Ser Cys Thr Arg
145                 150                 155                 160

Ser Ser Gly Arg Ile Gly Ser Asn Phe Val Gln Trp Tyr Gln Gln Arg
                165                 170                 175

Pro Gly Ser Ser Pro Thr Thr Val Ile Tyr Glu Asp Asp Gln Arg Pro
            180                 185                 190

Ser Gly Val Pro Ala Arg Phe Ser Gly Ser Ile Asp Ser Ser Ser Asn
        195                 200                 205

Ser Ala Ser Leu Thr Ile Ser Gly Leu Thr Thr Ala Asp Glu Ala Gly
    210                 215                 220

Tyr Tyr Cys Gln Ser Tyr Asp Ala Ser Asn Val Ile Phe Gly Gly Gly
225                 230                 235                 240

Thr Lys Leu Thr Val Leu Gly Gln Pro Ala Ala
                245                 250
```

<210> SEQ ID NO 29
<211> LENGTH: 247
<212> TYPE: PRT
<213> ORGANISM: Artificial Sequence
<220> FEATURE:
<223> OTHER INFORMATION: scFv CP_03_F10

<400> SEQUENCE: 29

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Phe Gly Glu Arg Tyr Ala Phe Asp Ile Trp Gly Gln Gly Thr
            100                 105                 110

Leu Val Thr Val Ser Ser Gly Gly Gly Ser Gly Gly Gly Gly Ser
        115                 120                 125

Gly Gly Gly Ala Ser Gln Ser Glu Leu Thr Gln Pro Pro Ser Ala Ser
        130                 135                 140

Gly Ser Pro Gly Gln Ser Val Thr Ile Ser Cys Thr Gly Thr Ser Thr
145                 150                 155                 160

Asp Val Gly Ala Phe His Phe Val Ser Trp Tyr Gln His Thr Pro Gly
                165                 170                 175

Lys Ala Pro Lys Leu Leu Ile Ser Glu Val Arg Lys Arg Ala Ser Gly
                180                 185                 190

Val Pro Asp Arg Phe Ser Gly Ser Arg Ser Gly Asn Thr Ala Ser Leu
            195                 200                 205

Thr Val Ser Gly Leu Gln Ser Glu Asp Glu Ala Asp Tyr Phe Cys Ser
        210                 215                 220

Ala Tyr Thr Gly Ser Asn Tyr Val Phe Gly Ser Gly Thr Lys Leu Thr
225                 230                 235                 240

Val Leu Gly Gln Pro Ala Ala
            245

<210> SEQ ID NO 30
<211> LENGTH: 252
<212> TYPE: PRT
<213> ORGANISM: Artificial Sequence
<220> FEATURE:
<223> OTHER INFORMATION: scFv CP_03_G09

<400> SEQUENCE: 30

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gln Trp Leu Ala Asn Tyr Tyr Tyr Tyr Gly
            100                 105                 110

Met Asp Val Trp Gly Gln Gly Thr Leu Val Thr Val Ser Ser Gly Gly
        115                 120                 125

Gly Gly Ser Gly Gly Gly Gly Ser Gly Gly Gly Ala Ser Ser Tyr Glu
    130                 135                 140

Leu Thr Gln Pro Leu Ser Val Ser Val Ala Leu Gly Gln Thr Ala Arg
145                 150                 155                 160

Ile Thr Cys Gly Gly Asn Asn Ile Gly Ser Lys Asn Val His Trp Tyr
                165                 170                 175

Gln Gln Lys Pro Gly Gln Ala Pro Val Leu Val Ile Tyr Arg Asp Asn
            180                 185                 190

Asn Arg Pro Ser Gly Ile Pro Glu Arg Phe Ser Gly Ser Asn Ser Gly
        195                 200                 205

```
Asn Thr Ala Thr Leu Thr Ile Ser Lys Ala Gln Ala Gly Asp Glu Ala
        210                 215                 220

Asp Tyr Tyr Cys Gln Val Trp Asp Ser Asn Ser Trp Val Phe Gly Gly
225                 230                 235                 240

Gly Thr Lys Leu Thr Val Leu Gly Gln Pro Ala Ala
            245                 250
```

<210> SEQ ID NO 31
<211> LENGTH: 252
<212> TYPE: PRT
<213> ORGANISM: Artificial Sequence
<220> FEATURE:
<223> OTHER INFORMATION: scFv CP_03_F09

<400> SEQUENCE: 31

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Asp Asp Thr Ala Val Tyr Tyr Cys
                85                  90                  95

Ala Ser Asn Arg Gly Gly Ser Tyr Lys Ser Val Gly Met Asp Val Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ala Ser Asn Phe Met Leu Thr Gln Pro
    130                 135                 140

Gln Ser Val Ser Glu Ser Pro Gly Lys Thr Val Thr Ile Ser Cys Thr
145                 150                 155                 160

Arg Ser Ser Gly Asn Phe Ala Ser Lys Tyr Val Gln Trp Tyr Gln Gln
                165                 170                 175

Arg Pro Gly Ser Ser Pro Thr Thr Val Ile Tyr Glu Asn Tyr Gln Arg
            180                 185                 190

Pro Ser Gly Val Pro Asp Arg Phe Ser Gly Ser Ile Asp Ser Ser Ser
        195                 200                 205

Asn Ser Ala Thr Leu Thr Ile Ser Gly Leu Lys Thr Glu Asp Glu Ala
    210                 215                 220

Asp Tyr Tyr Cys Gln Ser Tyr Asp Glu Val Ser Val Val Phe Gly Gly
225                 230                 235                 240

Gly Thr Gln Leu Thr Val Leu Gly Gln Pro Ala Ala
                245                 250
```

<210> SEQ ID NO 32
<211> LENGTH: 249
<212> TYPE: PRT
<213> ORGANISM: Artificial Sequence
<220> FEATURE:
<223> OTHER INFORMATION: scFv CP_03_D09

<400> SEQUENCE: 32

```
Glu Val Gln Leu Val Gln Ser Gly Ala Glu Val Lys Lys Pro Gly Ser
1               5                   10                  15
```

Ser Val Lys Val Ser Cys Glu Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ser Ser Tyr Gly Met Asp Val Trp Gly Gln Gly Thr
            100                 105                 110

Leu Val Thr Val Ser Ser Gly Gly Gly Ser Gly Gly Gly Gly Ser
        115                 120                 125

Gly Gly Gly Ala Ser Asn Phe Met Leu Thr Gln Pro Leu Ser Val Ser
130                 135                 140

Glu Ser Pro Gly Lys Thr Val Thr Ile Ser Cys Thr Arg Ser Ser Gly
145                 150                 155                 160

Ser Ile Ala Ser Asn Tyr Val Gln Trp Tyr Gln Gln Arg Pro Gly Ser
                165                 170                 175

Ala Pro Thr Thr Val Ile Tyr Glu Asp Asn Gln Arg Pro Ser Gly Val
            180                 185                 190

Pro Asp Arg Phe Ser Gly Ser Ile Asp Ser Ser Ser Asn Ser Ala Ser
        195                 200                 205

Leu Thr Ile Ser Gly Leu Lys Thr Glu Asp Glu Ala Asp Tyr Tyr Cys
    210                 215                 220

Gln Ser Tyr Asn Ser Ser Asn His Trp Val Phe Gly Gly Gly Thr Lys
225                 230                 235                 240

Val Thr Val Leu Gly Gln Pro Ala Ala
            245

<210> SEQ ID NO 33
<211> LENGTH: 537
<212> TYPE: PRT
<213> ORGANISM: Artificial Sequence
<220> FEATURE:
<223> OTHER INFORMATION: Chimeric antigen receptor (CAR), JOVI-1 CAR
      with CD8 stalk spacer

<400> SEQUENCE: 33

Met Glu Thr Asp Thr Leu Leu Leu Trp Val Leu Leu Trp Ile Pro
1               5                   10                  15

Gly Ser Thr Gly Glu Val Arg Leu Gln Gln Ser Gly Pro Asp Leu Ile
            20                  25                  30

Lys Pro Gly Ala Ser Val Lys Met Ser Cys Lys Ala Ser Gly Tyr Thr
        35                  40                  45

Phe Thr Gly Tyr Val Met His Trp Val Lys Gln Arg Pro Gly Gln Gly
    50                  55                  60

Leu Glu Trp Ile Gly Phe Ile Asn Pro Tyr Asn Asp Asp Ile Gln Ser
65                  70                  75                  80

Asn Glu Arg Phe Arg Gly Lys Ala Thr Leu Thr Ser Asp Lys Ser Ser
                85                  90                  95

Thr Thr Ala Tyr Met Glu Leu Ser Ser Leu Thr Ser Glu Asp Ser Ala
            100                 105                 110

Val Tyr Tyr Cys Ala Arg Gly Ala Gly Tyr Asn Phe Asp Gly Ala Tyr

```
            115                 120                 125
Arg Phe Phe Asp Phe Trp Gly Gln Gly Thr Thr Leu Thr Val Ser Ser
130                 135                 140

Gly Gly Gly Gly Ser Gly Gly Gly Ser Gly Gly Gly Gly Ser Asp
145                 150                 155                 160

Val Val Met Thr Gln Ser Pro Leu Ser Leu Pro Val Ser Leu Gly Asp
                165                 170                 175

Gln Ala Ser Ile Ser Cys Arg Ser Ser Gln Arg Leu Val His Ser Asn
                180                 185                 190

Gly Asn Thr Tyr Leu His Trp Tyr Leu Gln Lys Pro Gly Gln Ser Pro
                195                 200                 205

Lys Leu Leu Ile Tyr Arg Val Ser Asn Arg Phe Pro Gly Val Pro Asp
210                 215                 220

Arg Phe Ser Gly Ser Gly Ser Gly Thr Asp Phe Thr Leu Lys Ile Ser
225                 230                 235                 240

Arg Val Glu Ala Glu Asp Leu Gly Ile Tyr Phe Cys Ser Gln Ser Thr
                245                 250                 255

His Val Pro Tyr Thr Phe Gly Gly Gly Thr Lys Leu Glu Ile Lys Arg
                260                 265                 270

Ser Asp Pro Thr Thr Thr Pro Ala Pro Arg Pro Pro Thr Pro Ala Pro
                275                 280                 285

Thr Ile Ala Ser Gln Pro Leu Ser Leu Arg Pro Glu Ala Cys Arg Pro
290                 295                 300

Ala Ala Gly Gly Ala Val His Thr Arg Gly Leu Asp Phe Ala Cys Asp
305                 310                 315                 320

Ile Phe Trp Val Leu Val Val Val Gly Gly Val Leu Ala Cys Tyr Ser
                325                 330                 335

Leu Leu Val Thr Val Ala Phe Ile Ile Phe Trp Val Arg Ser Lys Arg
                340                 345                 350

Ser Arg Leu Leu His Ser Asp Tyr Met Asn Met Thr Pro Arg Arg Pro
                355                 360                 365

Gly Pro Thr Arg Lys His Tyr Gln Pro Tyr Ala Pro Pro Arg Asp Phe
370                 375                 380

Ala Ala Tyr Arg Ser Arg Asp Gln Arg Leu Pro Pro Asp Ala His Lys
385                 390                 395                 400

Pro Pro Gly Gly Gly Ser Phe Arg Thr Pro Ile Gln Glu Glu Gln Ala
                405                 410                 415

Asp Ala His Ser Thr Leu Ala Lys Ile Arg Val Lys Phe Ser Arg Ser
                420                 425                 430

Ala Asp Ala Pro Ala Tyr Gln Gln Gly Gln Asn Gln Leu Tyr Asn Glu
                435                 440                 445

Leu Asn Leu Gly Arg Arg Glu Glu Tyr Asp Val Leu Asp Lys Arg Arg
                450                 455                 460

Gly Arg Asp Pro Glu Met Gly Gly Lys Pro Arg Arg Lys Asn Pro Gln
465                 470                 475                 480

Glu Gly Leu Tyr Asn Glu Leu Gln Lys Asp Lys Met Ala Glu Ala Tyr
                485                 490                 495

Ser Glu Ile Gly Met Lys Gly Glu Arg Arg Arg Gly Lys Gly His Asp
                500                 505                 510

Gly Leu Tyr Gln Gly Leu Ser Thr Ala Thr Lys Asp Thr Tyr Asp Ala
                515                 520                 525

Leu His Met Gln Ala Leu Pro Pro Arg
530                 535
```

<210> SEQ ID NO 34
<211> LENGTH: 727
<212> TYPE: PRT
<213> ORGANISM: Artificial Sequence
<220> FEATURE:
<223> OTHER INFORMATION: JOVI-1 CAR with H-CH2-CH3pvaa spacer

<400> SEQUENCE: 34

```
Met Glu Thr Asp Thr Leu Leu Leu Trp Val Leu Leu Trp Ile Pro
1               5                   10                  15

Gly Ser Thr Gly Glu Val Arg Leu Gln Gln Ser Gly Pro Asp Leu Ile
            20                  25                  30

Lys Pro Gly Ala Ser Val Lys Met Ser Cys Lys Ala Ser Gly Tyr Thr
        35                  40                  45

Phe Thr Gly Tyr Val Met His Trp Val Lys Gln Arg Pro Gly Gln Gly
    50                  55                  60

Leu Glu Trp Ile Gly Phe Ile Asn Pro Tyr Asn Asp Asp Ile Gln Ser
65                  70                  75                  80

Asn Glu Arg Phe Arg Gly Lys Ala Thr Leu Thr Ser Asp Lys Ser Ser
                85                  90                  95

Thr Thr Ala Tyr Met Glu Leu Ser Ser Leu Thr Ser Glu Asp Ser Ala
            100                 105                 110

Val Tyr Tyr Cys Ala Arg Gly Ala Gly Tyr Asn Phe Asp Gly Ala Tyr
        115                 120                 125

Arg Phe Phe Asp Phe Trp Gly Gln Gly Thr Thr Leu Thr Val Ser Ser
    130                 135                 140

Gly Gly Gly Gly Ser Gly Gly Gly Ser Gly Gly Gly Gly Ser Asp
145                 150                 155                 160

Val Val Met Thr Gln Ser Pro Leu Ser Leu Pro Val Ser Leu Gly Asp
                165                 170                 175

Gln Ala Ser Ile Ser Cys Arg Ser Ser Gln Arg Leu Val His Ser Asn
            180                 185                 190

Gly Asn Thr Tyr Leu His Trp Tyr Leu Gln Lys Pro Gly Gln Ser Pro
        195                 200                 205

Lys Leu Leu Ile Tyr Arg Val Ser Asn Arg Phe Pro Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Leu Gly Ile Tyr Phe Cys Ser Gln Ser Thr
                245                 250                 255

His Val Pro Tyr Thr Phe Gly Gly Gly Thr Lys Leu Glu Ile Lys Arg
            260                 265                 270

Ser Asp Pro Ala Glu Pro Lys Ser Pro Asp Lys Thr His Thr Cys Pro
        275                 280                 285

Pro Cys Pro Ala Pro Pro Val Ala Gly Pro Ser Val Phe Leu Phe Pro
    290                 295                 300

Pro Lys Pro Lys Asp Thr Leu Met Ile Ala Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
        355                 360                 365
```

Leu His Gln Asp Trp Leu Asn Gly Lys Glu Tyr Lys Cys Lys Val Ser
            370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Asp
                405                 410                 415

Glu Leu Thr Lys Asn Gln Val Ser Leu Thr Cys Leu Val Lys Gly Phe
            420                 425                 430

Tyr Pro Ser Asp Ile Ala Val Glu Trp Glu Ser Asn Gly Gln Pro Glu
            435                 440                 445

Asn Asn Tyr Lys Thr Thr Pro Pro Val Leu Asp Ser Asp Gly Ser Phe
450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys Lys Asp Pro Lys Phe
            500                 505                 510

Trp Val Leu Val Val Val Gly Gly Val Leu Ala Cys Tyr Ser Leu Leu
            515                 520                 525

Val Thr Val Ala Phe Ile Ile Phe Trp Val Arg Ser Lys Arg Ser Arg
530                 535                 540

Leu Leu His Ser Asp Tyr Met Asn Met Thr Pro Arg Arg Pro Gly Pro
545                 550                 555                 560

Thr Arg Lys His Tyr Gln Pro Tyr Ala Pro Pro Arg Asp Phe Ala Ala
                565                 570                 575

Tyr Arg Ser Arg Asp Gln Arg Leu Pro Pro Asp Ala His Lys Pro Pro
            580                 585                 590

Gly Gly Gly Ser Phe Arg Thr Pro Ile Gln Glu Glu Gln Ala Asp Ala
            595                 600                 605

His Ser Thr Leu Ala Lys Ile Arg Val Lys Phe Ser Arg Ser Ala Asp
            610                 615                 620

Ala Pro Ala Tyr Gln Gln Gly Gln Asn Gln Leu Tyr Asn Glu Leu Asn
625                 630                 635                 640

Leu Gly Arg Arg Glu Glu Tyr Asp Val Leu Asp Lys Arg Arg Gly Arg
                645                 650                 655

Asp Pro Glu Met Gly Gly Lys Pro Arg Arg Lys Asn Pro Gln Glu Gly
            660                 665                 670

Leu Tyr Asn Glu Leu Gln Lys Asp Lys Met Ala Glu Ala Tyr Ser Glu
            675                 680                 685

Ile Gly Met Lys Gly Glu Arg Arg Arg Gly Lys Gly His Asp Gly Leu
            690                 695                 700

Tyr Gln Gly Leu Ser Thr Ala Thr Lys Asp Thr Tyr Asp Ala Leu His
705                 710                 715                 720

Met Gln Ala Leu Pro Pro Arg
                725

<210> SEQ ID NO 35
<211> LENGTH: 511
<212> TYPE: PRT
<213> ORGANISM: Artificial Sequence
<220> FEATURE:
<223> OTHER INFORMATION: JOVI-1 CAR with IgG1 hinge spacer

<400> SEQUENCE: 35

-continued

```
Met Glu Thr Asp Thr Leu Leu Leu Trp Val Leu Leu Val Trp Ile Pro
1               5                   10                  15

Gly Ser Thr Gly Glu Val Arg Leu Gln Gln Ser Gly Pro Asp Leu Ile
            20                  25                  30

Lys Pro Gly Ala Ser Val Lys Met Ser Cys Lys Ala Ser Gly Tyr Thr
            35                  40                  45

Phe Thr Gly Tyr Val Met His Trp Val Lys Gln Arg Pro Gly Gln Gly
        50                  55                  60

Leu Glu Trp Ile Gly Phe Ile Asn Pro Tyr Asn Asp Asp Ile Gln Ser
65                  70                  75                  80

Asn Glu Arg Phe Arg Gly Lys Ala Thr Leu Thr Ser Asp Lys Ser Ser
                85                  90                  95

Thr Thr Ala Tyr Met Glu Leu Ser Ser Leu Thr Ser Glu Asp Ser Ala
            100                 105                 110

Val Tyr Tyr Cys Ala Arg Gly Ala Gly Tyr Asn Phe Asp Gly Ala Tyr
        115                 120                 125

Arg Phe Phe Asp Phe Trp Gly Gln Gly Thr Thr Leu Thr Val Ser Ser
    130                 135                 140

Gly Gly Gly Gly Ser Gly Gly Gly Ser Gly Gly Gly Gly Ser Asp
145                 150                 155                 160

Val Val Met Thr Gln Ser Pro Leu Ser Leu Pro Val Ser Leu Gly Asp
                165                 170                 175

Gln Ala Ser Ile Ser Cys Arg Ser Ser Gln Arg Leu Val His Ser Asn
            180                 185                 190

Gly Asn Thr Tyr Leu His Trp Tyr Leu Gln Lys Pro Gly Gln Ser Pro
            195                 200                 205

Lys Leu Leu Ile Tyr Arg Val Ser Asn Arg Phe Pro Gly Val Pro Asp
        210                 215                 220

Arg Phe Ser Gly Ser Gly Ser Gly Thr Asp Phe Thr Leu Lys Ile Ser
225                 230                 235                 240

Arg Val Glu Ala Glu Asp Leu Gly Ile Tyr Phe Cys Ser Gln Ser Thr
                245                 250                 255

His Val Pro Tyr Thr Phe Gly Gly Gly Thr Lys Leu Glu Ile Lys Arg
            260                 265                 270

Ser Asp Pro Ala Glu Pro Lys Ser Pro Asp Lys Thr His Thr Cys Pro
            275                 280                 285

Pro Cys Pro Lys Asp Pro Lys Phe Trp Val Leu Val Val Val Gly Gly
        290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Asp Gln Arg Leu
        355                 360                 365

Pro Pro Asp Ala His Lys Pro Pro Gly Gly Gly Ser Phe Arg Thr Pro
    370                 375                 380

Ile Gln Glu Glu Gln Ala Asp Ala His Ser Thr Leu Ala Lys Ile Arg
385                 390                 395                 400

Val Lys Phe Ser Arg Ser Ala Asp Ala Pro Ala Tyr Gln Gln Gly Gln
                405                 410                 415
```

Asn Gln Leu Tyr Asn Glu Leu Asn Leu Gly Arg Arg Glu Glu Tyr Asp
               420                 425                 430

Val Leu Asp Lys Arg Arg Gly Asp Pro Glu Met Gly Gly Lys Pro
           435                 440                 445

Arg Arg Lys Asn Pro Gln Glu Gly Leu Tyr Asn Glu Leu Gln Lys Asp
       450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
               485                 490                 495

Lys Asp Thr Tyr Asp Ala Leu His Met Gln Ala Leu Pro Pro Arg
           500                 505                 510

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide for TRBC2

<400> SEQUENCE: 36

Val Leu Glu Asp Leu Lys Asn Val Phe Pro Pro Glu Val Ala Val
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide for TRBC1

<400> SEQUENCE: 37

Val Leu Glu Asp Leu Asn Lys Val Phe Pro Pro Glu Val Ala Val
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic peptide for TRBC1

<400> SEQUENCE: 38

Val Leu Glu Asp Leu Asn Lys Val Phe Pro Pro Glu Val Ala Val Cys
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide for TRBC2

<400> SEQUENCE: 39

Val Leu Glu Asp Leu Lys Asn Val Phe Pro Pro Glu Val Ala Val Cys
1               5                   10                  15

<210> SEQ ID NO 40
<211> LENGTH: 175
<212> TYPE: PRT
<213> ORGANISM: Homo sapiens

<400> SEQUENCE: 40

Asp Leu Asn Lys Val Phe Pro Pro Glu Val Ala Val Phe Glu Pro Ser

```
              1               5                  10                 15
            Glu Ala Glu Ile Ser His Thr Gln Lys Ala Thr Leu Val Cys Leu Ala
                             20                 25                 30
            Thr Gly Phe Phe Pro Asp His Val Glu Leu Ser Trp Trp Val Asn Gly
                         35                 40                 45
            Lys Glu Val His Ser Gly Val Ser Thr Asp Pro Gln Pro Leu Lys Glu
                     50                 55                 60
            Gln Pro Ala Leu Asn Asp Ser Arg Tyr Cys Leu Ser Ser Arg Leu Arg
             65                 70                 75                 80
            Val Ser Ala Thr Phe Trp Gln Asn Pro Arg Asn His Phe Arg Cys Gln
                                 85                 90                 95
            Val Gln Phe Tyr Gly Leu Ser Glu Asn Asp Glu Trp Thr Gln Asp Arg
                             100                105                110
            Ala Lys Pro Val Thr Gln Ile Val Ser Ala Glu Ala Trp Gly Arg Ala
                         115                120                125
            Asp Cys Gly Phe Thr Ser Val Ser Tyr Gln Gln Gly Val Leu Ser Ala
                     130                135                140
            Thr Ile Leu Tyr Glu Ile Leu Leu Gly Lys Ala Thr Leu Tyr Ala Val
            145                150                155                160
            Leu Val Ser Ala Leu Val Leu Met Ala Met Val Lys Arg Lys Asp
                             165                170                175

<210> SEQ ID NO 41
<211> LENGTH: 175
<212> TYPE: PRT
<213> ORGANISM: Homo sapiens

<400> SEQUENCE: 41

Asp Leu Lys Asn Val Phe Pro Pro Glu Val Ala Val Phe Glu Pro Ser
             1               5                  10                 15
            Glu Ala Glu Ile Ser His Thr Gln Lys Ala Thr Leu Val Cys Leu Ala
                             20                 25                 30
            Thr Gly Phe Tyr Pro Asp His Val Glu Leu Ser Trp Trp Val Asn Gly
                         35                 40                 45
            Lys Glu Val His Ser Gly Val Ser Thr Asp Pro Gln Pro Leu Lys Glu
                     50                 55                 60
            Gln Pro Ala Leu Asn Asp Ser Arg Tyr Cys Leu Ser Ser Arg Leu Arg
             65                 70                 75                 80
            Val Ser Ala Thr Phe Trp Gln Asn Pro Arg Asn His Phe Arg Cys Gln
                                 85                 90                 95
            Val Gln Phe Tyr Gly Leu Ser Glu Asn Asp Glu Trp Thr Gln Asp Arg
                             100                105                110
            Ala Lys Pro Val Thr Gln Ile Val Ser Ala Glu Ala Trp Gly Arg Ala
                         115                120                125
            Asp Cys Gly Phe Thr Ser Glu Ser Tyr Gln Gln Gly Val Leu Ser Ala
                     130                135                140
            Thr Ile Leu Tyr Glu Ile Leu Leu Gly Lys Ala Thr Leu Tyr Ala Val
            145                150                155                160
            Leu Val Ser Ala Leu Val Leu Met Ala Met Val Lys Arg Lys Asp
                             165                170                175

<210> SEQ ID NO 42
<211> LENGTH: 9
<212> TYPE: PRT
<213> ORGANISM: Artificial Sequence
<220> FEATURE:
```

```
<223> OTHER INFORMATION: Heavy CDR3 Clone CP_01_E09

<400> SEQUENCE: 42

Ala His Asn Ser Ser Ser Trp Ser Phe
1               5

<210> SEQ ID NO 43
<211> LENGTH: 8
<212> TYPE: PRT
<213> ORGANISM: Artificial Sequence
<220> FEATURE:
<223> OTHER INFORMATION: Heavy CDR3 Clone CP_01_D12

<400> SEQUENCE: 43

Gly Gly Asp Thr Tyr Gly Phe Leu
1               5

<210> SEQ ID NO 44
<211> LENGTH: 8
<212> TYPE: PRT
<213> ORGANISM: Artificial Sequence
<220> FEATURE:
<223> OTHER INFORMATION: Heavy CDR3 Clone CP_01_D10

<400> SEQUENCE: 44

Gly Gly Gly Ser Phe Gly Ala Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Heavy CDR3 Clone CP_01_C08

<400> SEQUENCE: 45

Gly Tyr Ser Ser Ser Trp Tyr Leu
1               5

<210> SEQ ID NO 46
<211> LENGTH: 4
<212> TYPE: PRT
<213> ORGANISM: Artificial Sequence
<220> FEATURE:
<223> OTHER INFORMATION: Heavy CDR3 Clone CP_01_C11

<400> SEQUENCE: 46

Gly Gly Ala Gly
1

<210> SEQ ID NO 47
<211> LENGTH: 9
<212> TYPE: PRT
<213> ORGANISM: Artificial Sequence
<220> FEATURE:
<223> OTHER INFORMATION: Heavy CDR3 Clone CP_01_F03
<220> FEATURE:
<221> NAME/KEY: misc_feature
<222> LOCATION: (3)..(3)
<223> OTHER INFORMATION: Xaa can be any naturally occurring amino acid

<400> SEQUENCE: 47

Gly Tyr Xaa Ala Ser Ser Trp Ser Gln
1               5

<210> SEQ ID NO 48
<211> LENGTH: 9
```

```
<212> TYPE: PRT
<213> ORGANISM: Artificial Sequence
<220> FEATURE:
<223> OTHER INFORMATION: Heavy CDR3 Clone CP_01_E07

<400> SEQUENCE: 48

Asp Leu Gly Gly Ser Gly Gly Ala Phe
1               5

<210> SEQ ID NO 49
<211> LENGTH: 6
<212> TYPE: PRT
<213> ORGANISM: Artificial Sequence
<220> FEATURE:
<223> OTHER INFORMATION: Heavy CDR3 Clone CP_01_D03

<400> SEQUENCE: 49

Asn Lys Gln Tyr Gly Met
1               5

<210> SEQ ID NO 50
<211> LENGTH: 5
<212> TYPE: PRT
<213> ORGANISM: Artificial Sequence
<220> FEATURE:
<223> OTHER INFORMATION: Heavy CDR3 Clone CP_01_F06

<400> SEQUENCE: 50

Asp Asp Gly Ala Met
1               5

<210> SEQ ID NO 51
<211> LENGTH: 6
<212> TYPE: PRT
<213> ORGANISM: Artificial Sequence
<220> FEATURE:
<223> OTHER INFORMATION: Heavy CDR3 Clone CP_01_F02

<400> SEQUENCE: 51

Ala Gly Tyr Ser Tyr Ala
1               5

<210> SEQ ID NO 52
<211> LENGTH: 9
<212> TYPE: PRT
<213> ORGANISM: Artificial Sequence
<220> FEATURE:
<223> OTHER INFORMATION: Heavy CDR3 Clone CP_02_C03

<400> SEQUENCE: 52

Gly Gly Arg Tyr Ser Ser Asn Tyr Phe
1               5

<210> SEQ ID NO 53
<211> LENGTH: 7
<212> TYPE: PRT
<213> ORGANISM: Artificial Sequence
<220> FEATURE:
<223> OTHER INFORMATION: Heavy CDR3 Clone CP_02_D10

<400> SEQUENCE: 53

Val Gly Glu Gly Ser Ala Met
1               5

<210> SEQ ID NO 54
<211> LENGTH: 15
<212> TYPE: PRT
```

```
<213> ORGANISM: Artificial Sequence
<220> FEATURE:
<223> OTHER INFORMATION: Heavy CDR3 Clone CP_02_B01

<400> SEQUENCE: 54

Val Ser Ser His Tyr Asp Ser Ser Gly Tyr Tyr Ala Gly Gly Phe
1               5                   10                  15

<210> SEQ ID NO 55
<211> LENGTH: 9
<212> TYPE: PRT
<213> ORGANISM: Artificial Sequence
<220> FEATURE:
<223> OTHER INFORMATION: Heavy CDR3 Clone CP_02_D02

<400> SEQUENCE: 55

Gly Arg Asp Ser Ser Ser Trp Ser Pro
1               5

<210> SEQ ID NO 56
<211> LENGTH: 9
<212> TYPE: PRT
<213> ORGANISM: Artificial Sequence
<220> FEATURE:
<223> OTHER INFORMATION: Heavy CDR3 Clone CP_02_A02

<400> SEQUENCE: 56

Val Thr Thr Tyr Ser Gly Leu Asp Phe
1               5

<210> SEQ ID NO 57
<211> LENGTH: 10
<212> TYPE: PRT
<213> ORGANISM: Artificial Sequence
<220> FEATURE:
<223> OTHER INFORMATION: Heavy CDR3 Clone CP_02_D04

<400> SEQUENCE: 57

Lys Gly Ala Val Val Val Pro Gly Ala Leu
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Heavy CDR3 Clone CP_01_E10

<400> SEQUENCE: 58

Asn Ser Leu Tyr Gly Gly Asn Ser Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Heavy CDR3 Clone CP_01_H08

<400> SEQUENCE: 59

Asp Gly Gly Gly Gly Arg Phe
1               5

<210> SEQ ID NO 60
<211> LENGTH: 9
<212> TYPE: PRT
<213> ORGANISM: Artificial Sequence
```

```
<220> FEATURE:
<223> OTHER INFORMATION: Heavy CDR3 Clone CP_01_F11

<400> SEQUENCE: 60

Gly Gly Gly Ala Leu Gly Arg Gly Met
1               5

<210> SEQ ID NO 61
<211> LENGTH: 11
<212> TYPE: PRT
<213> ORGANISM: Artificial Sequence
<220> FEATURE:
<223> OTHER INFORMATION: Heavy CDR3 Clone CP_01_F09

<400> SEQUENCE: 61

Leu Leu Arg Ser Gly Gly Gln Ser Tyr Ala Phe
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Heavy CDR3 Clone CP_02_D05

<400> SEQUENCE: 62

Gly Tyr Ser Ser Ser Trp Ser Phe
1               5

<210> SEQ ID NO 63
<211> LENGTH: 8
<212> TYPE: PRT
<213> ORGANISM: Artificial Sequence
<220> FEATURE:
<223> OTHER INFORMATION: Heavy CDR3 Clone CP_02_A09

<400> SEQUENCE: 63

Ala Gly Ser Ser Gly Trp Thr Leu
1               5

<210> SEQ ID NO 64
<211> LENGTH: 6
<212> TYPE: PRT
<213> ORGANISM: Artificial Sequence
<220> FEATURE:
<223> OTHER INFORMATION: Heavy CDR3 Clone CP_02_D03

<400> SEQUENCE: 64

Asp Lys Gly Trp Gly Phe
1               5

<210> SEQ ID NO 65
<211> LENGTH: 11
<212> TYPE: PRT
<213> ORGANISM: Artificial Sequence
<220> FEATURE:
<223> OTHER INFORMATION: Heavy CDR3 Clone CP_02_C11

<400> SEQUENCE: 65

Leu Gly Val Val Arg Gly Val Met Lys Gly Phe
1               5                   10

<210> SEQ ID NO 66
<211> LENGTH: 9
<212> TYPE: PRT
<213> ORGANISM: Artificial Sequence
<220> FEATURE:
```

<223> OTHER INFORMATION: Heavy CDR3 Clone CP_01_H10

<400> SEQUENCE: 66

Ser Ser Tyr Ser Ser Ser Trp Gly Met
1               5

<210> SEQ ID NO 67
<211> LENGTH: 9
<212> TYPE: PRT
<213> ORGANISM: Artificial Sequence
<220> FEATURE:
<223> OTHER INFORMATION: Heavy CDR3 Clone CP_02_C04

<400> SEQUENCE: 67

Ala Asn Ser Trp Ser Ala Gly Gly Met
1               5

<210> SEQ ID NO 68
<211> LENGTH: 9
<212> TYPE: PRT
<213> ORGANISM: Artificial Sequence
<220> FEATURE:
<223> OTHER INFORMATION: Heavy CDR3 Clone CP_01_G03

<400> SEQUENCE: 68

Glu Arg Gly Arg Gly Tyr Ser Tyr Met
1               5

<210> SEQ ID NO 69
<211> LENGTH: 9
<212> TYPE: PRT
<213> ORGANISM: Artificial Sequence
<220> FEATURE:
<223> OTHER INFORMATION: Heavy CDR3 Clone CP_01_G06

<400> SEQUENCE: 69

Val Ala Arg Gly Ile His Asp Ala Phe
1               5

<210> SEQ ID NO 70
<211> LENGTH: 4
<212> TYPE: PRT
<213> ORGANISM: Artificial Sequence
<220> FEATURE:
<223> OTHER INFORMATION: Heavy CDR3 Clone CP_01_D06

<400> SEQUENCE: 70

Arg His Gly Met
1

<210> SEQ ID NO 71
<211> LENGTH: 8
<212> TYPE: PRT
<213> ORGANISM: Artificial Sequence
<220> FEATURE:
<223> OTHER INFORMATION: Heavy CDR3 Clone CP_02_B03

<400> SEQUENCE: 71

Phe Asp Ser Ser Gly Tyr Tyr Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: Heavy CDR3 Clone CP_02_A12

```
<400> SEQUENCE: 72

Asp Leu Val Thr Thr Gly Ala Phe
1               5

<210> SEQ ID NO 73
<211> LENGTH: 12
<212> TYPE: PRT
<213> ORGANISM: Artificial Sequence
<220> FEATURE:
<223> OTHER INFORMATION: Heavy CDR3 Clone CP_01_H03

<400> SEQUENCE: 73

Ala Ile Arg Val Ser Gly Thr Pro Glu Asn Gly Phe
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Heavy CDR3 Clone CP_01_G08

<400> SEQUENCE: 74

Val Arg Ile Thr His Gly Met
1               5

<210> SEQ ID NO 75
<211> LENGTH: 5
<212> TYPE: PRT
<213> ORGANISM: Artificial Sequence
<220> FEATURE:
<223> OTHER INFORMATION: Heavy CDR3 Clone CP_01_A06

<400> SEQUENCE: 75

Gly Lys Leu Ala Phe
1               5

<210> SEQ ID NO 76
<211> LENGTH: 15
<212> TYPE: PRT
<213> ORGANISM: Artificial Sequence
<220> FEATURE:
<223> OTHER INFORMATION: Heavy CDR3 Clone CP_02_A04

<400> SEQUENCE: 76

Asn Gly Asp Ser Ser Gly Tyr His Thr Ser Pro Asn Trp Tyr Phe
1               5                   10                  15

<210> SEQ ID NO 77
<211> LENGTH: 8
<212> TYPE: PRT
<213> ORGANISM: Artificial Sequence
<220> FEATURE:
<223> OTHER INFORMATION: Heavy CDR3 Clone CP_01_E08

<400> SEQUENCE: 77

Val Ser Thr Asp Ser Ser Ser Met
1               5

<210> SEQ ID NO 78
<211> LENGTH: 8
<212> TYPE: PRT
<213> ORGANISM: Artificial Sequence
<220> FEATURE:
<223> OTHER INFORMATION: Heavy CDR3 Clone CP_01_A08
```

```
<400> SEQUENCE: 78

Thr Ser Gln Asp Pro Gly Ala Phe
1               5

<210> SEQ ID NO 79
<211> LENGTH: 11
<212> TYPE: PRT
<213> ORGANISM: Artificial Sequence
<220> FEATURE:
<223> OTHER INFORMATION: Heavy CDR3 Clone CP_01_D01

<400> SEQUENCE: 79

Ala Glu Ser Gly Val Tyr Ser Ser Asn Gly Met
1               5                   10

<210> SEQ ID NO 80
<211> LENGTH: 8
<212> TYPE: PRT
<213> ORGANISM: Artificial Sequence
<220> FEATURE:
<223> OTHER INFORMATION: Heavy CDR3 Clone CP_02_A07

<400> SEQUENCE: 80

Val Asp Arg Val Arg Ser Gly Met
1               5

<210> SEQ ID NO 81
<211> LENGTH: 12
<212> TYPE: PRT
<213> ORGANISM: Artificial Sequence
<220> FEATURE:
<223> OTHER INFORMATION: Heavy CDR3 Clone CP_02_B08

<400> SEQUENCE: 81

Ile Gly Gln Tyr Cys Ser Ser Thr Ser Cys Tyr Met
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Heavy CDR3 Clone CP_01_D09

<400> SEQUENCE: 82

Asp Leu Gly Gly Ser Gly Gly Ala Phe
1               5

<210> SEQ ID NO 83
<211> LENGTH: 7
<212> TYPE: PRT
<213> ORGANISM: Artificial Sequence
<220> FEATURE:
<223> OTHER INFORMATION: Heavy CDR3 Clone CP_01_G07

<400> SEQUENCE: 83

Asp Ser Asp Ala Gly Tyr Phe
1               5

<210> SEQ ID NO 84
<211> LENGTH: 9
<212> TYPE: PRT
<213> ORGANISM: Artificial Sequence
<220> FEATURE:
<223> OTHER INFORMATION: Heavy CDR3 Clone CP_01_A05

<400> SEQUENCE: 84
```

```
Ala Ser Ile Val Ala Ser Gly Ala Phe
1               5

<210> SEQ ID NO 85
<211> LENGTH: 7
<212> TYPE: PRT
<213> ORGANISM: Artificial Sequence
<220> FEATURE:
<223> OTHER INFORMATION: Heavy CDR3 Clone CP_02_A08

<400> SEQUENCE: 85

Ala Gly Gly Ser Asn Ala Phe
1               5

<210> SEQ ID NO 86
<211> LENGTH: 12
<212> TYPE: PRT
<213> ORGANISM: Artificial Sequence
<220> FEATURE:
<223> OTHER INFORMATION: Heavy CDR3 Clone CP_02_D07

<400> SEQUENCE: 86

Val Ser Thr Asp Ser Tyr Gly Arg Gln Asn Trp Phe
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Heavy CDR3 Clone CP_01_C04

<400> SEQUENCE: 87

Gln Tyr Thr Ser Gly Arg Leu Ala Tyr Tyr Tyr His Tyr Met
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Heavy CDR3 Clone CP_01_A07

<400> SEQUENCE: 88

Gly Ile Arg Gly Ala Phe
1               5

<210> SEQ ID NO 89
<211> LENGTH: 8
<212> TYPE: PRT
<213> ORGANISM: Artificial Sequence
<220> FEATURE:
<223> OTHER INFORMATION: Heavy CDR3 Clone CP_01_H02

<400> SEQUENCE: 89

Val Gly Tyr Ser Thr Thr Gln Leu
1               5

<210> SEQ ID NO 90
<211> LENGTH: 8
<212> TYPE: PRT
<213> ORGANISM: Artificial Sequence
<220> FEATURE:
<223> OTHER INFORMATION: Heavy CDR3 Clone CP_01_F10

<400> SEQUENCE: 90
```

-continued

```
Met Ala Gly Ser Tyr Tyr Ala Phe
1               5
```

<210> SEQ ID NO 91
<211> LENGTH: 15
<212> TYPE: PRT
<213> ORGANISM: Artificial Sequence
<220> FEATURE:
<223> OTHER INFORMATION: Heavy CDR3 Clone CP_02_C10

<400> SEQUENCE: 91

```
Val Gly Asp Tyr Tyr Asp Ser Ser Gly Tyr Leu Asp Trp Tyr Phe
1               5                   10                  15
```

<210> SEQ ID NO 92
<211> LENGTH: 9
<212> TYPE: PRT
<213> ORGANISM: Artificial Sequence
<220> FEATURE:
<223> OTHER INFORMATION: Heavy CDR3 Clone CP_02_B05

<400> SEQUENCE: 92

```
Gly Ser Asp Thr Thr Ser Phe Val Ser
1               5
```

<210> SEQ ID NO 93
<211> LENGTH: 8
<212> TYPE: PRT
<213> ORGANISM: Artificial Sequence
<220> FEATURE:
<223> OTHER INFORMATION: Heavy CDR3 Clone CP_01_G04

<400> SEQUENCE: 93

```
Ala Gly His Tyr Tyr Tyr Tyr Met
1               5
```

<210> SEQ ID NO 94
<211> LENGTH: 13
<212> TYPE: PRT
<213> ORGANISM: Artificial Sequence
<220> FEATURE:
<223> OTHER INFORMATION: Heavy CDR3 Clone CP_01_F08

<400> SEQUENCE: 94

```
Val Thr Gly Tyr Pro Asp Tyr Tyr Asp Ser Ser Gly Phe
1               5                   10
```

<210> SEQ ID NO 95
<211> LENGTH: 9
<212> TYPE: PRT
<213> ORGANISM: Artificial Sequence
<220> FEATURE:
<223> OTHER INFORMATION: Heavy CDR3 Clone CP_01_G05

<400> SEQUENCE: 95

```
Val Glu Gly Gly Pro Pro Tyr Tyr Phe
1               5
```

<210> SEQ ID NO 96
<211> LENGTH: 8
<212> TYPE: PRT
<213> ORGANISM: Artificial Sequence
<220> FEATURE:
<223> OTHER INFORMATION: Heavy CDR3 Clone CP_02_A03

<400> SEQUENCE: 96

```
Asn Gly Leu Asp Asn Tyr Gly Met
```

<210> SEQ ID NO 97
<211> LENGTH: 8
<212> TYPE: PRT
<213> ORGANISM: Artificial Sequence
<220> FEATURE:
<223> OTHER INFORMATION: Heavy CDR3 Clone CP_01_B09

<400> SEQUENCE: 97

Leu Gly Thr Thr Lys Arg Ala Phe
1               5

<210> SEQ ID NO 98
<211> LENGTH: 8
<212> TYPE: PRT
<213> ORGANISM: Artificial Sequence
<220> FEATURE:
<223> OTHER INFORMATION: Heavy CDR3 Clone CP_01_A10

<400> SEQUENCE: 98

Val Tyr Val Asp His Glu Gly Met
1               5

<210> SEQ ID NO 99
<211> LENGTH: 6
<212> TYPE: PRT
<213> ORGANISM: Artificial Sequence
<220> FEATURE:
<223> OTHER INFORMATION: Heavy CDR3 Clone CP_01_H04

<400> SEQUENCE: 99

Trp Ser Gly Ser Gly Phe
1               5

<210> SEQ ID NO 100
<211> LENGTH: 8
<212> TYPE: PRT
<213> ORGANISM: Artificial Sequence
<220> FEATURE:
<223> OTHER INFORMATION: Heavy CDR3 Clone CP_02_B04

<400> SEQUENCE: 100

Asp Phe Gly Trp Gly Gly Ala Phe
1               5

<210> SEQ ID NO 101
<211> LENGTH: 7
<212> TYPE: PRT
<213> ORGANISM: Artificial Sequence
<220> FEATURE:
<223> OTHER INFORMATION: Heavy CDR3 Clone CP_02_A05

<400> SEQUENCE: 101

Val Val Gly Gly Thr Gln His
1               5

<210> SEQ ID NO 102
<211> LENGTH: 14
<212> TYPE: PRT
<213> ORGANISM: Artificial Sequence
<220> FEATURE:
<223> OTHER INFORMATION: Heavy CDR3 Clone CP_01_F07

<400> SEQUENCE: 102

Asn Trp Leu Leu Tyr Tyr Gly Asp Pro Gln Gln Asn Ala Phe
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Heavy CDR3 Clone CP_01_H01

<400> SEQUENCE: 103

Leu Tyr Phe Asp Trp Phe Ala Asp Ser Gln Asn Ala Phe
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Heavy CDR3 Clone CP_01_G10

<400> SEQUENCE: 104

Val Gly Tyr Gln Pro Leu Leu Tyr Ala Asp Tyr Tyr Phe
1               5                   10

<210> SEQ ID NO 105
<211> LENGTH: 5
<212> TYPE: PRT
<213> ORGANISM: Artificial Sequence
<220> FEATURE:
<223> OTHER INFORMATION: Heavy CDR3 Clone CP_01_G11

<400> SEQUENCE: 105

Gly Ala Met Gly Leu
1               5

<210> SEQ ID NO 106
<211> LENGTH: 10
<212> TYPE: PRT
<213> ORGANISM: Artificial Sequence
<220> FEATURE:
<223> OTHER INFORMATION: Heavy CDR3 Clone CP_01_G01

<400> SEQUENCE: 106

Val Tyr Tyr Leu Ser Gly Val His Ala Phe
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Heavy CDR3 Clone CP_01_A12

<400> SEQUENCE: 107

Thr Glu Arg Trp Leu Gln Phe
1               5

<210> SEQ ID NO 108
<211> LENGTH: 6
<212> TYPE: PRT
<213> ORGANISM: Artificial Sequence
<220> FEATURE:
<223> OTHER INFORMATION: Heavy CDR3 Clone CP_01_H05

<400> SEQUENCE: 108

Asn Gly Asp Tyr Ala Phe
1               5

<210> SEQ ID NO 109
<211> LENGTH: 10
<212> TYPE: PRT
<213> ORGANISM: Artificial Sequence
<220> FEATURE:
<223> OTHER INFORMATION: Heavy CDR3 Clone CP_02_B07

<400> SEQUENCE: 109

Ala Ser Arg Tyr Ser Gly Ser Tyr His Phe
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Heavy CDR3 Clone CP_01_G09

<400> SEQUENCE: 110

His Gly Ser Gln Gly Gly Phe
1               5

<210> SEQ ID NO 111
<211> LENGTH: 7
<212> TYPE: PRT
<213> ORGANISM: Artificial Sequence
<220> FEATURE:
<223> OTHER INFORMATION: Heavy CDR3 Clone CP_02_C02

<400> SEQUENCE: 111

Val Gly Tyr Met Gly Gly Met
1               5

<210> SEQ ID NO 112
<211> LENGTH: 10
<212> TYPE: PRT
<213> ORGANISM: Artificial Sequence
<220> FEATURE:
<223> OTHER INFORMATION: Heavy CDR3 Clone CP_01_D05

<400> SEQUENCE: 112

Asn Thr Pro Gly Ile Ala Ala Ala Gly Pro
1               5                   10

<210> SEQ ID NO 113
<211> LENGTH: 9
<212> TYPE: PRT
<213> ORGANISM: Artificial Sequence
<220> FEATURE:
<223> OTHER INFORMATION: Heavy CDR3 Clone CP_01_D08

<400> SEQUENCE: 113

Val Gly Thr Thr Thr Val Thr Ser Phe
1               5

<210> SEQ ID NO 114
<211> LENGTH: 9
<212> TYPE: PRT
<213> ORGANISM: Artificial Sequence
<220> FEATURE:
<223> OTHER INFORMATION: Heavy CDR3 Clone CP_02_A11

<400> SEQUENCE: 114

Val Gly Gly Pro Leu Asn Asp Ala Phe
1               5

<210> SEQ ID NO 115
<211> LENGTH: 7
<212> TYPE: PRT
<213> ORGANISM: Artificial Sequence
<220> FEATURE:
<223> OTHER INFORMATION: Heavy CDR3 Clone CP_02_D08

<400> SEQUENCE: 115

His Ser Ser Gly Gly Ala Phe
1               5

<210> SEQ ID NO 116
<211> LENGTH: 7
<212> TYPE: PRT
<213> ORGANISM: Artificial Sequence
<220> FEATURE:
<223> OTHER INFORMATION: Light CDR3 Clone CP_01_E09

<400> SEQUENCE: 116

Gln Gln Tyr Asp Asn Leu Pro
1               5

<210> SEQ ID NO 117
<211> LENGTH: 7
<212> TYPE: PRT
<213> ORGANISM: Artificial Sequence
<220> FEATURE:
<223> OTHER INFORMATION: Light CDR3 Clone CP_01_D12

<400> SEQUENCE: 117

Gln Gln Phe Asn Ala Tyr Pro
1               5

<210> SEQ ID NO 118
<211> LENGTH: 7
<212> TYPE: PRT
<213> ORGANISM: Artificial Sequence
<220> FEATURE:
<223> OTHER INFORMATION: Light CDR3 Clone CP_01_D10

<400> SEQUENCE: 118

Gln Gln Tyr Asn Ser Tyr Pro
1               5

<210> SEQ ID NO 119
<211> LENGTH: 7
<212> TYPE: PRT
<213> ORGANISM: Artificial Sequence
<220> FEATURE:
<223> OTHER INFORMATION: Light CDR3 Clone CP_01_C08

<400> SEQUENCE: 119

Gln Gln Tyr Asp Asn Leu Pro
1               5

<210> SEQ ID NO 120
<211> LENGTH: 7
<212> TYPE: PRT
<213> ORGANISM: Artificial Sequence
<220> FEATURE:
<223> OTHER INFORMATION: Light CDR3 Clone CP_01_C11

<400> SEQUENCE: 120

Gln Ser His Asp Ser Ser Asn
1               5

<210> SEQ ID NO 121

```
<211> LENGTH: 7
<212> TYPE: PRT
<213> ORGANISM: Artificial Sequence
<220> FEATURE:
<223> OTHER INFORMATION: Light CDR3 Clone CP_01_F03

<400> SEQUENCE: 121

Gln Gln Tyr Asp Asn Leu Pro
1               5

<210> SEQ ID NO 122
<211> LENGTH: 6
<212> TYPE: PRT
<213> ORGANISM: Artificial Sequence
<220> FEATURE:
<223> OTHER INFORMATION: Light CDR3 Clone CP_01_E07

<400> SEQUENCE: 122

Met Gln Ser Ile Gln Leu
1               5

<210> SEQ ID NO 123
<211> LENGTH: 7
<212> TYPE: PRT
<213> ORGANISM: Artificial Sequence
<220> FEATURE:
<223> OTHER INFORMATION: Light CDR3 Clone CP_01_D03

<400> SEQUENCE: 123

Gln Gln Tyr His Arg Trp Pro
1               5

<210> SEQ ID NO 124
<211> LENGTH: 7
<212> TYPE: PRT
<213> ORGANISM: Artificial Sequence
<220> FEATURE:
<223> OTHER INFORMATION: Light CDR3 Clone CP_01_F06

<400> SEQUENCE: 124

Gln Gln Tyr Tyr Asp Ser Pro
1               5

<210> SEQ ID NO 125
<211> LENGTH: 7
<212> TYPE: PRT
<213> ORGANISM: Artificial Sequence
<220> FEATURE:
<223> OTHER INFORMATION: Light CDR3 Clone CP_01_F02

<400> SEQUENCE: 125

Leu Gln His Asn Ser Tyr Pro
1               5

<210> SEQ ID NO 126
<211> LENGTH: 6
<212> TYPE: PRT
<213> ORGANISM: Artificial Sequence
<220> FEATURE:
<223> OTHER INFORMATION: Light CDR3 Clone CP_02_C03

<400> SEQUENCE: 126

Gln Gln Tyr Phe Gly Thr
1               5

<210> SEQ ID NO 127
<211> LENGTH: 7
```

```
<212> TYPE: PRT
<213> ORGANISM: Artificial Sequence
<220> FEATURE:
<223> OTHER INFORMATION: Light CDR3 Clone CP_02_D10

<400> SEQUENCE: 127

Gln Gln Tyr Asn Asp Trp Pro
1               5

<210> SEQ ID NO 128
<211> LENGTH: 8
<212> TYPE: PRT
<213> ORGANISM: Artificial Sequence
<220> FEATURE:
<223> OTHER INFORMATION: Light CDR3 Clone CP_02_B01

<400> SEQUENCE: 128

Gln Ser Phe Asp Thr Asn Ser Leu
1               5

<210> SEQ ID NO 129
<211> LENGTH: 7
<212> TYPE: PRT
<213> ORGANISM: Artificial Sequence
<220> FEATURE:
<223> OTHER INFORMATION: Light CDR3 Clone CP_02_D02

<400> SEQUENCE: 129

Gln Gln Tyr Asp Asn Leu Pro
1               5

<210> SEQ ID NO 130
<211> LENGTH: 8
<212> TYPE: PRT
<213> ORGANISM: Artificial Sequence
<220> FEATURE:
<223> OTHER INFORMATION: Light CDR3 Clone CP_02_A02

<400> SEQUENCE: 130

Ser Ser Tyr Thr Ser Ser Ser Thr
1               5

<210> SEQ ID NO 131
<211> LENGTH: 7
<212> TYPE: PRT
<213> ORGANISM: Artificial Sequence
<220> FEATURE:
<223> OTHER INFORMATION: Light CDR3 Clone CP_02_D04

<400> SEQUENCE: 131

Gln Gln Tyr Asn Ser Tyr Pro
1               5

<210> SEQ ID NO 132
<211> LENGTH: 7
<212> TYPE: PRT
<213> ORGANISM: Artificial Sequence
<220> FEATURE:
<223> OTHER INFORMATION: Light CDR3 Clone CP_01_E10

<400> SEQUENCE: 132

Gln Gln Thr Phe Thr Thr Pro
1               5

<210> SEQ ID NO 133
<211> LENGTH: 7
<212> TYPE: PRT
```

```
<213> ORGANISM: Artificial Sequence
<220> FEATURE:
<223> OTHER INFORMATION: Light CDR3 Clone CP_01_H08

<400> SEQUENCE: 133

Gln Gln Tyr Asp Asn Leu Pro
1               5

<210> SEQ ID NO 134
<211> LENGTH: 7
<212> TYPE: PRT
<213> ORGANISM: Artificial Sequence
<220> FEATURE:
<223> OTHER INFORMATION: Light CDR3 Clone CP_01_F11

<400> SEQUENCE: 134

Gln Ser Tyr Asp Thr Asn Asn
1               5

<210> SEQ ID NO 135
<211> LENGTH: 7
<212> TYPE: PRT
<213> ORGANISM: Artificial Sequence
<220> FEATURE:
<223> OTHER INFORMATION: Light CDR3 Clone CP_01_F09

<400> SEQUENCE: 135

Gln Gln Ser Tyr Ser Thr Pro
1               5

<210> SEQ ID NO 136
<211> LENGTH: 7
<212> TYPE: PRT
<213> ORGANISM: Artificial Sequence
<220> FEATURE:
<223> OTHER INFORMATION: Light CDR3 Clone CP_02_D05

<400> SEQUENCE: 136

Gln Gln Tyr Asp Asn Leu Pro
1               5

<210> SEQ ID NO 137
<211> LENGTH: 7
<212> TYPE: PRT
<213> ORGANISM: Artificial Sequence
<220> FEATURE:
<223> OTHER INFORMATION: Light CDR3 Clone CP_02_A09

<400> SEQUENCE: 137

Gln Gln Tyr Asp Asn Leu Pro
1               5

<210> SEQ ID NO 138
<211> LENGTH: 7
<212> TYPE: PRT
<213> ORGANISM: Artificial Sequence
<220> FEATURE:
<223> OTHER INFORMATION: Light CDR3 Clone CP_02_D03

<400> SEQUENCE: 138

Gln Gln Tyr Asp Asn Leu Pro
1               5

<210> SEQ ID NO 139
<211> LENGTH: 7
<212> TYPE: PRT
<213> ORGANISM: Artificial Sequence
```

```
<220> FEATURE:
<223> OTHER INFORMATION: Light CDR3 Clone CP_02_C11

<400> SEQUENCE: 139

Gln Ser Tyr Asp Ser Ser Asn
1               5

<210> SEQ ID NO 140
<211> LENGTH: 7
<212> TYPE: PRT
<213> ORGANISM: Artificial Sequence
<220> FEATURE:
<223> OTHER INFORMATION: Light CDR3 Clone CP_01_H10

<400> SEQUENCE: 140

Gln Gln Tyr Asp Asn Leu Pro
1               5

<210> SEQ ID NO 141
<211> LENGTH: 7
<212> TYPE: PRT
<213> ORGANISM: Artificial Sequence
<220> FEATURE:
<223> OTHER INFORMATION: Light CDR3 Clone CP_02_C04

<400> SEQUENCE: 141

Gln Gln Tyr Asp Asp Leu Pro
1               5

<210> SEQ ID NO 142
<211> LENGTH: 7
<212> TYPE: PRT
<213> ORGANISM: Artificial Sequence
<220> FEATURE:
<223> OTHER INFORMATION: Light CDR3 Clone CP_01_G03

<400> SEQUENCE: 142

Met Gln Arg Ile Glu Phe Pro
1               5

<210> SEQ ID NO 143
<211> LENGTH: 8
<212> TYPE: PRT
<213> ORGANISM: Artificial Sequence
<220> FEATURE:
<223> OTHER INFORMATION: Light CDR3 Clone CP_01_G06

<400> SEQUENCE: 143

Gln Ser Tyr Asp Asn Thr Arg His
1               5

<210> SEQ ID NO 144
<211> LENGTH: 7
<212> TYPE: PRT
<213> ORGANISM: Artificial Sequence
<220> FEATURE:
<223> OTHER INFORMATION: Light CDR3 Clone CP_01_D06

<400> SEQUENCE: 144

Gln Ser Tyr Asp Ser Ser Asn
1               5

<210> SEQ ID NO 145
<211> LENGTH: 7
<212> TYPE: PRT
<213> ORGANISM: Artificial Sequence
<220> FEATURE:
```

```
<223> OTHER INFORMATION: Light CDR3 Clone CP_02_B03

<400> SEQUENCE: 145

Gln Ser Tyr Asp Ser Ser Asn
1               5

<210> SEQ ID NO 146
<211> LENGTH: 7
<212> TYPE: PRT
<213> ORGANISM: Artificial Sequence
<220> FEATURE:
<223> OTHER INFORMATION: Light CDR3 Clone CP_02_A12

<400> SEQUENCE: 146

Gln Gln His Asn Asp Trp Pro
1               5

<210> SEQ ID NO 147
<211> LENGTH: 8
<212> TYPE: PRT
<213> ORGANISM: Artificial Sequence
<220> FEATURE:
<223> OTHER INFORMATION: Light CDR3 Clone CP_01_H03

<400> SEQUENCE: 147

Gln Ser Tyr His Ser Ser Asn Leu
1               5

<210> SEQ ID NO 148
<211> LENGTH: 7
<212> TYPE: PRT
<213> ORGANISM: Artificial Sequence
<220> FEATURE:
<223> OTHER INFORMATION: Light CDR3 Clone CP_01_G08

<400> SEQUENCE: 148

Met Gln Ala Thr His Phe Pro
1               5

<210> SEQ ID NO 149
<211> LENGTH: 7
<212> TYPE: PRT
<213> ORGANISM: Artificial Sequence
<220> FEATURE:
<223> OTHER INFORMATION: Light CDR3 Clone CP_01_A06

<400> SEQUENCE: 149

Gln Gln Tyr Tyr Ser Thr Pro
1               5

<210> SEQ ID NO 150
<211> LENGTH: 8
<212> TYPE: PRT
<213> ORGANISM: Artificial Sequence
<220> FEATURE:
<223> OTHER INFORMATION: Light CDR3 Clone CP_02_A04

<400> SEQUENCE: 150

Gln Ser Tyr Asp Asp Ser Asn Tyr
1               5

<210> SEQ ID NO 151
<211> LENGTH: 9
<212> TYPE: PRT
<213> ORGANISM: Artificial Sequence
<220> FEATURE:
<223> OTHER INFORMATION: Light CDR3 Clone CP_01_E08
```

```
<400> SEQUENCE: 151

Ser Ser Tyr Ala Gly Ser Asn Thr Leu
1               5

<210> SEQ ID NO 152
<211> LENGTH: 7
<212> TYPE: PRT
<213> ORGANISM: Artificial Sequence
<220> FEATURE:
<223> OTHER INFORMATION: Light CDR3 Clone CP_01_A08

<400> SEQUENCE: 152

Gln Gln Ala Asn Ser Phe Pro
1               5

<210> SEQ ID NO 153
<211> LENGTH: 7
<212> TYPE: PRT
<213> ORGANISM: Artificial Sequence
<220> FEATURE:
<223> OTHER INFORMATION: Light CDR3 Clone CP_01_D01

<400> SEQUENCE: 153

Gln Ser Tyr Asp Ser Ser Ile
1               5

<210> SEQ ID NO 154
<211> LENGTH: 7
<212> TYPE: PRT
<213> ORGANISM: Artificial Sequence
<220> FEATURE:
<223> OTHER INFORMATION: Light CDR3 Clone CP_02_A07

<400> SEQUENCE: 154

Gln Ser Tyr Asp Ser Ile His
1               5

<210> SEQ ID NO 155
<211> LENGTH: 8
<212> TYPE: PRT
<213> ORGANISM: Artificial Sequence
<220> FEATURE:
<223> OTHER INFORMATION: Light CDR3 Clone CP_02_B08

<400> SEQUENCE: 155

Gln Ser Tyr Asp Ser Ser Thr His
1               5

<210> SEQ ID NO 156
<211> LENGTH: 7
<212> TYPE: PRT
<213> ORGANISM: Artificial Sequence
<220> FEATURE:
<223> OTHER INFORMATION: Light CDR3 Clone CP_01_D09

<400> SEQUENCE: 156

Gln Gln Tyr Asp Asn Leu Pro
1               5

<210> SEQ ID NO 157
<211> LENGTH: 8
<212> TYPE: PRT
<213> ORGANISM: Artificial Sequence
<220> FEATURE:
<223> OTHER INFORMATION: Light CDR3 Clone CP_01_G07
```

<400> SEQUENCE: 157

Gln Ser Phe Thr Ser Ser Thr Leu
1               5

<210> SEQ ID NO 158
<211> LENGTH: 7
<212> TYPE: PRT
<213> ORGANISM: Artificial Sequence
<220> FEATURE:
<223> OTHER INFORMATION: Light CDR3 Clone CP_01_A05

<400> SEQUENCE: 158

Gln Gln Tyr Asn Lys Trp Pro
1               5

<210> SEQ ID NO 159
<211> LENGTH: 8
<212> TYPE: PRT
<213> ORGANISM: Artificial Sequence
<220> FEATURE:
<223> OTHER INFORMATION: Light CDR3 Clone CP_02_A08

<400> SEQUENCE: 159

Gln Ser Tyr Asp Asp Ser Asn Tyr
1               5

<210> SEQ ID NO 160
<211> LENGTH: 8
<212> TYPE: PRT
<213> ORGANISM: Artificial Sequence
<220> FEATURE:
<223> OTHER INFORMATION: Light CDR3 Clone CP_02_D07

<400> SEQUENCE: 160

Gln Ser Tyr Asp Ser Ser Asn His
1               5

<210> SEQ ID NO 161
<211> LENGTH: 7
<212> TYPE: PRT
<213> ORGANISM: Artificial Sequence
<220> FEATURE:
<223> OTHER INFORMATION: Light CDR3 Clone CP_01_C04

<400> SEQUENCE: 161

Gln Gln Ser Tyr Ser Thr Pro
1               5

<210> SEQ ID NO 162
<211> LENGTH: 10
<212> TYPE: PRT
<213> ORGANISM: Artificial Sequence
<220> FEATURE:
<223> OTHER INFORMATION: Light CDR3 Clone CP_01_A07

<400> SEQUENCE: 162

Asn Ser Arg Asp Ser Ser Gly Asn Pro Asn
1               5                   10

<210> SEQ ID NO 163
<211> LENGTH: 8
<212> TYPE: PRT
<213> ORGANISM: Artificial Sequence
<220> FEATURE:
<223> OTHER INFORMATION: Light CDR3 Clone CP_01_H02

<400> SEQUENCE: 163

```
Gln Ser Tyr Asp Ser Ser Asn Leu
1               5

<210> SEQ ID NO 164
<211> LENGTH: 8
<212> TYPE: PRT
<213> ORGANISM: Artificial Sequence
<220> FEATURE:
<223> OTHER INFORMATION: Light CDR3 Clone CP_01_F10

<400> SEQUENCE: 164

Gln Ser Tyr Asp Ser Ser Asn His
1               5

<210> SEQ ID NO 165
<211> LENGTH: 9
<212> TYPE: PRT
<213> ORGANISM: Artificial Sequence
<220> FEATURE:
<223> OTHER INFORMATION: Light CDR3 Clone CP_02_C10

<400> SEQUENCE: 165

Ala Val Trp Asp Asp Arg Leu Asn Gly
1               5

<210> SEQ ID NO 166
<211> LENGTH: 7
<212> TYPE: PRT
<213> ORGANISM: Artificial Sequence
<220> FEATURE:
<223> OTHER INFORMATION: Light CDR3 Clone CP_02_B05

<400> SEQUENCE: 166

Gln Gln Tyr Asp Ser Tyr Ser
1               5

<210> SEQ ID NO 167
<211> LENGTH: 9
<212> TYPE: PRT
<213> ORGANISM: Artificial Sequence
<220> FEATURE:
<223> OTHER INFORMATION: Light CDR3 Clone CP_01_G04

<400> SEQUENCE: 167

Gln Ser Ala Asp Ser Ser Gly Thr Asn
1               5

<210> SEQ ID NO 168
<211> LENGTH: 8
<212> TYPE: PRT
<213> ORGANISM: Artificial Sequence
<220> FEATURE:
<223> OTHER INFORMATION: Light CDR3 Clone CP_01_F08

<400> SEQUENCE: 168

Gln Ser Tyr Asp Ser Ser Asn His
1               5

<210> SEQ ID NO 169
<211> LENGTH: 8
<212> TYPE: PRT
<213> ORGANISM: Artificial Sequence
<220> FEATURE:
<223> OTHER INFORMATION: Light CDR3 Clone CP_01_G05

<400> SEQUENCE: 169
```

```
Gln Ser Tyr Asp Thr Arg Asn Gln
1               5
```

<210> SEQ ID NO 170
<211> LENGTH: 7
<212> TYPE: PRT
<213> ORGANISM: Artificial Sequence
<220> FEATURE:
<223> OTHER INFORMATION: Light CDR3 Clone CP_02_A03

<400> SEQUENCE: 170

```
Gln Gln Tyr Tyr Ser Thr Pro
1               5
```

<210> SEQ ID NO 171
<211> LENGTH: 6
<212> TYPE: PRT
<213> ORGANISM: Artificial Sequence
<220> FEATURE:
<223> OTHER INFORMATION: Light CDR3 Clone CP_01_B09

<400> SEQUENCE: 171

```
Gln Gln Ser Tyr Ser Thr
1               5
```

<210> SEQ ID NO 172
<211> LENGTH: 8
<212> TYPE: PRT
<213> ORGANISM: Artificial Sequence
<220> FEATURE:
<223> OTHER INFORMATION: Light CDR3 Clone CP_01_A10

<400> SEQUENCE: 172

```
Ala Ala Trp Asp Asp Ser Leu Phe
1               5
```

<210> SEQ ID NO 173
<211> LENGTH: 7
<212> TYPE: PRT
<213> ORGANISM: Artificial Sequence
<220> FEATURE:
<223> OTHER INFORMATION: Light CDR3 Clone CP_01_H04

<400> SEQUENCE: 173

```
Met Gln Arg Ile Glu Phe Pro
1               5
```

<210> SEQ ID NO 174
<211> LENGTH: 7
<212> TYPE: PRT
<213> ORGANISM: Artificial Sequence
<220> FEATURE:
<223> OTHER INFORMATION: Light CDR3 Clone CP_02_B04

<400> SEQUENCE: 174

```
Gln Gln Tyr Tyr Asn Thr Pro
1               5
```

<210> SEQ ID NO 175
<211> LENGTH: 7
<212> TYPE: PRT
<213> ORGANISM: Artificial Sequence
<220> FEATURE:
<223> OTHER INFORMATION: Light CDR3 Clone CP_02_A05

<400> SEQUENCE: 175

```
Gln Ser Tyr Asp Ser Ser Ile
```

<210> SEQ ID NO 176
<211> LENGTH: 8
<212> TYPE: PRT
<213> ORGANISM: Artificial Sequence
<220> FEATURE:
<223> OTHER INFORMATION: Light CDR3 Clone CP_01_F07

<400> SEQUENCE: 176

Gln Ser Tyr Asp Ser Thr Asn Leu
1               5

<210> SEQ ID NO 177
<211> LENGTH: 7
<212> TYPE: PRT
<213> ORGANISM: Artificial Sequence
<220> FEATURE:
<223> OTHER INFORMATION: Light CDR3 Clone CP_01_H01

<400> SEQUENCE: 177

Gln Gln Ser Tyr Ser Thr Pro
1               5

<210> SEQ ID NO 178
<211> LENGTH: 9
<212> TYPE: PRT
<213> ORGANISM: Artificial Sequence
<220> FEATURE:
<223> OTHER INFORMATION: Light CDR3 Clone CP_01_G10

<400> SEQUENCE: 178

Asn Ser Arg Asp Ser Ser Gly Asn His
1               5

<210> SEQ ID NO 179
<211> LENGTH: 7
<212> TYPE: PRT
<213> ORGANISM: Artificial Sequence
<220> FEATURE:
<223> OTHER INFORMATION: Light CDR3 Clone CP_01_G11

<400> SEQUENCE: 179

Gln Gln Ser Tyr Ser Thr Pro
1               5

<210> SEQ ID NO 180
<211> LENGTH: 9
<212> TYPE: PRT
<213> ORGANISM: Artificial Sequence
<220> FEATURE:
<223> OTHER INFORMATION: Light CDR3 Clone CP_01_G01
<220> FEATURE:
<221> NAME/KEY: misc_feature
<222> LOCATION: (9)..(9)
<223> OTHER INFORMATION: Xaa can be any naturally occurring amino acid

<400> SEQUENCE: 180

Asp Ser Arg Asp Thr Arg Val Asn Xaa
1               5

<210> SEQ ID NO 181
<211> LENGTH: 6
<212> TYPE: PRT
<213> ORGANISM: Artificial Sequence
<220> FEATURE:
<223> OTHER INFORMATION: Light CDR3 Clone CP_01_A12

```
<400> SEQUENCE: 181

Gln Gln Tyr Asp Asn Leu
1               5

<210> SEQ ID NO 182
<211> LENGTH: 7
<212> TYPE: PRT
<213> ORGANISM: Artificial Sequence
<220> FEATURE:
<223> OTHER INFORMATION: Light CDR3 Clone CP_01_H05

<400> SEQUENCE: 182

Met Gln Ala Leu Gln Thr Pro
1               5

<210> SEQ ID NO 183
<211> LENGTH: 7
<212> TYPE: PRT
<213> ORGANISM: Artificial Sequence
<220> FEATURE:
<223> OTHER INFORMATION: Light CDR3 Clone CP_02_B07

<400> SEQUENCE: 183

Gln Ser Tyr Asp Ser Ser Asn
1               5

<210> SEQ ID NO 184
<211> LENGTH: 8
<212> TYPE: PRT
<213> ORGANISM: Artificial Sequence
<220> FEATURE:
<223> OTHER INFORMATION: Light CDR3 Clone CP_01_G09

<400> SEQUENCE: 184

Ser Ser Tyr Thr Ser Ser Ser Thr
1               5

<210> SEQ ID NO 185
<211> LENGTH: 8
<212> TYPE: PRT
<213> ORGANISM: Artificial Sequence
<220> FEATURE:
<223> OTHER INFORMATION: Light CDR3 Clone CP_02_C02

<400> SEQUENCE: 185

Met Gln Ala Leu Gln Thr Pro Pro
1               5

<210> SEQ ID NO 186
<211> LENGTH: 8
<212> TYPE: PRT
<213> ORGANISM: Artificial Sequence
<220> FEATURE:
<223> OTHER INFORMATION: Light CDR3 Clone CP_01_D05

<400> SEQUENCE: 186

Gln Ser Tyr Asp Ser Thr Asn His
1               5

<210> SEQ ID NO 187
<211> LENGTH: 8
<212> TYPE: PRT
<213> ORGANISM: Artificial Sequence
<220> FEATURE:
<223> OTHER INFORMATION: Light CDR3 Clone CP_01_D08

<400> SEQUENCE: 187
```

Gln Ser Tyr Asp Ser Ala Asn Leu
1               5

<210> SEQ ID NO 188
<211> LENGTH: 8
<212> TYPE: PRT
<213> ORGANISM: Artificial Sequence
<220> FEATURE:
<223> OTHER INFORMATION: Light CDR3 Clone CP_02_A11

<400> SEQUENCE: 188

Gln Ser Phe Asp Glu Asn Ile Ser
1               5

<210> SEQ ID NO 189
<211> LENGTH: 7
<212> TYPE: PRT
<213> ORGANISM: Artificial Sequence
<220> FEATURE:
<223> OTHER INFORMATION: Light CDR3 Clone CP_02_D08

<400> SEQUENCE: 189

His Gln Ser Ala Thr Ser Pro
1               5

<210> SEQ ID NO 190
<211> LENGTH: 7
<212> TYPE: PRT
<213> ORGANISM: Artificial Sequence
<220> FEATURE:
<223> OTHER INFORMATION: Heavy CDR3 Clone CP_03_E05

<400> SEQUENCE: 190

Thr Arg Ser Ser Gly Ala Phe
1               5

<210> SEQ ID NO 191
<211> LENGTH: 8
<212> TYPE: PRT
<213> ORGANISM: Artificial Sequence
<220> FEATURE:
<223> OTHER INFORMATION: Heavy CDR3 Clone CP_03_D05

<400> SEQUENCE: 191

Pro Arg Gly Arg Gly Ser Ala Phe
1               5

<210> SEQ ID NO 192
<211> LENGTH: 6
<212> TYPE: PRT
<213> ORGANISM: Artificial Sequence
<220> FEATURE:
<223> OTHER INFORMATION: Heavy CDR3 Clone CP_03_H06

<400> SEQUENCE: 192

Ala Arg Val Gly Gly Met
1               5

<210> SEQ ID NO 193
<211> LENGTH: 5
<212> TYPE: PRT
<213> ORGANISM: Artificial Sequence
<220> FEATURE:
<223> OTHER INFORMATION: Heavy CDR3 Clone CP_03_C12

<400> SEQUENCE: 193

```
Asp Thr Gly Pro Ile
1               5

<210> SEQ ID NO 194
<211> LENGTH: 11
<212> TYPE: PRT
<213> ORGANISM: Artificial Sequence
<220> FEATURE:
<223> OTHER INFORMATION: Heavy CDR3 Clone CP_03_G02

<400> SEQUENCE: 194

Gly Val Trp Asn Ser Gly Ser Tyr Leu Gly Phe
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Heavy CDR3 Clone CP_03_D04

<400> SEQUENCE: 195

Gly Gly Phe Thr Val Pro Gly Gly Ala Phe
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Heavy CDR3 Clone CP_03_F10

<400> SEQUENCE: 196

Phe Gly Glu Arg Tyr Ala Phe
1               5

<210> SEQ ID NO 197
<211> LENGTH: 12
<212> TYPE: PRT
<213> ORGANISM: Artificial Sequence
<220> FEATURE:
<223> OTHER INFORMATION: Heavy CDR3 Clone CP_03_G09

<400> SEQUENCE: 197

Asp Gln Trp Leu Ala Asn Tyr Tyr Tyr Tyr Gly Met
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Heavy CDR3 Clone CP_03_F09

<400> SEQUENCE: 198

Asn Arg Gly Gly Ser Tyr Lys Ser Val Gly Met
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Heavy CDR3 Clone CP_03_D09

<400> SEQUENCE: 199

Val Ser Ser Tyr Tyr Gly Met
```

```
<210> SEQ ID NO 200
<211> LENGTH: 7
<212> TYPE: PRT
<213> ORGANISM: Artificial Sequence
<220> FEATURE:
<223> OTHER INFORMATION: Heavy CDR3 Clone CP_03_F02

<400> SEQUENCE: 200

Ala Pro Ala Ser Ser Ala His
1               5

<210> SEQ ID NO 201
<211> LENGTH: 8
<212> TYPE: PRT
<213> ORGANISM: Artificial Sequence
<220> FEATURE:
<223> OTHER INFORMATION: Heavy CDR3 Clone CP_02_E03

<400> SEQUENCE: 201

Gln Arg Gly Tyr Tyr Tyr Gly Met
1               5

<210> SEQ ID NO 202
<211> LENGTH: 8
<212> TYPE: PRT
<213> ORGANISM: Artificial Sequence
<220> FEATURE:
<223> OTHER INFORMATION: Heavy CDR3 Clone CP_03_H07

<400> SEQUENCE: 202

Ser Ser Val Ala Ala Gly Ala Phe
1               5

<210> SEQ ID NO 203
<211> LENGTH: 8
<212> TYPE: PRT
<213> ORGANISM: Artificial Sequence
<220> FEATURE:
<223> OTHER INFORMATION: Heavy CDR3 Clone CP_03_C02

<400> SEQUENCE: 203

Leu Ser Gly Arg Gly Leu Gly Phe
1               5

<210> SEQ ID NO 204
<211> LENGTH: 4
<212> TYPE: PRT
<213> ORGANISM: Artificial Sequence
<220> FEATURE:
<223> OTHER INFORMATION: Heavy CDR3 Clone CP_03_E09

<400> SEQUENCE: 204

Asp His Tyr Phe
1

<210> SEQ ID NO 205
<211> LENGTH: 8
<212> TYPE: PRT
<213> ORGANISM: Artificial Sequence
<220> FEATURE:
<223> OTHER INFORMATION: Heavy CDR3 Clone CP_03_D08

<400> SEQUENCE: 205

Ser Gly Arg Arg Val Thr Ala Ile
1               5
```

<210> SEQ ID NO 206
<211> LENGTH: 8
<212> TYPE: PRT
<213> ORGANISM: Artificial Sequence
<220> FEATURE:
<223> OTHER INFORMATION: Heavy CDR3 Clone CP_03_E11

<400> SEQUENCE: 206

Met Gly Arg Tyr Ser Ser Ser Trp
1               5

<210> SEQ ID NO 207
<211> LENGTH: 8
<212> TYPE: PRT
<213> ORGANISM: Artificial Sequence
<220> FEATURE:
<223> OTHER INFORMATION: Heavy CDR3 Clone CP_03_B05

<400> SEQUENCE: 207

His Ser Arg Phe Gly Pro Ala Phe
1               5

<210> SEQ ID NO 208
<211> LENGTH: 5
<212> TYPE: PRT
<213> ORGANISM: Artificial Sequence
<220> FEATURE:
<223> OTHER INFORMATION: Heavy CDR3 Clone CP_03_H02

<400> SEQUENCE: 208

Asp Arg Glu Ala Phe
1               5

<210> SEQ ID NO 209
<211> LENGTH: 13
<212> TYPE: PRT
<213> ORGANISM: Artificial Sequence
<220> FEATURE:
<223> OTHER INFORMATION: Heavy CDR3 Clone CP_03_D02

<400> SEQUENCE: 209

Leu Arg Gly Arg Tyr Ser Tyr Gly Tyr Ser Asp Ala Phe
1               5                   10

<210> SEQ ID NO 210
<211> LENGTH: 9
<212> TYPE: PRT
<213> ORGANISM: Artificial Sequence
<220> FEATURE:
<223> OTHER INFORMATION: Heavy CDR3 Clone CP_03_E01

<400> SEQUENCE: 210

Leu Leu Asn Ala Val Thr Tyr Ala Phe
1               5

<210> SEQ ID NO 211
<211> LENGTH: 7
<212> TYPE: PRT
<213> ORGANISM: Artificial Sequence
<220> FEATURE:
<223> OTHER INFORMATION: Heavy CDR3 Clone CP_03_C11

<400> SEQUENCE: 211

Ile Gly Val Ile Gly Gly Phe
1               5

<210> SEQ ID NO 212
<211> LENGTH: 10
<212> TYPE: PRT
<213> ORGANISM: Artificial Sequence
<220> FEATURE:
<223> OTHER INFORMATION: Heavy CDR3 Clone CP_03_B12

<400> SEQUENCE: 212

Ile Glu Tyr Ser Ser Ser Ser Pro Tyr Phe
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Heavy CDR3 Clone CP_03_E03

<400> SEQUENCE: 213

Asp Leu Leu Pro Thr Thr Val Thr Thr Thr Gly Ala Phe
1               5                   10

<210> SEQ ID NO 214
<211> LENGTH: 6
<212> TYPE: PRT
<213> ORGANISM: Artificial Sequence
<220> FEATURE:
<223> OTHER INFORMATION: Heavy CDR3 Clone CP_03_F01

<400> SEQUENCE: 214

Asp Ser Gly Ser Tyr Ser
1               5

<210> SEQ ID NO 215
<211> LENGTH: 12
<212> TYPE: PRT
<213> ORGANISM: Artificial Sequence
<220> FEATURE:
<223> OTHER INFORMATION: Heavy CDR3 Clone CP_03_C01

<400> SEQUENCE: 215

Ala Ser Tyr Pro Tyr Tyr Tyr Tyr Tyr Tyr Gly Met
1               5                   10

<210> SEQ ID NO 216
<211> LENGTH: 5
<212> TYPE: PRT
<213> ORGANISM: Artificial Sequence
<220> FEATURE:
<223> OTHER INFORMATION: Heavy CDR3 Clone CP_03_G07

<400> SEQUENCE: 216

Ala Leu Gly His Phe
1               5

<210> SEQ ID NO 217
<211> LENGTH: 7
<212> TYPE: PRT
<213> ORGANISM: Artificial Sequence
<220> FEATURE:
<223> OTHER INFORMATION: Heavy CDR3 Clone CP_03_E02

<400> SEQUENCE: 217

Phe Thr Thr Gly Ser Ala Leu
1               5

```
<210> SEQ ID NO 218
<211> LENGTH: 5
<212> TYPE: PRT
<213> ORGANISM: Artificial Sequence
<220> FEATURE:
<223> OTHER INFORMATION: Heavy CDR3 Clone CP_03_C07

<400> SEQUENCE: 218

Asp Ala Ser Gly Tyr
1               5

<210> SEQ ID NO 219
<211> LENGTH: 11
<212> TYPE: PRT
<213> ORGANISM: Artificial Sequence
<220> FEATURE:
<223> OTHER INFORMATION: Heavy CDR3 Clone CP_03_H04

<400> SEQUENCE: 219

Asp Leu Gly Thr Tyr Tyr Tyr Gly Ser Gly Asp
1               5                   10

<210> SEQ ID NO 220
<211> LENGTH: 8
<212> TYPE: PRT
<213> ORGANISM: Artificial Sequence
<220> FEATURE:
<223> OTHER INFORMATION: Heavy CDR3 Clone CP_03_E06

<400> SEQUENCE: 220

Val Gly Glu Leu Leu Gly Ala Phe
1               5

<210> SEQ ID NO 221
<211> LENGTH: 8
<212> TYPE: PRT
<213> ORGANISM: Artificial Sequence
<220> FEATURE:
<223> OTHER INFORMATION: Light CDR3 Clone CP_03_E05

<400> SEQUENCE: 221

His Ser Tyr Asp Ser Asn Asn His
1               5

<210> SEQ ID NO 222
<211> LENGTH: 9
<212> TYPE: PRT
<213> ORGANISM: Artificial Sequence
<220> FEATURE:
<223> OTHER INFORMATION: Heavy CDR3 Clone CP_03_G11

<400> SEQUENCE: 222

His Ser Gly Val Gly Gly Leu Ala Phe
1               5

<210> SEQ ID NO 223
<211> LENGTH: 10
<212> TYPE: PRT
<213> ORGANISM: Artificial Sequence
<220> FEATURE:
<223> OTHER INFORMATION: Heavy CDR3 Clone CP_03_G01

<400> SEQUENCE: 223

Gly Gly Ser Ile Ala Ala Ala Leu Ala Phe
1               5                   10

<210> SEQ ID NO 224
```

```
<211> LENGTH: 8
<212> TYPE: PRT
<213> ORGANISM: Artificial Sequence
<220> FEATURE:
<223> OTHER INFORMATION: Heavy CDR3 Clone CP_03_H01

<400> SEQUENCE: 224

Val Glu Tyr Ser Arg Asn Gly Met
1               5

<210> SEQ ID NO 225
<211> LENGTH: 4
<212> TYPE: PRT
<213> ORGANISM: Artificial Sequence
<220> FEATURE:
<223> OTHER INFORMATION: Heavy CDR3 Clone CP_03_F11

<400> SEQUENCE: 225

Gly Arg Tyr Asn
1

<210> SEQ ID NO 226
<211> LENGTH: 7
<212> TYPE: PRT
<213> ORGANISM: Artificial Sequence
<220> FEATURE:
<223> OTHER INFORMATION: Heavy CDR3 Clone CP_03_C06

<400> SEQUENCE: 226

Leu Asp Tyr Tyr Tyr Gly Met
1               5

<210> SEQ ID NO 227
<211> LENGTH: 7
<212> TYPE: PRT
<213> ORGANISM: Artificial Sequence
<220> FEATURE:
<223> OTHER INFORMATION: Heavy CDR3 Clone CP_03_D03

<400> SEQUENCE: 227

Gly Gly Leu Ser Ser Ala Phe
1               5

<210> SEQ ID NO 228
<211> LENGTH: 5
<212> TYPE: PRT
<213> ORGANISM: Artificial Sequence
<220> FEATURE:
<223> OTHER INFORMATION: Heavy CDR3 Clone CP_03_G05

<400> SEQUENCE: 228

Tyr Gly Gly Gly Leu
1               5

<210> SEQ ID NO 229
<211> LENGTH: 7
<212> TYPE: PRT
<213> ORGANISM: Artificial Sequence
<220> FEATURE:
<223> OTHER INFORMATION: Heavy CDR3 Clone CP_03_G12

<400> SEQUENCE: 229

Pro Asp His Leu Thr Val Phe
1               5

<210> SEQ ID NO 230
<211> LENGTH: 6
```

```
<212> TYPE: PRT
<213> ORGANISM: Artificial Sequence
<220> FEATURE:
<223> OTHER INFORMATION: Heavy CDR3 Clone CP_03_C10

<400> SEQUENCE: 230

Val Gly Tyr Tyr Gly Met
 1               5

<210> SEQ ID NO 231
<211> LENGTH: 7
<212> TYPE: PRT
<213> ORGANISM: Artificial Sequence
<220> FEATURE:
<223> OTHER INFORMATION: Heavy CDR3 Clone CP_03_F04

<400> SEQUENCE: 231

Tyr Glu Gly Tyr Ala Gly Phe
 1               5

<210> SEQ ID NO 232
<211> LENGTH: 8
<212> TYPE: PRT
<213> ORGANISM: Artificial Sequence
<220> FEATURE:
<223> OTHER INFORMATION: Light CDR3 Clone CP_03_D05

<400> SEQUENCE: 232

Gln Ala Trp Asp Thr Asn Leu Gly
 1               5

<210> SEQ ID NO 233
<211> LENGTH: 9
<212> TYPE: PRT
<213> ORGANISM: Artificial Sequence
<220> FEATURE:
<223> OTHER INFORMATION: Light CDR3 Clone CP_03_H06

<400> SEQUENCE: 233

Gln Ser Phe Asp Ala Asp Asn Leu His
 1               5

<210> SEQ ID NO 234
<211> LENGTH: 7
<212> TYPE: PRT
<213> ORGANISM: Artificial Sequence
<220> FEATURE:
<223> OTHER INFORMATION: Light CDR3 Clone CP_03_C12

<400> SEQUENCE: 234

Met Gln Gly Ile Gln Leu Pro
 1               5

<210> SEQ ID NO 235
<211> LENGTH: 7
<212> TYPE: PRT
<213> ORGANISM: Artificial Sequence
<220> FEATURE:
<223> OTHER INFORMATION: Light CDR3 Clone CP_03_G02

<400> SEQUENCE: 235

Gln Gln Ser Tyr Ser Thr Pro
 1               5

<210> SEQ ID NO 236
<211> LENGTH: 7
<212> TYPE: PRT
```

<213> ORGANISM: Artificial Sequence
<220> FEATURE:
<223> OTHER INFORMATION: Light CDR3 Clone CP_03_D04

<400> SEQUENCE: 236

Gln Ser Tyr Asp Ala Ser Asn
1               5

<210> SEQ ID NO 237
<211> LENGTH: 7
<212> TYPE: PRT
<213> ORGANISM: Artificial Sequence
<220> FEATURE:
<223> OTHER INFORMATION: Light CDR3 Clone CP_03_F10

<400> SEQUENCE: 237

Ser Ala Tyr Thr Gly Ser Asn
1               5

<210> SEQ ID NO 238
<211> LENGTH: 7
<212> TYPE: PRT
<213> ORGANISM: Artificial Sequence
<220> FEATURE:
<223> OTHER INFORMATION: Light CDR3 Clone CP_03_G09

<400> SEQUENCE: 238

Gln Val Trp Asp Ser Asn Ser
1               5

<210> SEQ ID NO 239
<211> LENGTH: 7
<212> TYPE: PRT
<213> ORGANISM: Artificial Sequence
<220> FEATURE:
<223> OTHER INFORMATION: Light CDR3 Clone CP_03_F09

<400> SEQUENCE: 239

Gln Ser Tyr Asp Glu Val Ser
1               5

<210> SEQ ID NO 240
<211> LENGTH: 8
<212> TYPE: PRT
<213> ORGANISM: Artificial Sequence
<220> FEATURE:
<223> OTHER INFORMATION: Light CDR3 Clone CP_03_D09

<400> SEQUENCE: 240

Gln Ser Tyr Asn Ser Ser Asn His
1               5

<210> SEQ ID NO 241
<211> LENGTH: 7
<212> TYPE: PRT
<213> ORGANISM: Artificial Sequence
<220> FEATURE:
<223> OTHER INFORMATION: Light CDR3 Clone CP_03_F02

<400> SEQUENCE: 241

Gln Ser Tyr Asp Ser Ser His
1               5

<210> SEQ ID NO 242
<211> LENGTH: 7
<212> TYPE: PRT
<213> ORGANISM: Artificial Sequence
<220> FEATURE:
<223> OTHER INFORMATION: Light CDR3 Clone CP_02_E03

<400> SEQUENCE: 242

Gln Gln Ser Arg Ser Thr Pro
1               5

<210> SEQ ID NO 243
<211> LENGTH: 8
<212> TYPE: PRT
<213> ORGANISM: Artificial Sequence
<220> FEATURE:
<223> OTHER INFORMATION: Light CDR3 Clone CP_03_H07

<400> SEQUENCE: 243

Ser Ser Tyr Thr Ser Ser Ser Thr
1               5

<210> SEQ ID NO 244
<211> LENGTH: 9
<212> TYPE: PRT
<213> ORGANISM: Artificial Sequence
<220> FEATURE:
<223> OTHER INFORMATION: Light CDR3 Clone CP_03_C02

<400> SEQUENCE: 244

Ser Ser Tyr Ala Gly Ser Ser Asn Leu
1               5

<210> SEQ ID NO 245
<211> LENGTH: 8
<212> TYPE: PRT
<213> ORGANISM: Artificial Sequence
<220> FEATURE:
<223> OTHER INFORMATION: Light CDR3 Clone CP_03_E09

<400> SEQUENCE: 245

Asn Ser Tyr Thr Arg Ser Ser Thr
1               5

<210> SEQ ID NO 246
<211> LENGTH: 7
<212> TYPE: PRT
<213> ORGANISM: Artificial Sequence
<220> FEATURE:
<223> OTHER INFORMATION: Light CDR3 Clone CP_03_D08

<400> SEQUENCE: 246

Gln Ser Tyr Asp Asp Thr Asn
1               5

<210> SEQ ID NO 247
<211> LENGTH: 8
<212> TYPE: PRT
<213> ORGANISM: Artificial Sequence
<220> FEATURE:
<223> OTHER INFORMATION: Light CDR3 Clone CP_03_E11

<400> SEQUENCE: 247

Gln Ala Trp Asp Thr Asn Ile Gly
1               5

<210> SEQ ID NO 248
<211> LENGTH: 8
<212> TYPE: PRT
<213> ORGANISM: Artificial Sequence
<220> FEATURE:

```
<223> OTHER INFORMATION: Light CDR3 Clone CP_03_B05

<400> SEQUENCE: 248

Ser Ser Tyr Ala Gly Ser Asn Asn
1               5

<210> SEQ ID NO 249
<211> LENGTH: 8
<212> TYPE: PRT
<213> ORGANISM: Artificial Sequence
<220> FEATURE:
<223> OTHER INFORMATION: Light CDR3 Clone CP_03_H02

<400> SEQUENCE: 249

Gln Ala Trp Asp Thr Asn Ile Gly
1               5

<210> SEQ ID NO 250
<211> LENGTH: 8
<212> TYPE: PRT
<213> ORGANISM: Artificial Sequence
<220> FEATURE:
<223> OTHER INFORMATION: Light CDR3 Clone CP_03_D02

<400> SEQUENCE: 250

Ser Ser Tyr Ala Gly Ser Ser Thr
1               5

<210> SEQ ID NO 251
<211> LENGTH: 8
<212> TYPE: PRT
<213> ORGANISM: Artificial Sequence
<220> FEATURE:
<223> OTHER INFORMATION: Light CDR3 Clone CP_03_E01

<400> SEQUENCE: 251

Asn Ser Arg Asp Ser Ser Gly Phe
1               5

<210> SEQ ID NO 252
<211> LENGTH: 7
<212> TYPE: PRT
<213> ORGANISM: Artificial Sequence
<220> FEATURE:
<223> OTHER INFORMATION: Light CDR3 Clone CP_03_C11

<400> SEQUENCE: 252

Ser Ser Tyr Thr Ser Ser Ser
1               5

<210> SEQ ID NO 253
<211> LENGTH: 8
<212> TYPE: PRT
<213> ORGANISM: Artificial Sequence
<220> FEATURE:
<223> OTHER INFORMATION: Light CDR3 Clone CP_03_B12

<400> SEQUENCE: 253

Gln Ser Tyr Asp Ser Asn Asn Arg
1               5

<210> SEQ ID NO 254
<211> LENGTH: 9
<212> TYPE: PRT
<213> ORGANISM: Artificial Sequence
<220> FEATURE:
<223> OTHER INFORMATION: Light CDR3 Clone CP_03_E03
```

-continued

```
<400> SEQUENCE: 254

Ser Ser Arg Asp Ser Ser Gly Asn His
1               5

<210> SEQ ID NO 255
<211> LENGTH: 8
<212> TYPE: PRT
<213> ORGANISM: Artificial Sequence
<220> FEATURE:
<223> OTHER INFORMATION: Light CDR3 Clone CP_03_F01

<400> SEQUENCE: 255

Gln Ala Trp Asp Thr Asn Ile Gly
1               5

<210> SEQ ID NO 256
<211> LENGTH: 9
<212> TYPE: PRT
<213> ORGANISM: Artificial Sequence
<220> FEATURE:
<223> OTHER INFORMATION: Light CDR3 Clone CP_03_C01

<400> SEQUENCE: 256

Gln Val Trp Asp Ser Ser Thr Ala Asn
1               5

<210> SEQ ID NO 257
<211> LENGTH: 9
<212> TYPE: PRT
<213> ORGANISM: Artificial Sequence
<220> FEATURE:
<223> OTHER INFORMATION: Light CDR3 Clone CP_03_G07

<400> SEQUENCE: 257

Gln Ser Tyr Asp Ser Ser Asn His His
1               5

<210> SEQ ID NO 258
<211> LENGTH: 8
<212> TYPE: PRT
<213> ORGANISM: Artificial Sequence
<220> FEATURE:
<223> OTHER INFORMATION: Light CDR3 Clone CP_03_E02

<400> SEQUENCE: 258

Ser Ser Tyr Ala Gly Asn Ser Asn
1               5

<210> SEQ ID NO 259
<211> LENGTH: 8
<212> TYPE: PRT
<213> ORGANISM: Artificial Sequence
<220> FEATURE:
<223> OTHER INFORMATION: Light CDR3 Clone CP_03_C07

<400> SEQUENCE: 259

Gln Ala Trp Asp Thr Asn Ile Gly
1               5

<210> SEQ ID NO 260
<211> LENGTH: 10
<212> TYPE: PRT
<213> ORGANISM: Artificial Sequence
<220> FEATURE:
<223> OTHER INFORMATION: Light CDR3 Clone CP_03_H04
```

```
<400> SEQUENCE: 260

Gly Thr Trp Asp Ser Ser Leu Ser Ala Gly
1               5                   10

<210> SEQ ID NO 261
<211> LENGTH: 9
<212> TYPE: PRT
<213> ORGANISM: Artificial Sequence
<220> FEATURE:
<223> OTHER INFORMATION: Light CDR3 Clone CP_03_E06

<400> SEQUENCE: 261

Ser Ser Leu Asp Ser Asn Asp Asn His
1               5

<210> SEQ ID NO 262
<211> LENGTH: 9
<212> TYPE: PRT
<213> ORGANISM: Artificial Sequence
<220> FEATURE:
<223> OTHER INFORMATION: Light CDR3 Clone CP_03_H03

<400> SEQUENCE: 262

Ala Ala Trp Asp Asp Ser Leu Asn Gly
1               5

<210> SEQ ID NO 263
<211> LENGTH: 8
<212> TYPE: PRT
<213> ORGANISM: Artificial Sequence
<220> FEATURE:
<223> OTHER INFORMATION: Light CDR3 Clone CP_03_G11

<400> SEQUENCE: 263

Ser Ser Tyr Ala Gly Ser Ser Thr
1               5

<210> SEQ ID NO 264
<211> LENGTH: 7
<212> TYPE: PRT
<213> ORGANISM: Artificial Sequence
<220> FEATURE:
<223> OTHER INFORMATION: Light CDR3 Clone CP_03_G01

<400> SEQUENCE: 264

His Gln Tyr Asp Val Tyr Pro
1               5

<210> SEQ ID NO 265
<211> LENGTH: 9
<212> TYPE: PRT
<213> ORGANISM: Artificial Sequence
<220> FEATURE:
<223> OTHER INFORMATION: Light CDR3 Clone CP_03_H01

<400> SEQUENCE: 265

Asn Ser Arg Asp Ser Ser Gly Asn His
1               5

<210> SEQ ID NO 266
<211> LENGTH: 7
<212> TYPE: PRT
<213> ORGANISM: Artificial Sequence
<220> FEATURE:
<223> OTHER INFORMATION: Light CDR3 Clone CP_03_F11

<400> SEQUENCE: 266
```

```
Gln Ser Tyr Asp Ser Ser Asn
1               5

<210> SEQ ID NO 267
<211> LENGTH: 7
<212> TYPE: PRT
<213> ORGANISM: Artificial Sequence
<220> FEATURE:
<223> OTHER INFORMATION: Light CDR3 Clone CP_03_C06

<400> SEQUENCE: 267

Gln Ser Tyr Asp Ser Ser Asn
1               5

<210> SEQ ID NO 268
<211> LENGTH: 7
<212> TYPE: PRT
<213> ORGANISM: Artificial Sequence
<220> FEATURE:
<223> OTHER INFORMATION: Light CDR3 Clone CP_03_D03

<400> SEQUENCE: 268

Gln Ser Tyr Asp Ser Ser Asn
1               5

<210> SEQ ID NO 269
<211> LENGTH: 8
<212> TYPE: PRT
<213> ORGANISM: Artificial Sequence
<220> FEATURE:
<223> OTHER INFORMATION: Light CDR3 Clone CP_03_G05

<400> SEQUENCE: 269

Ser Ser Tyr Ala Gly Ser Tyr Thr
1               5

<210> SEQ ID NO 270
<211> LENGTH: 7
<212> TYPE: PRT
<213> ORGANISM: Artificial Sequence
<220> FEATURE:
<223> OTHER INFORMATION: Light CDR3 Clone CP_03_G12

<400> SEQUENCE: 270

Ser Ser Tyr Thr Pro Ser Ser
1               5

<210> SEQ ID NO 271
<211> LENGTH: 8
<212> TYPE: PRT
<213> ORGANISM: Artificial Sequence
<220> FEATURE:
<223> OTHER INFORMATION: Light CDR3 Clone CP_03_C10

<400> SEQUENCE: 271

Gln Ala Trp Asp Thr Asn Ile Gly
1               5

<210> SEQ ID NO 272
<211> LENGTH: 8
<212> TYPE: PRT
<213> ORGANISM: Artificial Sequence
<220> FEATURE:
<223> OTHER INFORMATION: Light CDR3 Clone CP_03_F04
```

```
<400> SEQUENCE: 272

Gln Ala Trp Asp Thr Asn Ile Gly
1               5
```